(12) United States Patent
Tinkham et al.

(10) Patent No.: US 11,864,764 B2
(45) Date of Patent: Jan. 9, 2024

(54) SYSTEMS, DEVICES, AND METHODS FOR ENDOSCOPE OR LAPAROSCOPIC MAGNETIC NAVIGATION

(71) Applicant: G.I. Windows, Inc., Westwood, MA (US)

(72) Inventors: Brian P. Tinkham, Scituate, MA (US); Dane T. Seddon, Boston, MA (US); Natan Zundel, North Miami Beach, FL (US); Jiping C. Wang, Chestnut Hill, MA (US); Shani Mann, Needham, MA (US)

(73) Assignee: G.I. Windows, Inc., Westwood, MA (US)

( * ) Notice: Subject to any disclaimer, the term of this patent is extended or adjusted under 35 U.S.C. 154(b) by 0 days.

(21) Appl. No.: 18/110,467

(22) Filed: Feb. 16, 2023

(65) Prior Publication Data
US 2023/0190269 A1 Jun. 22, 2023

Related U.S. Application Data

(63) Continuation of application No. PCT/US2022/025343, filed on Apr. 19, 2022.

(60) Provisional application No. 63/177,162, filed on Apr. 20, 2021.

(51) Int. Cl.
| | | |
|---|---|---|
| A61B 17/072 | (2006.01) | |
| A61B 17/11 | (2006.01) | |
| A61B 17/00 | (2006.01) | |

(52) U.S. Cl.
CPC ...... *A61B 17/07207* (2013.01); *A61B 17/1114* (2013.01); *A61B 2017/003* (2013.01); *A61B 2017/00022* (2013.01); *A61B 2017/00296* (2013.01); *A61B 2017/00876* (2013.01); *A61B 2017/1103* (2013.01)

(58) Field of Classification Search
CPC .......... A61B 17/07207; A61B 17/1114; A61B 2017/00022; A61B 2017/003; A61B 2017/00876; A61B 2017/1103
See application file for complete search history.

(56) References Cited

U.S. PATENT DOCUMENTS

| | | | |
|---|---|---|---|
| 4,197,840 A | 4/1980 | Beck et al. | |
| 4,538,130 A | 8/1985 | Gluckstern et al. | |
| 5,300,910 A | 4/1994 | Unkelbach et al. | |
| (Continued) | | | |

FOREIGN PATENT DOCUMENTS

| | | |
|---|---|---|
| DE | 3011742 A1 | 10/1981 |
| EP | 1894514 A2 | 3/2008 |
| (Continued) | | |

OTHER PUBLICATIONS

Extended European Search Report of the European Patent Office, Application No. 19810895.3, dated Feb. 7, 2022, 10 pages.
(Continued)

*Primary Examiner* — Jocelin C Tanner
(74) *Attorney, Agent, or Firm* — Nutter McClennen & Fish LLP

(57) ABSTRACT

The invention provides systems, devices, and methods for the delivery, deployment, and positioning of magnetic compression devices at a desired site so as to improve the accuracy of anastomoses creation between tissues, organs, or the like.

30 Claims, 68 Drawing Sheets

(56) References Cited

U.S. PATENT DOCUMENTS

| | | | |
|---|---|---|---|
| 5,381,784 A * | 1/1995 | Adair | H04N 7/18 |
| | | | 348/45 |
| 5,431,670 A * | 7/1995 | Holmes | A61B 17/062 |
| | | | 606/147 |
| 5,595,562 A | 1/1997 | Grier | |
| 5,690,656 A | 11/1997 | Cope et al. | |
| 6,129,668 A | 10/2000 | Haynor et al. | |
| 6,132,458 A | 10/2000 | Staehle et al. | |
| 6,190,303 B1 | 2/2001 | Glenn et al. | |
| 6,273,895 B1 | 8/2001 | Pinchuk et al. | |
| 6,352,543 B1 | 3/2002 | Cole | |
| 6,371,964 B1 | 4/2002 | Vargas et al. | |
| 6,478,210 B2 * | 11/2002 | Adams | A61B 17/07207 |
| | | | 227/176.1 |
| 6,632,229 B1 | 10/2003 | Yamanouchi et al. | |
| 6,652,540 B1 | 11/2003 | Cole et al. | |
| 6,719,768 B1 | 4/2004 | Cole et al. | |
| 6,802,847 B1 | 10/2004 | Carson et al. | |
| 6,827,718 B2 | 12/2004 | Hutchins et al. | |
| 6,932,827 B2 | 8/2005 | Cole | |
| 7,282,057 B2 | 10/2007 | Surti et al. | |
| 7,618,427 B2 | 11/2009 | Oritz et al. | |
| 7,641,638 B2 | 1/2010 | Waxman et al. | |
| 7,760,059 B2 | 7/2010 | Higuchi | |
| 7,909,837 B2 | 3/2011 | Crews et al. | |
| 8,043,290 B2 | 10/2011 | Harrison et al. | |
| 8,118,821 B2 | 2/2012 | Mouw | |
| 8,142,454 B2 | 3/2012 | Harrison et al. | |
| 8,262,680 B2 | 9/2012 | Swain et al. | |
| 8,439,915 B2 | 5/2013 | Harrison et al. | |
| 8,506,516 B2 | 8/2013 | Kassab et al. | |
| 8,556,919 B2 | 10/2013 | Aguirre et al. | |
| 8,603,121 B2 | 12/2013 | Surti et al. | |
| 8,623,036 B2 | 1/2014 | Harrison et al. | |
| 8,679,139 B2 | 3/2014 | Aguirre et al. | |
| 8,685,046 B2 | 4/2014 | Viola | |
| 8,728,105 B2 | 5/2014 | Aguirre | |
| 8,794,243 B2 | 8/2014 | Deem et al. | |
| 8,828,031 B2 | 9/2014 | Fox et al. | |
| 8,845,663 B2 | 9/2014 | Chmura | |
| 8,864,781 B2 | 10/2014 | Surti et al. | |
| 8,870,899 B2 | 10/2014 | Beisel et al. | |
| 8,915,915 B2 | 12/2014 | Harrison et al. | |
| 9,168,041 B2 | 10/2015 | Zaritsky et al. | |
| 9,226,753 B2 | 1/2016 | Surti et al. | |
| 9,320,524 B2 | 4/2016 | Gagner et al. | |
| 9,421,015 B2 | 8/2016 | Gagner et al. | |
| 9,456,820 B2 | 10/2016 | Gagner et al. | |
| 9,492,173 B2 | 11/2016 | McWeeney et al. | |
| 9,539,010 B2 | 1/2017 | Gagner et al. | |
| 9,763,664 B2 | 9/2017 | Beisel et al. | |
| 9,801,635 B2 | 10/2017 | Gagner et al. | |
| 9,877,724 B2 | 1/2018 | Gagner et al. | |
| 9,943,335 B2 | 4/2018 | Gittard et al. | |
| 10,039,550 B2 | 8/2018 | Altman | |
| 10,159,487 B2 | 12/2018 | Gagner et al. | |
| 10,182,821 B2 | 1/2019 | Ukin et al. | |
| 10,285,703 B2 | 5/2019 | Viola | |
| 10,342,544 B2 | 7/2019 | Bakos et al. | |
| 10,376,400 B2 | 8/2019 | McGuckin, Jr. | |
| 10,448,954 B2 | 10/2019 | McWeeney et al. | |
| 10,517,600 B2 | 12/2019 | Beisel et al. | |
| 10,555,735 B2 | 2/2020 | Bakos et al. | |
| 10,568,630 B2 | 2/2020 | Hernandez et al. | |
| 10,624,643 B2 | 4/2020 | Hunt et al. | |
| 10,624,644 B2 | 4/2020 | Bakos et al. | |
| 10,631,865 B2 | 4/2020 | Bakos et al. | |
| 10,667,817 B2 | 6/2020 | Gagner et al. | |
| 10,682,143 B2 | 6/2020 | Hernandez et al. | |
| 10,779,831 B2 | 9/2020 | Lukin et al. | |
| 10,813,642 B2 | 10/2020 | Beisel et al. | |
| 10,952,732 B2 | 3/2021 | Binmoeller et al. | |
| 11,039,838 B2 | 6/2021 | Binmoeller et al. | |
| 11,311,298 B2 | 4/2022 | Gagner et al. | |
| 11,432,873 B2 | 9/2022 | Brown et al. | |
| 2002/0055674 A1 * | 5/2002 | Ben-Haim | A61B 5/6858 |
| | | | 600/374 |
| 2002/0143347 A1 | 10/2002 | Cole et al. | |
| 2003/0149422 A1 | 8/2003 | Muller | |
| 2003/0176767 A1 * | 9/2003 | Long | A61B 17/320016 |
| | | | 600/106 |
| 2004/0034377 A1 | 2/2004 | Sharkawy et al. | |
| 2005/0020958 A1 | 1/2005 | Paolini et al. | |
| 2005/0080439 A1 | 4/2005 | Carson et al. | |
| 2005/0277966 A1 | 12/2005 | Ewers et al. | |
| 2005/0283235 A1 | 12/2005 | Kugler et al. | |
| 2006/0036267 A1 | 2/2006 | Saadat et al. | |
| 2006/0271107 A1 | 11/2006 | Harrison et al. | |
| 2007/0106312 A1 | 5/2007 | Vargas et al. | |
| 2007/0276378 A1 | 11/2007 | Harrison et al. | |
| 2008/0051626 A1 | 2/2008 | Sato et al. | |
| 2008/0086192 A1 | 4/2008 | WasDyke et al. | |
| 2008/0114384 A1 | 5/2008 | Chang et al. | |
| 2008/0183272 A1 | 7/2008 | Wood et al. | |
| 2008/0200933 A1 | 8/2008 | Bakos et al. | |
| 2008/0200934 A1 | 8/2008 | Fox | |
| 2008/0208105 A1 | 8/2008 | Zelickson et al. | |
| 2008/0208224 A1 | 8/2008 | Surti et al. | |
| 2008/0262523 A1 | 10/2008 | Makower et al. | |
| 2009/0048618 A1 | 2/2009 | Harrison et al. | |
| 2009/0125042 A1 | 5/2009 | Mouw | |
| 2009/0227828 A1 | 9/2009 | Swain et al. | |
| 2010/0010508 A1 | 1/2010 | Takahashi et al. | |
| 2010/0010610 A1 | 1/2010 | Grevious | |
| 2010/0036399 A1 | 2/2010 | Viola | |
| 2010/0056861 A1 * | 3/2010 | Spivey | A61B 17/00234 |
| | | | 600/106 |
| 2010/0099947 A1 | 4/2010 | Sato et al. | |
| 2010/0179510 A1 | 7/2010 | Fox et al. | |
| 2011/0009886 A1 | 1/2011 | Gagner et al. | |
| 2011/0098731 A1 | 4/2011 | Whitbrook et al. | |
| 2011/0144560 A1 | 6/2011 | Gagner et al. | |
| 2011/0160751 A1 | 6/2011 | Granja Filho | |
| 2011/0160752 A1 | 6/2011 | Aguirre | |
| 2011/0295055 A1 | 12/2011 | Albrecht et al. | |
| 2011/0295285 A1 | 12/2011 | McWeeney et al. | |
| 2012/0022572 A1 | 1/2012 | Braun et al. | |
| 2012/0197062 A1 | 8/2012 | Requarth | |
| 2012/0238796 A1 | 9/2012 | Conlon | |
| 2012/0259350 A1 | 10/2012 | Gagner et al. | |
| 2012/0330330 A1 | 12/2012 | Gagner et al. | |
| 2013/0138126 A1 | 5/2013 | Gagner et al. | |
| 2013/0150873 A1 | 6/2013 | Gagner et al. | |
| 2013/0253548 A1 | 9/2013 | Harrison et al. | |
| 2013/0253550 A1 | 9/2013 | Beisel et al. | |
| 2013/0325042 A1 | 12/2013 | Fabian et al. | |
| 2014/0018824 A1 | 1/2014 | Julian et al. | |
| 2014/0019468 A1 | 1/2014 | Federoff et al. | |
| 2014/0066709 A1 | 3/2014 | Mirza et al. | |
| 2014/0188246 A1 | 7/2014 | Aronson et al. | |
| 2014/0194689 A1 | 7/2014 | Carrillo, Jr. et al. | |
| 2014/0236064 A1 | 8/2014 | Binmoeller et al. | |
| 2014/0303657 A1 | 10/2014 | Kim et al. | |
| 2014/0309669 A1 | 10/2014 | Fabian et al. | |
| 2014/0379065 A1 | 12/2014 | Johnson et al. | |
| 2015/0057687 A1 | 2/2015 | Gittard et al. | |
| 2015/0164508 A1 | 6/2015 | Hernandez et al. | |
| 2015/0182224 A1 | 7/2015 | Altman | |
| 2016/0022266 A1 | 1/2016 | Lukin et al. | |
| 2016/0235442 A1 | 8/2016 | Palese et al. | |
| 2016/0262761 A1 | 9/2016 | Beisel et al. | |
| 2016/0287257 A1 | 10/2016 | Fabian et al. | |
| 2016/0324523 A1 | 11/2016 | Lukin et al. | |
| 2016/0367236 A1 * | 12/2016 | Leeflang | A61M 25/0127 |
| 2016/0374683 A1 | 12/2016 | Gagner et al. | |
| 2017/0035425 A1 | 2/2017 | Fegelman et al. | |
| 2017/0265866 A1 | 9/2017 | Ryou et al. | |
| 2018/0028186 A1 | 2/2018 | Yamanouchi | |
| 2018/0028187 A1 | 2/2018 | Gagner et al. | |
| 2018/0193061 A1 | 7/2018 | Gittard et al. | |
| 2018/0214149 A1 | 8/2018 | Hunt et al. | |
| 2018/0214150 A1 | 8/2018 | Bakos et al. | |
| 2018/0214152 A1 | 8/2018 | Bakos et al. | |
| 2018/0263625 A1 | 9/2018 | Lukin et al. | |

(56) References Cited

U.S. PATENT DOCUMENTS

| | | |
|---|---|---|
| 2018/0296218 A1 | 10/2018 | Binmoeller et al. |
| 2018/0361127 A1 | 12/2018 | Gray et al. |
| 2019/0133587 A1 | 5/2019 | Gagner et al. |
| 2019/0133678 A1 | 5/2019 | Pate et al. |
| 2019/0183507 A1 | 6/2019 | Baillargeon |
| 2019/0216460 A1 | 7/2019 | Kopelman |
| 2019/0261998 A1 | 8/2019 | Altman et al. |
| 2019/0274687 A1 | 9/2019 | Wang et al. |
| 2020/0008834 A1 | 1/2020 | Cauche et al. |
| 2020/0129283 A1 | 4/2020 | Swensgard et al. |
| 2020/0138438 A1 | 5/2020 | Harrison et al. |
| 2020/0229968 A1* | 7/2020 | Galloway ............... A61F 9/007 |
| 2020/0246009 A1 | 8/2020 | Gagner et al. |
| 2020/0323530 A1 | 10/2020 | Sharma |
| 2021/0100554 A1 | 4/2021 | Seddon et al. |
| 2021/0161532 A1 | 6/2021 | Beisel et al. |
| 2021/0169485 A1 | 6/2021 | Beisel et al. |
| 2021/0169486 A1 | 6/2021 | Gagner et al. |
| 2021/0244414 A1 | 8/2021 | Lukin et al. |
| 2022/0087678 A1 | 3/2022 | Gagner et al. |

FOREIGN PATENT DOCUMENTS

| | | |
|---|---|---|
| EP | 1493391 B1 | 12/2009 |
| EP | 2207488 B1 | 9/2012 |
| EP | 2538852 A1 | 1/2013 |
| EP | 3267905 A1 | 1/2018 |
| EP | 2260752 B1 | 3/2018 |
| EP | 3573542 A1 | 12/2019 |
| EP | 3487418 A4 | 4/2020 |
| JP | 2006271832 A | 10/2006 |
| JP | 2008508939 A | 3/2008 |
| JP | 2011500159 A | 1/2011 |
| JP | 202198077 A | 7/2021 |
| RU | 2018266 C1 | 8/1994 |
| SU | 1708313 A1 | 1/1992 |
| SU | 1725851 A1 | 4/1992 |
| WO | 01/087398 A2 | 11/2001 |
| WO | 01/93920 A2 | 12/2001 |
| WO | 2009048954 A1 | 4/2009 |
| WO | 2011085006 A2 | 7/2011 |
| WO | 2011/103400 A1 | 8/2011 |
| WO | 2013009886 A1 | 1/2013 |
| WO | 2014055193 A1 | 4/2014 |
| WO | 2016082481 A1 | 6/2016 |
| WO | 2016/145414 A1 | 9/2016 |
| WO | 2018022180 A1 | 2/2018 |
| WO | 2018/138632 A1 | 8/2018 |
| WO | 2019077218 A1 | 4/2019 |
| WO | 2019232526 A1 | 12/2019 |
| WO | 2019232527 A1 | 12/2019 |
| WO | 2020/196336 A1 | 10/2020 |
| WO | 2021/207821 A1 | 10/2021 |
| WO | 2022/061117 A1 | 3/2022 |
| WO | 2022/132351 A1 | 6/2022 |

OTHER PUBLICATIONS

Gagner, M., "Duodeno-Ileal Anastomosis with Self-Assembling Magnets: Initial Concepts and Basis of This Operation", Obesity Surgery 32, 932-933 (2022).

International Search Report and Written Opinion of the International Searching Authority, Application No. PCT/US2019035202, dated Aug. 8, 2019, 6 pages.

International Search Report and Written Opinion of the International Searching Authority, Application No. PCT/US2022/25343, dated Jul. 18, 2022, 14 pages.

International Search Report and Written Opinion of the International Searching Authority, Application No. PCT/US2022/25353, dated Jun. 30, 2022, 12 pages.

International Search Report and Written Opinion of the International Searching Authority, for Application No. PCT/US2011/020229, dated Jun. 21, 2013, 6 pages.

International Search Report and Written Opinion of the International Searching Authority, for Application No. PCT/US2013/041641, dated Oct. 18, 2013, 4 pages.

International Search Report and Written Opinion of the International Searching Authority, for Application No. PCT/US2015/041498 dated Nov. 17, 2015.

International Search Report and Written Opinion of the International Searching Authority, for Application PCT/US2016/022209, dated May 30, 2016.

Invitation to Pay Additional Fees and, Where Applicable, Protest Fee, from the International Search Authority, Application No. PCT/US2022/025338, dated Jun. 23, 2022, 2 pages.

Invitation to Pay Additional Fees and, Where Applicable, Protest Fee, from the International Search Authority, Application No. PCT/US2022/025370, dated Jun. 24, 2022, 3 pages.

Japanese Office Action for Japanese Patent Application No. 2021-034336 dated Dec. 17, 2021, 3 pages.

Japanese Penultimate Office Action for Japanese Patent Application No. 2021-034336 dated Aug. 1, 2022, 9 pages.

Search Report and Written Opinion issued for Application No. PCT/US2016/031547 dated Oct. 18, 2016.

Supplementary Partial European Search Report for Application No. EP 13793804.9 dated Jan. 15, 2016, 9 pages.

* cited by examiner

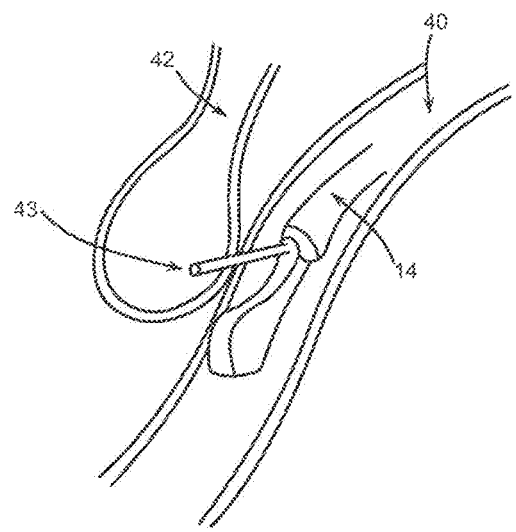
FIG. 21A
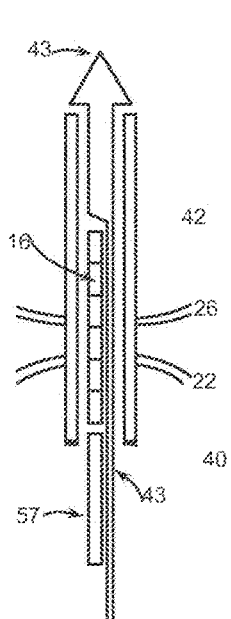 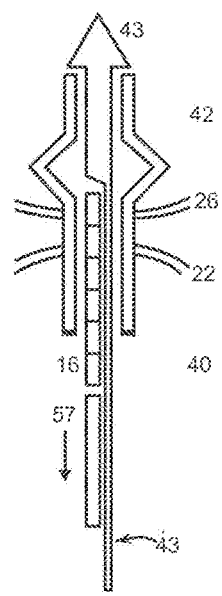 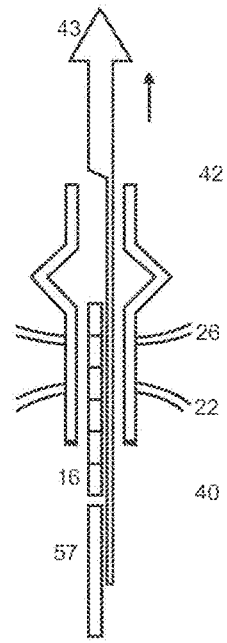
FIG. 21B    FIG. 21C    FIG. 21D

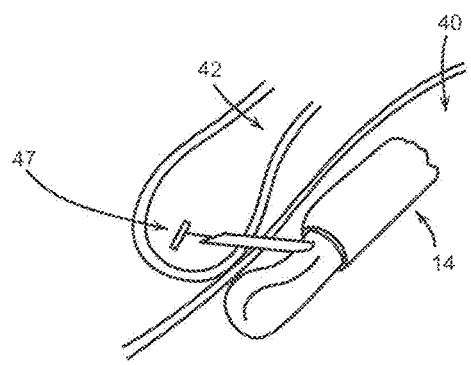
FIG. 25A
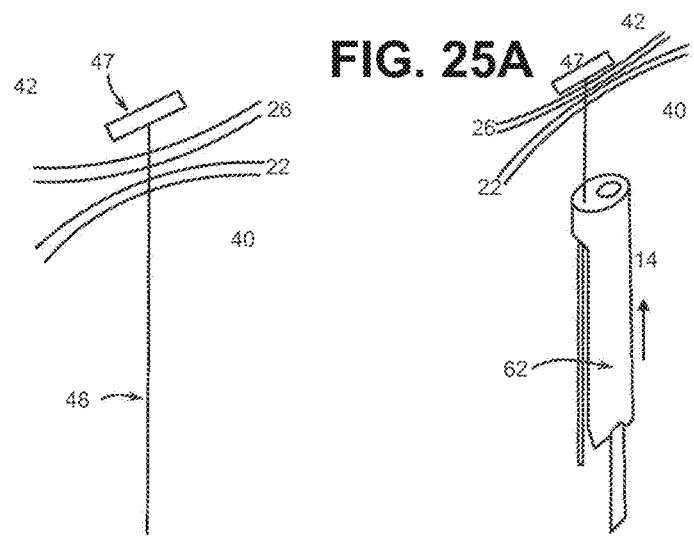
FIG. 25B  FIG. 25C

FIG. 45 Flexible Endoscopes General Diameter Guide for Endoscopy Brushes

| SCOPE TYPE | INSERTION TUBE OUTER DIAMETER | WORKING LENGTH | INSTRUMENT CHANNEL INTERNAL DIAMETER | HEALTHMARK ENDO BRUSHES | ENDOBRUSH DIAMETER RANGE | OLYMPUS COLOR GUIDE |
|---|---|---|---|---|---|---|
| ADULTS | | | | | | |
| GASTROSCOPE | 9.0 mm - 11.4 mm | 1030 mm - 1050 mm | 2.8mm - 3.8mm | CC-250, CC-374 | 2.6 - 3.2 mm, 3.7 - 4.3 mm | |
| DUODENSCOPE | 10.8 mm - 12.5 mm | 1235 mm - 1250 mm | 3.2mm - 4.2mm | CC-250, CC-374 | 2.6 - 3.2 mm, 3.7 - 4.3 mm | |
| COLONOSCOPE | 12.9 mm - 13.7 mm | 1330 mm - 1680 mm | 3.7mm - 4.2mm | CC-374 | 3.7 - 4.3 mm | |
| SIGMOIDOSCOPE | 12.8 mm - 13.2 mm | 700 mm - 730 mm | 3.7mm - 4.2mm | CC-374 | 3.7 - 4.3 mm | |
| ENTEROSCOPE | 10.5 mm - 11.7 mm | 2200 mm - 2500 mm | 2.8mm - 3.8mm | CC-250, CC-374 | 2.6 - 3.2 mm, 3.7 - 4.3 mm | |
| BRONCHOSCOPE | 5.7 mm - 6.0 mm | 550 mm - 600 mm | 2.0mm - 2.8mm | CC-172, CC-250 | 1.7 - 2.2 mm, 2.6 - 3.2 mm | |
| URETEROSCOPE | 2.8 mm - 3.3 mm | 670 mm - 700 mm | 1.2mm | CC-172 | 1.7 - 2.2 mm | |
| CYSTOSCOPE | 5.4 mm - 5.5 mm | 380 mm | 2.2mm - 2.4mm | CC-172, CC-250 | 1.7 - 2.2 mm, 2.6 - 3.2 mm | |
| RHINO-LARYNGOSCOPE | 2.6 mm - 4.9 mm | 300 mm - 365 mm | N/A - 2.0 | CC-172 | 1.7 - 2.2 mm | |
| LAPARO-THORACOSCOPE | 7.0 mm | 270 mm | 2.8 mm | CC-250 | 2.6 - 3.2 mm | |
| MOBILE AIRWAY SCOPE | 4.1 mm - 5.2 mm | 600 mm | 1.5 mm - 2.6 mm | CC-172, CC-250 | 1.7 - 2.2 mm, 2.6 - 3.2 mm | |
| CHOLEDOCHOSCOPE | 2.8 mm - 5.2 mm | 380 mm - 700 mm | 1.2 mm - 2.2 mm | CC-110, CC-172 | 1.2 mm, 1.7 - 2.2 mm | white |
| PEDIATRICS | | | | | | |
| GASTROSCOPE | 5.9 mm - 6.0 mm | 1030 mm - 1050 mm | 2.0 mm | CC-172 | 1.7 - 2.2 mm | |
| COLONOSCOPE | 11.5 mm - 11.6 mm | 1680 mm - 1700 mm | 3.2 mm - 3.8 mm | CC-250, CC-374 | 2.6-3.2 mm, 3.7 - 4.3 mm | |
| BRONCHOSCOPE | 4.4 mm - 5.1 mm | 600 mm | 2.0 mm | CC-172 | 1.7 - 2.2 mm | |

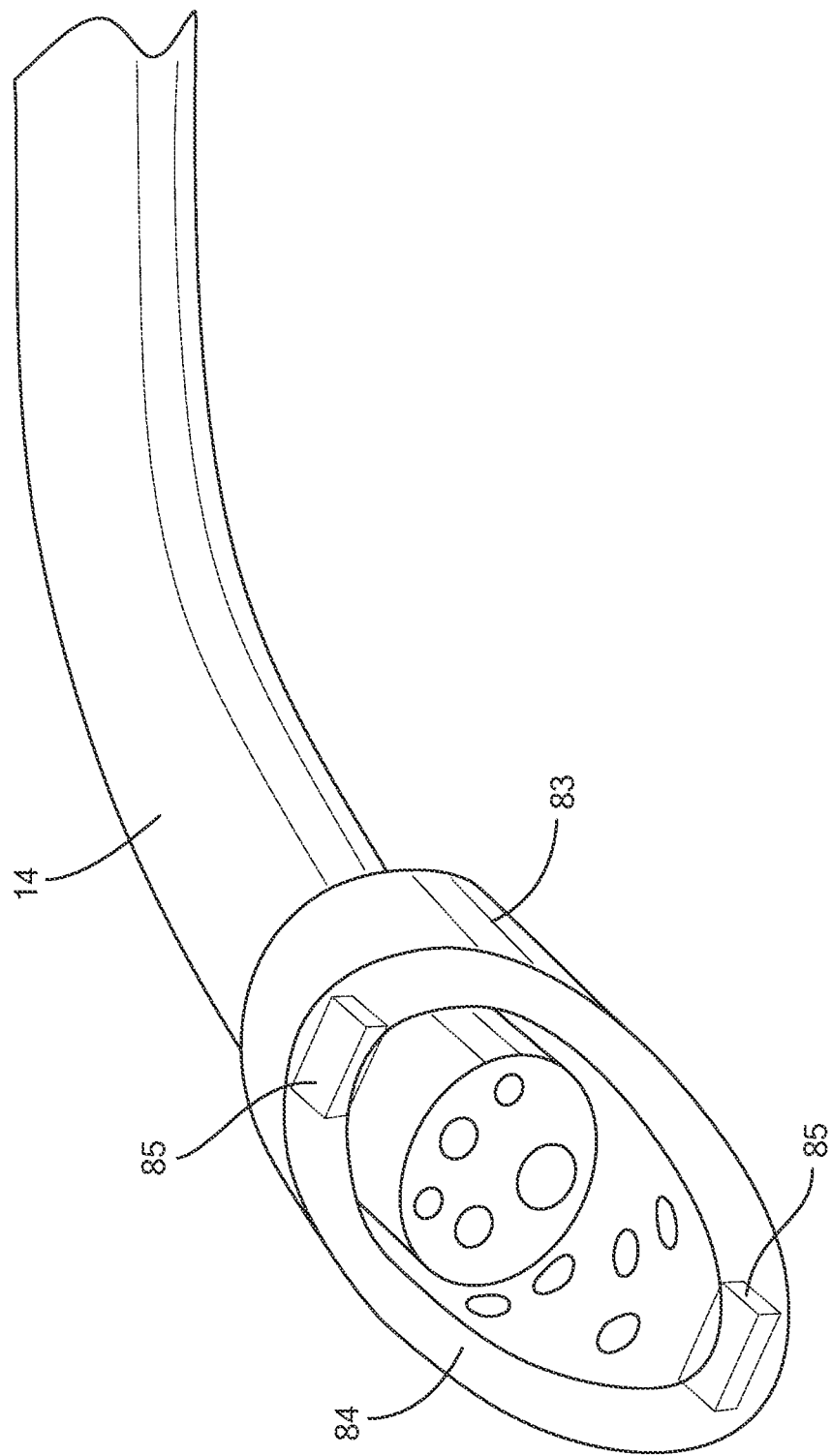

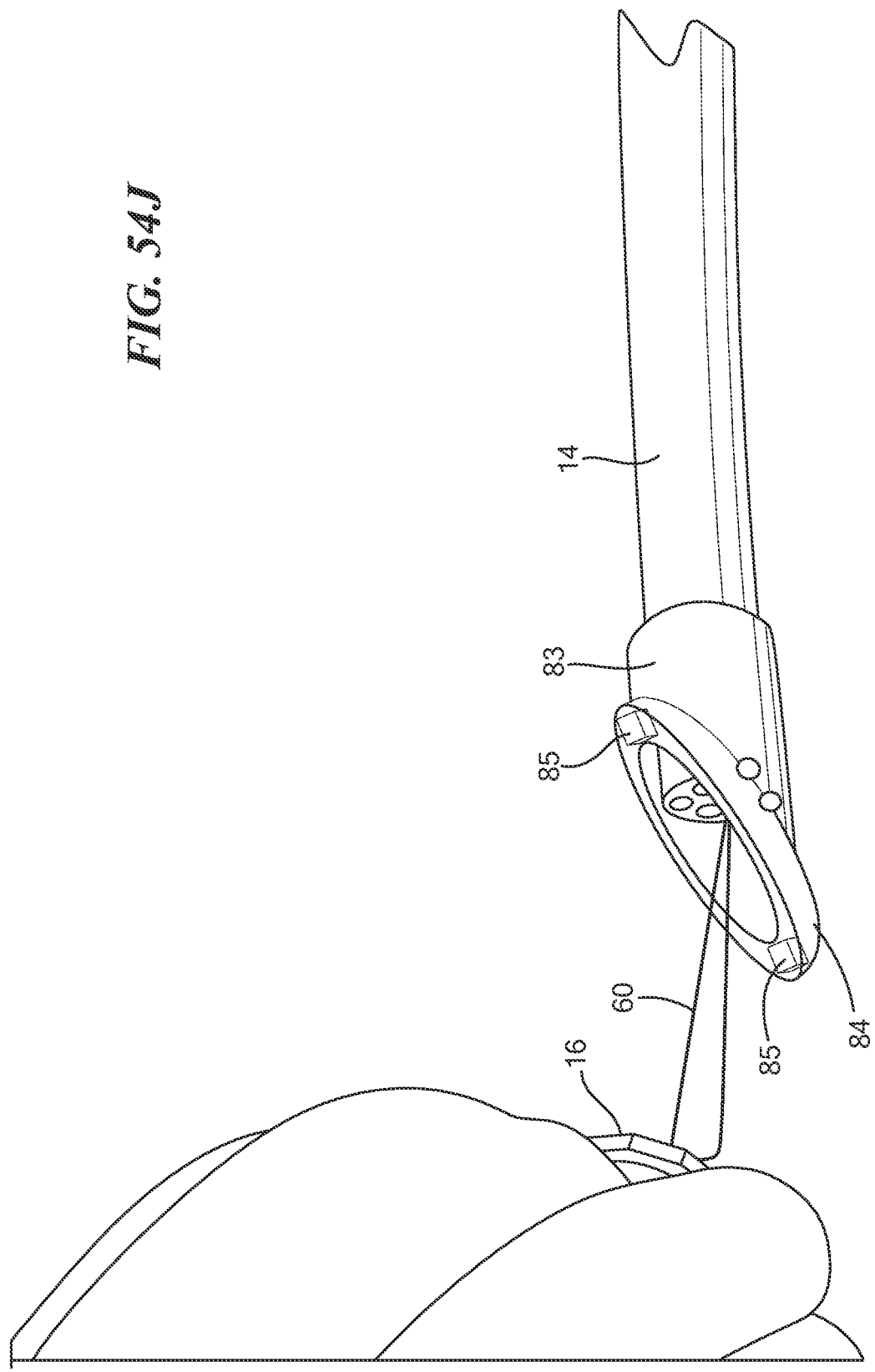

SYSTEMS, DEVICES, AND METHODS FOR ENDOSCOPE OR LAPAROSCOPIC MAGNETIC NAVIGATION

CROSS-REFERENCE TO RELATED APPLICATIONS

This application is a continuation of International Patent Application No. PCT/US2022/025343 entitled SYSTEMS, DEVICES, AND METHODS FOR ENDOSCOPE OR LAPAROSCOPIC MAGNETIC NAVIGATION filed Apr. 19, 2022, which claims the benefit of U.S. Provisional Patent Application No. 63/177,162 entitled SYSTEMS, DEVICES, AND METHODS FOR ENDOSCOPE OR LAPAROSCOPIC MAGNETIC NAVIGATION filed Apr. 20, 2021, each of which is hereby incorporated by reference herein in its entirety.

The subject matter of this patent application may be related to the subject matter of U.S. patent application Ser. No. 17/108,840 entitled SYSTEMS, DEVICES, AND METHODS FOR FORMING ANASTOMOSES filed Dec. 1, 2020, which is a continuation-in-part of, and therefore claims priority from, International Patent Application No. PCT/US2019/035202 having an International Filing Date of Jun. 3, 2019, which claims the benefit of, and priority to, U.S. Provisional Application Ser. No. 62/679,810, filed Jun. 2, 2018, U.S. Provisional Application Ser. No. 62/798,809, filed Jan. 30, 2019, and U.S. Provisional Application Ser. No. 62/809,354, filed Feb. 22, 2019, the contents of each of which are hereby incorporated by reference herein in their entireties.

FIELD OF THE INVENTION

The invention relates to deployable magnetic compression devices, and, more particularly, to systems, devices, and methods for the delivery, deployment, and positioning of magnetic compression devices at a desired site so as to improve the accuracy of anastomoses creation between tissues, organs, or the like.

BACKGROUND

Bypasses of the gastroenterological (GI), cardiovascular, or urological systems are typically formed by cutting holes in tissues at two locations and joining the holes with sutures or staples. A bypass is typically placed to route fluids (e.g., blood, nutrients) between healthier portions of the system, while bypassing diseases or malfunctioning tissues. The procedure is typically invasive, and subjects a patient to risks such as bleeding, infection, pain, and adverse reaction to anesthesia. Additionally, a bypass created with sutures or staples can be complicated by post-operative leaks and adhesions. Leaks may result in infection or sepsis, while adhesions can result in complications such as bowel strangulation and obstruction. While traditional bypass procedures can be completed with an endoscope, laparoscope, or robot, it can be time consuming to join the holes cut into the tissues. Furthermore, such procedures require specialized expertise and equipment that is not available at many surgical facilities.

As an alternative to sutures or staples, surgeons can use mechanical couplings or magnets to create a compressive anastomosis between tissues. For example, compressive couplings or paired magnets can be delivered to tissues to be joined. Because of the strong compression, the tissue trapped between the couplings or magnets is cut off from its blood supply. Under these conditions, the tissue becomes necrotic and degenerates, and at the same time, new tissue grows around points of compression, e.g., on the edges of the coupling. With time, the coupling can be removed, leaving a healed anastomosis between the tissues.

Nonetheless, the difficulty of placing the magnets or couplings limits the locations that compressive anastomosis can be used. In most cases, the magnets or couplings have to be delivered as two separate assemblies, requiring either an open surgical field or a bulky delivery device. For example, existing magnetic compression devices are limited to structures small enough to be deployed with a delivery conduit e.g., an endoscopic instrument channel or laparoscopic port. When these smaller structures are used, the formed anastomosis is small and suffers from short-term patency. Furthermore, placement of the magnets or couplings can be imprecise, which can lead to anastomosis formation in locations that is undesirable or inaccurate.

Thus, there still remains a clinical need for reliable devices and minimally-invasive procedures that facilitate compression anastomosis formation between tissues in the human body.

SUMMARY

Various embodiments of the invention provide improved devices and techniques for minimally-invasive formation of anastomoses within the body. Such devices and techniques facilitate faster and less-expensive treatments for chronic diseases such as obesity and diabetes. Such techniques also reduce the time and pain associated with palliative treatments for diseases such as cancers.

For example, in some embodiments, an apparatus for capturing and manipulating a compression anastomosis device comprises a cap configured to attach to a delivery device with an articulating cap facia coupled to the distal end of the cap body. In some embodiments, the cap facia may be moveable between a closed position and a fully opened position. Various embodiments may include one or more capture devices on the cap facia configured to capture a magnetic anastomosis device.

Various embodiments of the invention may include a cap facia that is angled substantially in relation to the delivery device. The fully opened cap facia may be pivoted away from the angled distal end of the delivery device. Some embodiments may include capture devices comprising magnets. In some embodiments, the magnets may be electromagnets providing a fixed magnetic field strength and/or a variable magnetic field strength for capturing, holding, and releasing a compression anastomosis device.

In some embodiments, the capture device may be capable of grasping or retaining the magnetic anastomosis device. The capture device may include one or more adhesive devices.

Various embodiments include a cap facia that may be coupled to the cap body using at least one pivot, wherein the pivot may include one or more pins and/or one or more hinge and/or one or more ball-and-socket joints.

In some embodiments, the cap may include a biasing system that biases the cap facia toward the closed position. The biasing system may include one or more springs.

The closed position of the cap facia may, in some embodiments, be less than or equal to approximately 45° relative to a nominal plane of the delivery device. The fully opened position may be greater than or equal to 90° relative to a nominal plane of the delivery device.

In some embodiments, the cap facia may include an extension that causes the cap facia to move from the closed position toward the fully opened position when pressure is applied to the extension. The cap facia may be configured to move from the closed position to the fully-opened position when a sufficient magnetic interaction force exists between a magnetic anastomosis device captured by the cap facia and an opposing magnetic anastomosis device.

Various embodiments may include an actuating mechanism for remotely controlling the position of the cap facia relative to the cap body, wherein the actuating mechanism may comprise a spring-loaded mechanism capable of releasing the cap facia from the closed position to the fully opened position. Various embodiments may include an actuating mechanism for remotely controlling the position of the cap body relative to the delivery device.

In some embodiments, the cap body is moveable relative to the delivery device. The cap body may include a universal joint, hinge, and/or ball-and-socket joint to be moveable relative to the delivery device, In some embodiments, the cap may comprise at least one sensor to sense the position of the cap body and provide feedback to a user.

The cap may be formed of a substantially clear material to permit viewing through the cap. The cap facia may have a diameter greater than that of the cap body. The cap body may include one or more channels extending through the cap body.

In some embodiments, the at least one channel is adapted for passing fluid and/or air through the cap body, the at least one channel is adapted for passing an instrument through the cap body, the at least one channel is adapted for allowing visibility through the cap body, and/or the at least one channel is adapted for delivering suction through the cap body.

Various embodiments include at least one capture device configured to automatically release the captured magnetic anastomosis device when the captured magnetic anastomosis device is properly mated with an opposing magnetic anastomosis device, and to retain the captured magnetic anastomosis device when the captured magnetic anastomosis device is insufficiently mated with an opposing magnetic anastomosis device.

In some embodiments, the delivery device is attached to the cap. The delivery device in some embodiments may be an endoscope, a laparoscope, or a catheter.

BRIEF DESCRIPTION OF THE DRAWINGS

Features and advantages of the claimed subject matter will be apparent from the following detailed description of embodiments consistent therewith, which description should be considered with reference to the accompanying drawings.

FIG. 9 illustrates the use of monopolar energy for piercing and accessing the gallbladder.

FIG. 10 illustrates the use of a fine aspiration needle (FNA) for piercing and accessing the gallbladder.

FIG. 11 illustrates the use of a corkscrew-type needle for piercing and accessing the gallbladder.

FIG. 12 illustrates the use of a guidewire passed through the bile duct.

FIG. 14 illustrates a T-bar member. FIG. 15 illustrates a nitinol coil (e.g., "pig tail"). FIG. 16 illustrates a balloon member of a catheter. FIG. 17 illustrates a malecot catheter.

FIGS. 21A, 21B, 21C, 21D, and 21E illustrate a technique of accessing the gallbladder and delivering a pair of magnetic anastomosis devices for the formation of an anastomosis the gallbladder tissue and adjacent tissue.

FIGS. 25A, 25B, 25C, 25D, 25E illustrate a technique of accessing the gallbladder and delivering a pair of magnetic anastomosis devices for the formation of an anastomosis between the gallbladder tissue and adjacent tissue (i.e., stomach or duodenum tissue).

FIG. 45 provides a listing of some exemplary working channel sizes considered usable/feasible to deploy a magnetic array with a cage to produce an anastomosis.

FIGS. 54A-54J show an exemplary flexible and manipulable delivery device having an angled cap for selectively delivering, capturing, and releasing a magnetic compression anastomosis device, in accordance with one exemplary embodiment.

Figure 1:
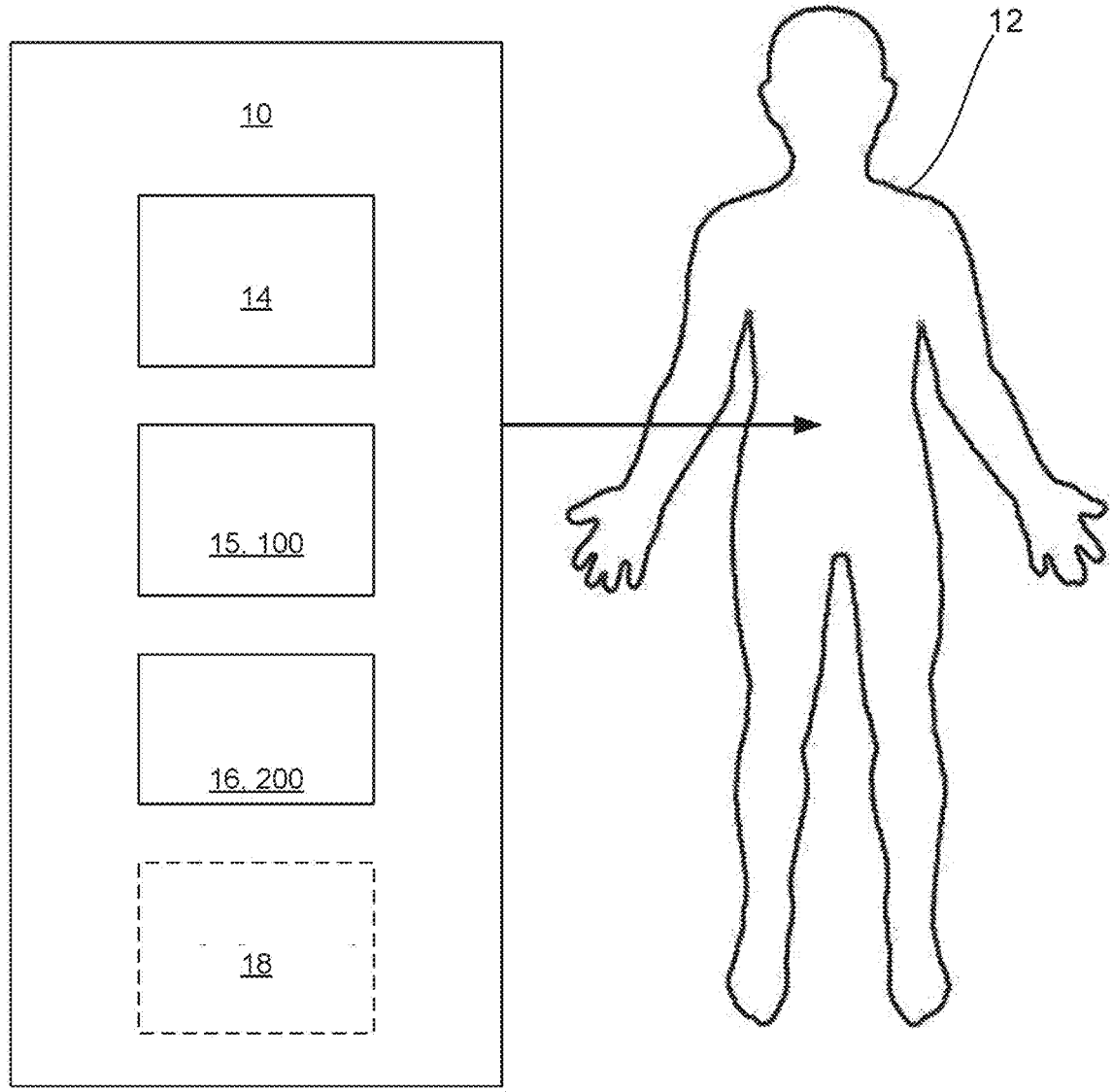
FIG. 1 is a schematic illustration of an anastomosis formation system consistent with the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

Exemplary embodiments provide improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as stomach or colon cancer.

The system generally includes an access device configured to be provided within a hollow body of a patient and assist in the formation of an anastomosis at a target site (a desired anatomical location) within the hollow body for formation of an anastomosis between a first portion of tissue of the hollow body at the target site and a second portion of tissue of the hollow body. The access device is configured to provide access to the first and second portions of tissue of the hollow body and further deliver and position first and second implantable magnetic anastomosis devices relative to the first and second portions of tissue or adjacent tissue for the formation of an anastomosis between tissues at the target site. The first and second implantable magnetic anastomosis devices are configured to be magnetically attracted to one another through a defined tissue area of the combined thickness of a wall of the tissues at the target site and exert compressive forces on the defined area to form the anastomosis.

The systems, devices, and methods described herein include, but are not limited to, various access devices for accessing a hollow body of the patient, such as a gallbladder, and securing positioning of the access device for the subsequent placement of one of a pair of magnetic anastomosis compression devices. The systems, devices, and methods described herein further include various delivery devices for delivering at least one of the pair of magnetic anastomosis compression devices to the target site, wherein, in some instances, a delivery device consistent with the present disclosure may assist in the deployment of at least one of the pair of magnetic anastomosis compression devices and subsequent securing to the target site and/or coupling the pair of magnetic anastomosis compression devices to one another. The systems, devices, and methods described herein include various embodiments of magnetic anastomosis compression devices and various designs for transitioning from a compact delivery configuration to a larger deployed configuration, generally by way of self-assembling design.

More specifically, exemplary embodiments provide a system including a delivery device for introducing and delivering, via a minimally-invasive technique, a pair of magnetic assemblies between adjacent organs to bridge walls of tissue of each organ together to thereby form a passage therebetween (i.e., an anastomosis). The delivery device is particularly useful in delivering the pair of magnetic assemblies to a target site within the gastrointestinal tract to thereby form anastomosis between gastric and gallbladder walls to provide adequate drainage from the gallbladder when blockage is occurring (due to disease or other health-related issues).

Delivery devices of exemplary embodiments may include an anastomosis capture device, comprising a cap for an endoscopic or laparoscopic delivery device. The cap is capable of magnetically engaging the magnetic anastomosis device in order to control and mate it to another anastomosis device, forming a pair in order to create an anastomosis between tissues. The capture device is articulable and able to pivot relative to the endoscope in order to engage, control, and release the anastomosis device.

Accordingly, exemplary embodiments provide improved devices and techniques for minimally invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

FIG. 1 is a schematic illustration of an anastomosis formation system 10 for providing improved placement of magnetic anastomosis devices at a desired site so as to improve the accuracy of anastomoses creation between tissues within a patient 12. The system 10 generally includes an access device 14, a delivery device 15, 100, magnetic anastomosis devices 16, 200, and an imaging modality 18.

The access device 14 may generally include a scope, including, but not limited to, an endoscope, laparoscope, catheter, trocar, or other delivery device. For most applications described herein, the access device 14 is an endoscope, including a delivery needle configured to deliver the magnetic anastomosis devices 16, 200. Accordingly, the system 10 of the present disclosure relies on a single endoscope 14 for the delivery of the two magnetic devices 16, 200. As will be described in greater detail herein, a surgeon may advance the endoscope 14 within a hollow body of the patient 12 and position the endoscope 14 at the desired anatomical location for formation of the anastomosis based on a visual depiction of the location of the target site as provided by an imaging modality 18. For example, the imaging modality 18 may include a display in which an image, or other visual depiction, is displayed to the surgeon illustrating a target site when performing a medical imaging procedure, including, but not limited to, ultrasound (US), wavelength detection, X-ray-based imaging, illumination, computed tomography (CT), radiography, and fluoroscopy, or a combination thereof. The surgeon may then rely on such a visual depiction when advancing the endoscope 14 through the hollow body so as to position the access device 14 at a portion of tissue adjacent to the other portion of tissue at the target site, thereby ensuring the placement of the magnetic devices 16, 200 is accurate.

It should be noted that the hollow body through which the access device 14 may pass includes, but is not limited to, the stomach 40, gallbladder 42, pancreas, duodenum 41, small intestine, large intestine, bowel, vasculature, including veins and arteries, or the like.

In some embodiments, self-assembling magnetic devices 16 are used to create a bypass in the gastrointestinal tract. Such bypasses can be used for the treatment of a cancerous obstruction, weight loss or bariatrics, or even treatment of diabetes and metabolic disease (i.e. metabolic surgery).

Figure 2:
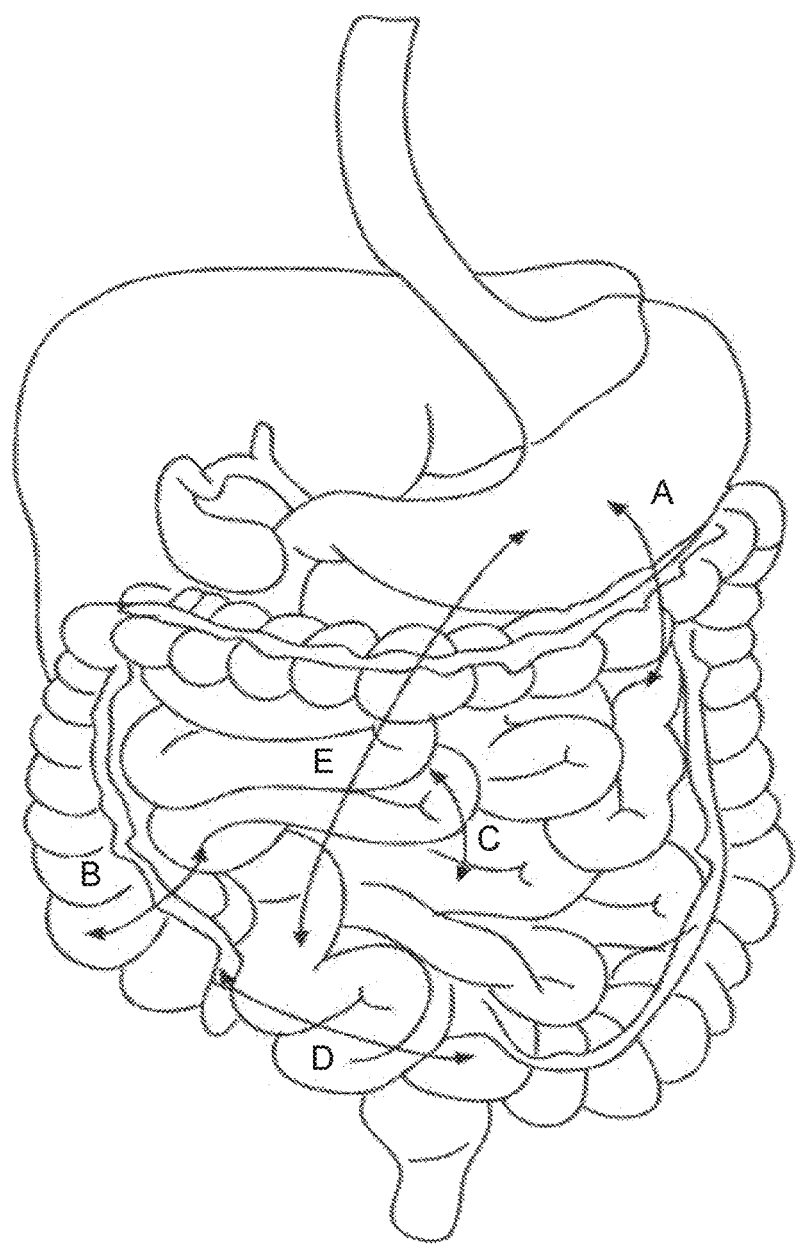
FIG. 2 shows several potential anatomical targets for anastomosis formation, where arrow A is stomach to small intestine, arrow B is small intestine to large intestine, arrow C is small intestine to small intestine, arrow D is large intestine to large intestine, and arrow E is stomach to large intestine.

FIG. 2 illustrates the variety of gastrointestinal anastomotic targets that may be addressed with the devices of certain exemplary embodiments, such targets include stomach to small intestine (A), stomach to large intestine (E), small intestine to small intestine (C), small intestine to large intestine (B), and large intestine to large intestine (D). Accordingly, exemplary embodiments provide improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as stomach or colon cancer.

For example, if the hollow body through which the access device 14 may pass is a bowel of the patient, the first portion may be a distal portion of the bowel and the second portion may be a proximal portion of the bowel. The bowel includes any segment of the alimentary canal extending from the pyloric sphincter of the stomach to the anus. In some embodiments, an anastomosis is formed to bypass diseased, mal-formed, or dysfunctional tissues. In some embodiments, an anastomosis is formed to alter the "normal" digestive process in an effort to diminish or prevent other diseases, such as diabetes, hypertension, autoimmune, or musculoskeletal disease. It should be noted that the system may be used for the formation of an anastomosis between a first portion of tissue of the hollow body at the target site and an adjacent tissue of a second hollow body (e.g., portal between the stomach and the gallbladder, the duodenum and the gallbladder, stomach to small intestine, small intestine to large intestine, stomach to large intestine, etc.).

Figure 3:
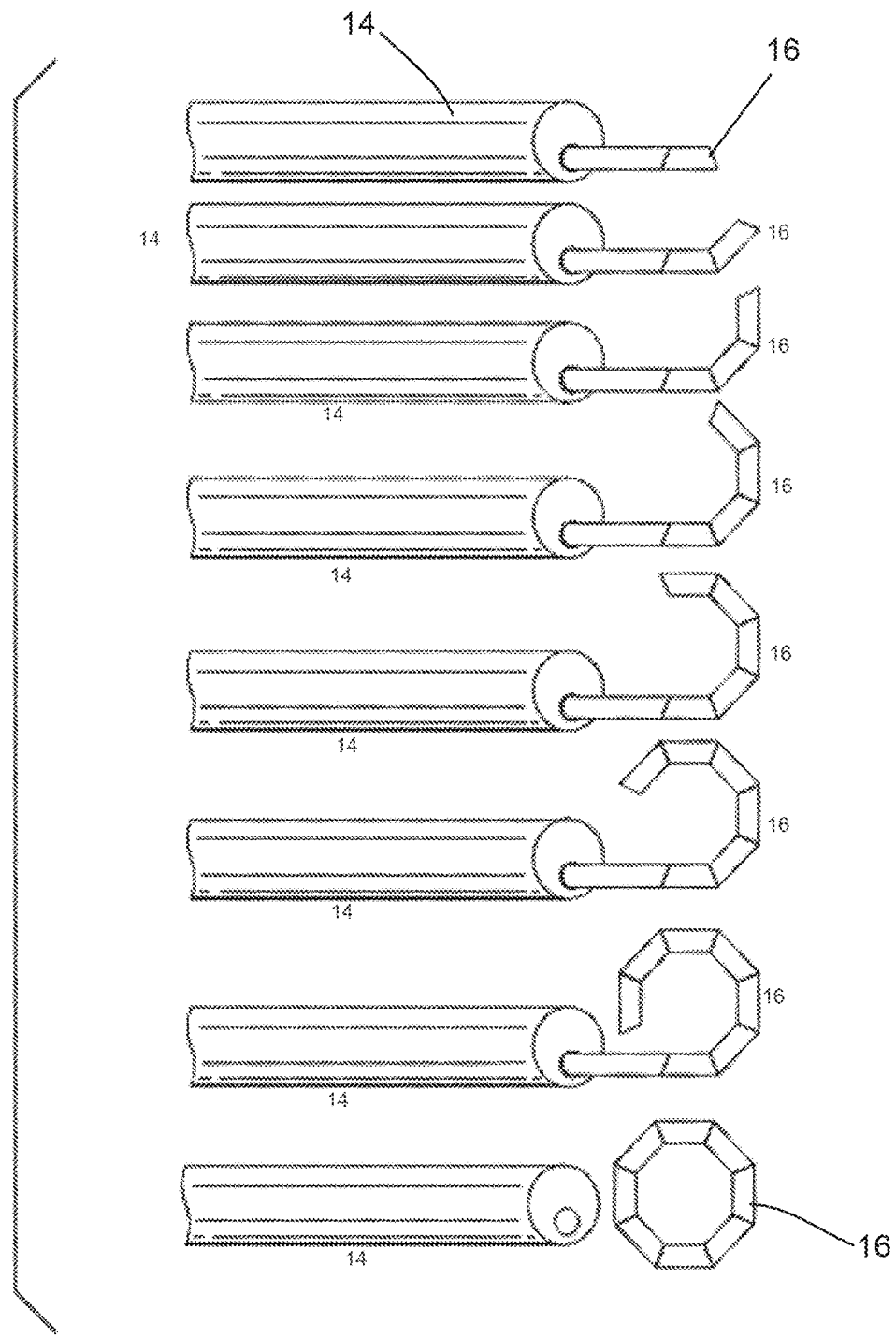
FIG. 3 shows an exemplary magnetic anastomosis device delivered through an endoscope instrument channel such that the individual magnet segments self-assemble into a larger magnetic structure—in this particular case, an octagon.

In an endoscopic procedure, the self-assembling magnetic devices 16 can be delivered using a single endoscope 14. Deployment of a magnetic device 16 is generally illustrated in FIG. 3. As shown, exemplary magnetic anastomosis devices 16 may be delivered through an endoscope 14 such that individual magnet segments self-assemble into a larger magnetic structure—in this particular case, an octagon. When used with the techniques described herein, the devices 16 allow for the delivery of a larger magnetic structures than would otherwise be possible via a small delivery conduit, such as in a standard endoscope, if the devices were deployed as a completed assembly. Larger magnet structures, in turn, allow for the creation of larger anastomoses that are more robust, and achieve greater surgical success. For example, in some cases, resulting anastomosis may have a 1:1 aspect ratio relative to the final dimensions of the assembled magnetic devices. However, exemplary embodiments allow for larger aspect ratios (i.e., a larger anastomosis to form relative to the dimensions of the magnetic assemblies). In particular, prior art systems and methods that include the use of magnets for creating anastomosis are generally limited based on the dimensions of the working channel of the scope or catheter used for delivering such magnets, which, in turn, limits the resulting size of the anastomosis. However, the magnetic assembly design of exemplary embodiments overcome such limitations. For example, the design of the magnetic assembly, notably the coupling of multiple magnetic segments to one another via an exoskeleton, allow for any number of segments to be included in a single assembly, and thus the resulting anastomosis has a greater size relative to the dimensions of the working channel of the scope. For example, in some embodiments, the resulting anastomosis may include an aspect ratio in the range of 2:1 to 10:1 or greater. Such aspect ratios are described in greater detail with regard to FIGS. 44A, 44B, 44C, and 44D.

Because the magnetic devices 16 are radiopaque and echogenic, the devices 16 can be positioned using fluoroscopy, direct visualization (trans-illumination or tissue indentation), and ultrasound, e.g., endoscopic ultrasound. The devices 16 can also be ornamented with radiopaque paint or other markers to help identify the polarity of the devices during placement.

The magnetic anastomosis devices 16 generally comprise magnetic segments 200 that can assume a delivery conformation and a deployed configuration. The delivery configuration is typically linear so that the device can be delivered to a tissue via a laparoscopic "keyhole" incision or with delivery via a natural pathway, e.g., via the esophagus, with an endoscope 14 or similar device. Additionally, the delivery conformation is typically somewhat flexible so that the device 16 can be guided through various curves in the body. Once the device 16 is delivered, the device 16 will assume a deployed configuration of the desired shape and size by converting from the delivery configuration to the deployed configuration automatically. The self-conversion from the delivery configuration to the deployment configuration is directed by coupling structures 30 that cause the magnetic segments to move in the desired way without intervention. Exemplary self-assembling magnetic anastomosis devices 16, such as self-closing, self-opening, and the like, are described in U.S. Pat. Nos. 8,870,898, 8,870,899, 9,763,664, and 10,182,821, the contents of each of which are incorporated by reference herein in their entirety.

Figure 4A:
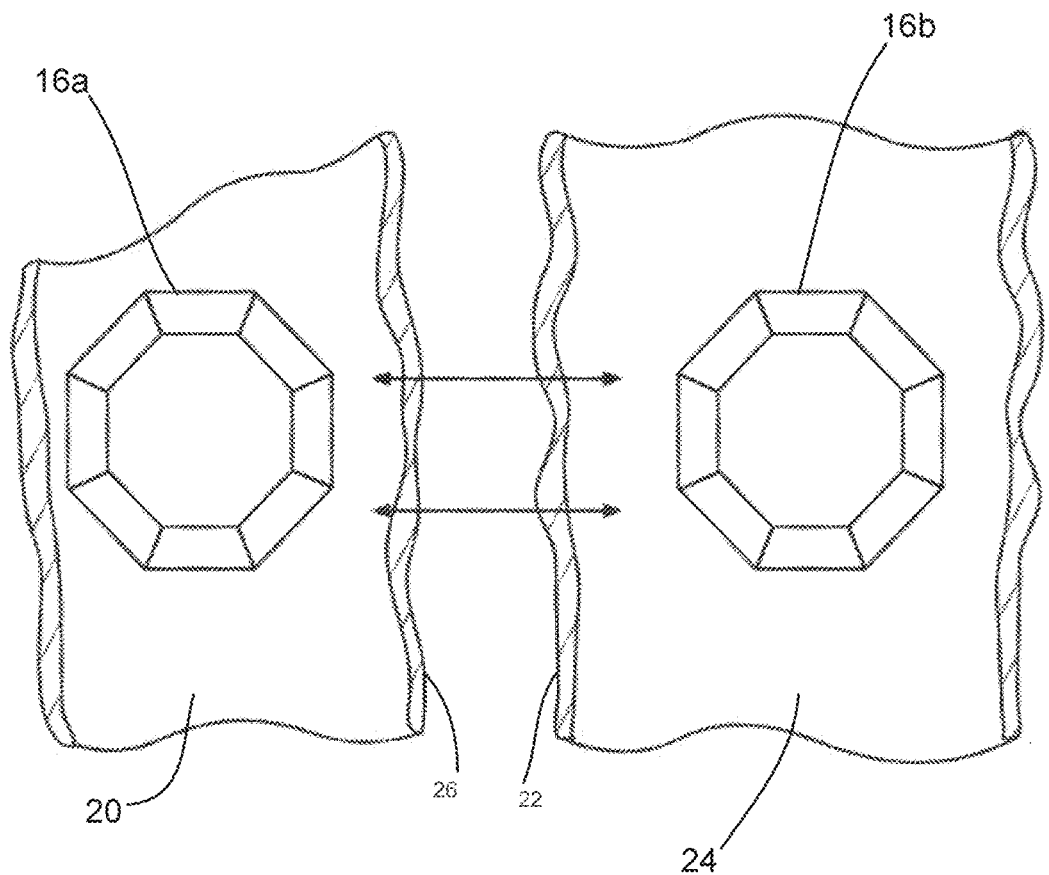
FIG. 4A depicts two magnetic anastomosis devices attracting each other through tissue. As shown, the devices each comprise eight magnetic segments, however alternate configurations are possible. Once the two devices mate, the tissue that is trapped between the devices will necrose, causing an anastomosis to form. Alternatively, the tissue bound by the devices may be perforated after the devices mate to create an immediate anastomosis.

In general, as shown in FIG. 4A, a magnetic anastomosis procedure involves placing a first and a second magnetic structures 16a, 16b adjacent to first and second portions 20, 24 of tissues 26, 22, respectively, thus causing the tissues 22 and 26 to come together. Once the two devices 16a, 16b are brought into proximity, the magnetic structures 16a, 16b mate and bring the tissues 22, 26 together. With time, an anastomosis of the size and shape of the devices 16a, 16b will form and the devices will fall away from the tissue. In particular, the tissues 22, 26 circumscribed by the devices will be allowed to necrose and degrade, providing an opening between the tissues.

Figure 4B:
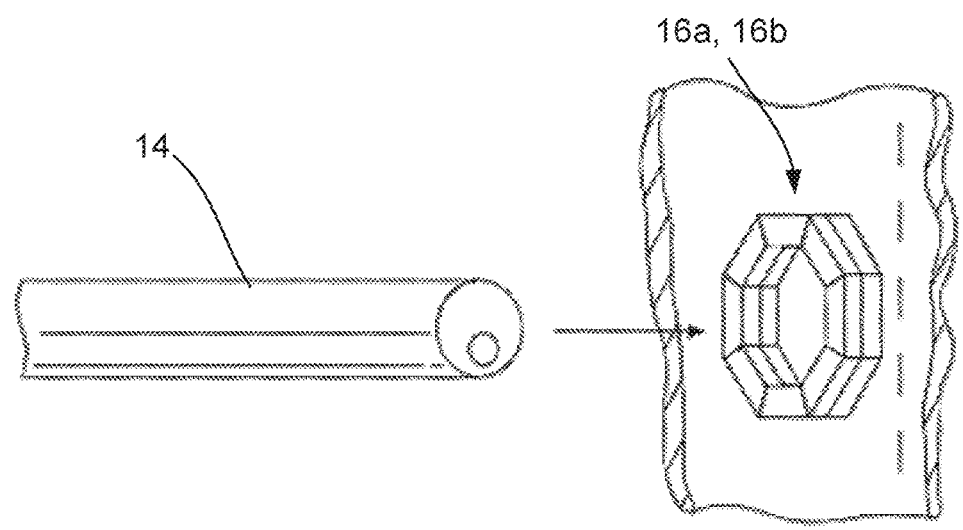
FIG. 4B shows the two magnetic anastomosis devices coupled together by magnetic attraction, capturing the intervening tissue. In some instances, the endoscope can be used to cut through the circumscribed tissue.

Alternatively, because the mated devices 16a and 16b create enough compressive force to stop the blood flow to the tissues 22, 26 trapped between the devices, a surgeon may create an anastomosis by making an incision in the tissues 22, 26 circumscribed by the devices, as shown in FIG. 4B.

In yet another embodiment, as will be described in greater detail herein, and shown in FIGS. 43A-43I, a surgeon may first cut into, or pierce, the tissues 22, 26, and then deliver a magnetic device 16a, 200a into a portion 20 of the hollow body so as to place device 16a, 200a around the incision on tissue 22. The surgeon may then place device 16b, 200b into portion 24 of the hollow body so as to deliver device 16b, 200b around the incision on tissue 26, and then allow the devices 16a, 200a and 16b, 200b to couple to one another, so that the devices 16a, 16b (200a, 200b) circumscribe the incision. As before, once the devices 16a, 16b (200a, 200b) mate, the blood flow to the incision is quickly cut off.

While the figures and structures of the disclosure are primarily concerned with annular or polygonal structures, it is to be understood that the delivery and construction techniques described herein can be used to make a variety of deployable magnetic structures. For example, self-assembling magnets can re-assemble into a polygonal structure such as a circle, ellipse, square, hexagon, octagon, decagon, or other geometric structure creating a closed loop. The devices may additionally include handles, suture loops, barbs, and protrusions, as needed to achieve the desired performance and to make delivery (and removal) easier. Yet still, in other embodiments, such as magnetic assembly 200 of FIG. 42, a magnetic assembly may comprise a pair of magnetic segments 202, 204 generally arranged in a linear alignment with one another (e.g., aligned in an end-to-end fashion) and coupled together via a flexible exoskeleton 206 element. Such an embodiment will be described in greater detail herein.

Figure 5A:
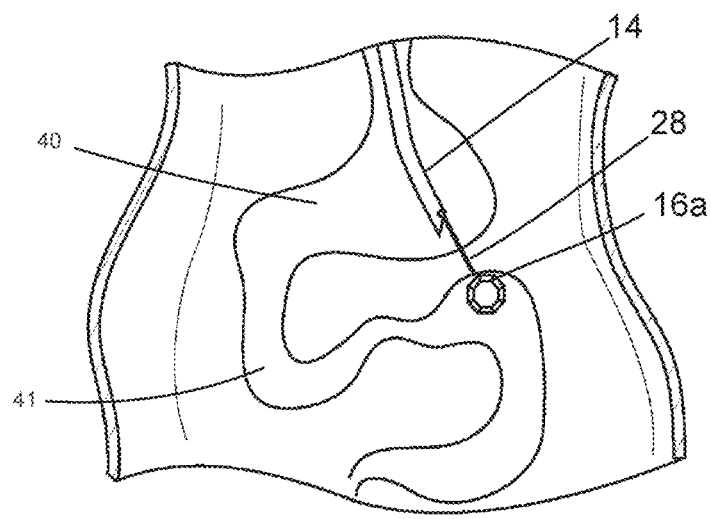
FIG. 5A shows the needle delivering a first magnetic device into a first portion of the hollow body at the target site.
Figure 5B:
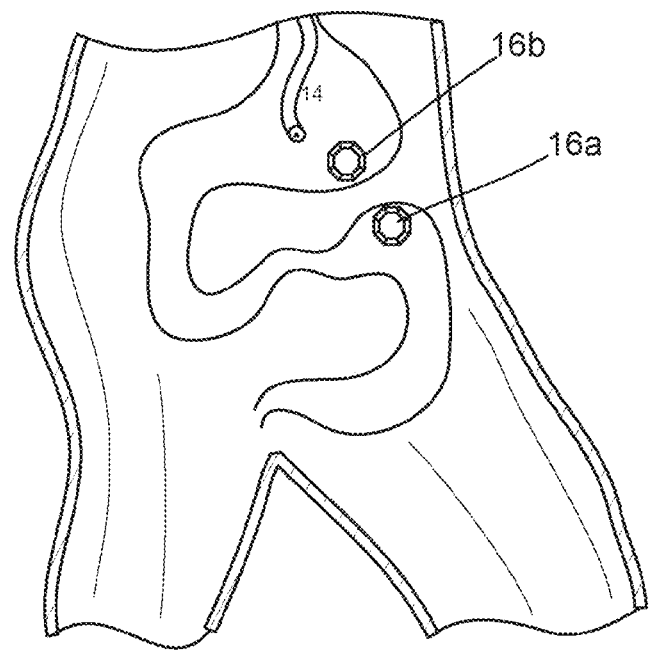
FIG. 5B shows subsequent deployment to of a second magnetic device into a second portion of the hollow body adjacent to the target site.

As previously described, the self-assembling magnetic anastomosis devices 16 can be delivered to the target site via the access device 14. For example, as shown in FIG. 5A, the access device 14 may include a delivery needle 28 (e.g., an aspiration needle) used to deliver the first magnetic anastomosis device 16a into the lower small intestine (through the puncture), which is then followed by deployment to of a second magnetic device 16b into the upper small intestine at a location on the tissue adjacent to the target site (shown in FIG. 5B). It should be noted that the delivery can be guided with fluoroscopy or endoscopic ultrasound. Following self-assembly, these small intestine magnetic devices 16a, 16b couple to one another (e.g., magnetically attracted to one another) through a defined tissue area of the combined thickness of a wall of the tissues at the target site and exert compressive forces on the defined area to form the anastomosis.

Figure 6A:
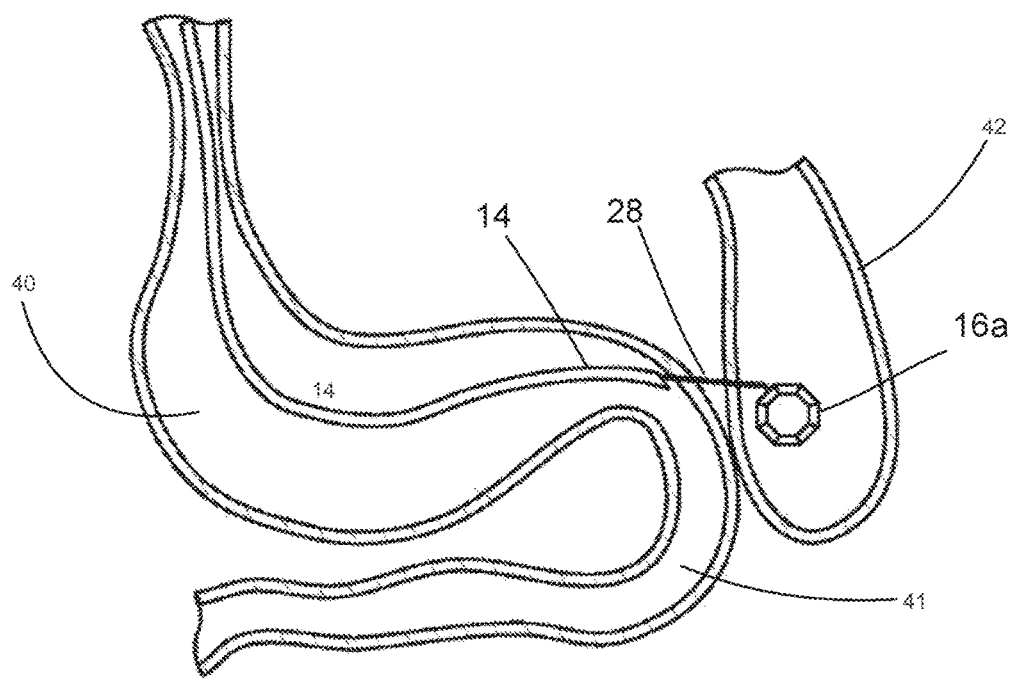
FIG. 6A shows endoscopic ultrasound guided needle delivery of a magnet assembly into the gallbladder which then couples with a second magnet assembly in the stomach or duodenum as shown in FIG. 6B.
Figure 6B:
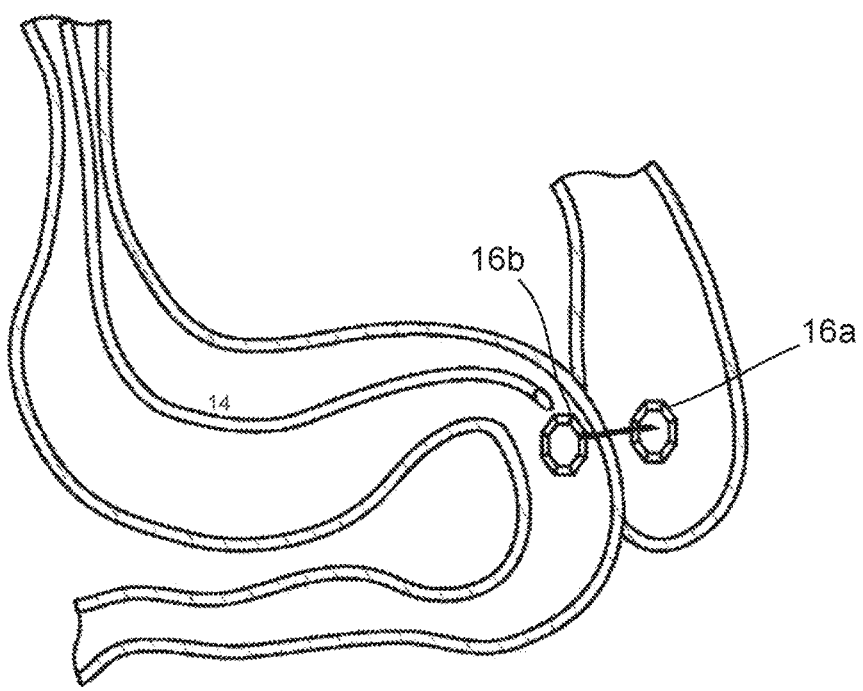

FIG. 6A shows endoscopic ultrasound guided needle 14 delivery of a magnet assembly 16a into the gallbladder 42 which then couples with a second magnet assembly 16b in the stomach 40 or duodenum 41 as shown in FIG. 6B. Accordingly, the described procedures may also be used with procedures that remove or block the bypassed tissues. For example, endoscopic ultrasound (EUS) 14 can be used to facilitate guided transgastric or transduodenal access into the gallbladder 42 for placement of a self-assembling magnetic anastomosis device 16. Once gallbladder 42 access is obtained, various strategies can be employed to maintain a patent portal between the stomach 40 and the gallbladder 42 or the duodenum 41 and the gallbladder 42. In another embodiment, gallstones can be endoscopically retrieved and fluid drained. For example, using the described methods, an anastomosis can be created between the gallbladder 42 and the stomach 40. Once the gallbladder 42 is accessed in a transgastric or transduodenal fashion, the gallstones can be removed. Furthermore, the gallbladder mucosa can be ablated using any number of modalities, including but not limited to argon plasma coagulation (APC), photodynamic therapy (PDT), sclerosant (e.g. ethanolamine or ethanol).

Figure 7:
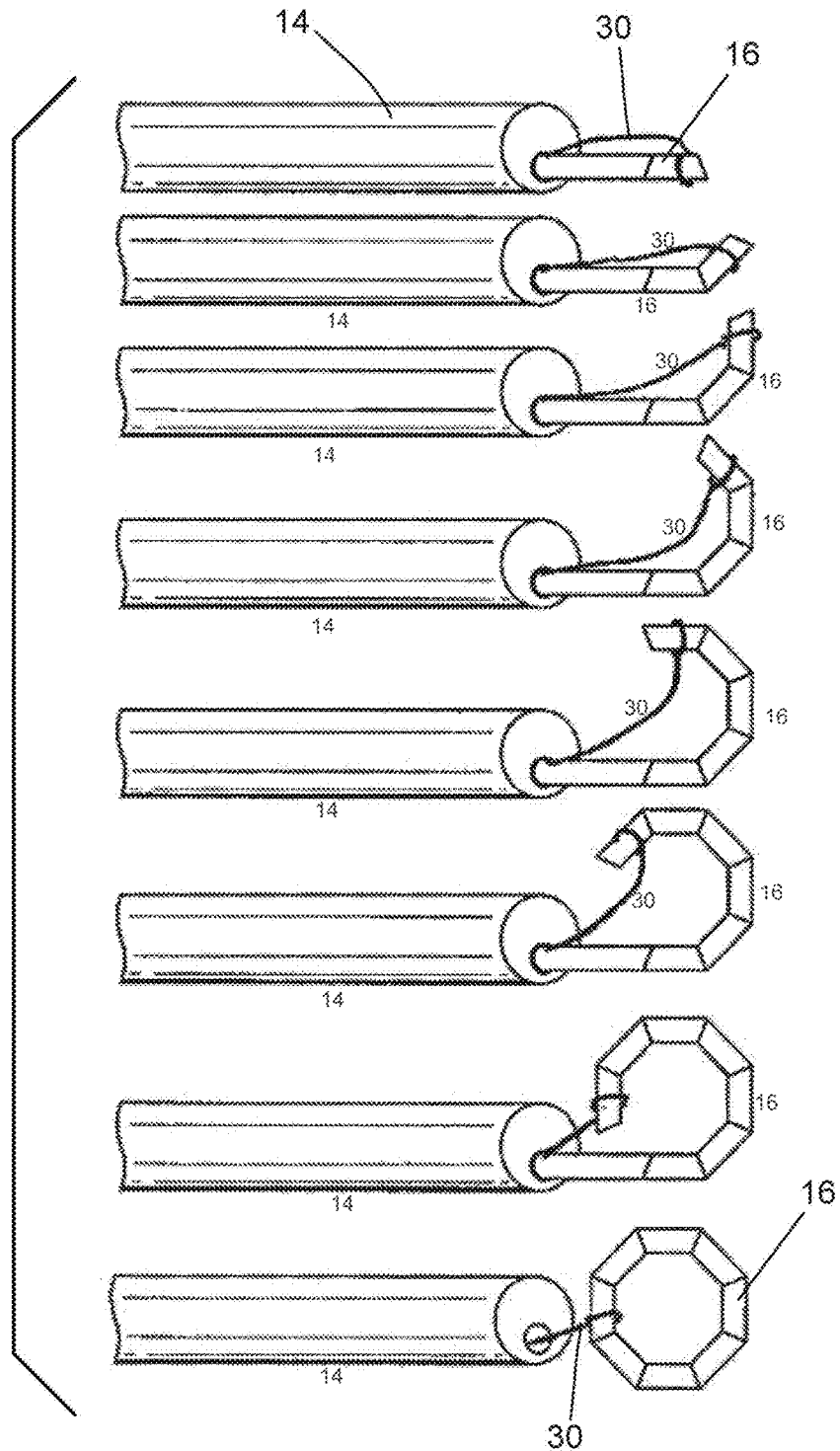
FIG. 7 illustrates a single guide element for deploying and manipulating a magnetic anastomosis device.
Figure 8A:
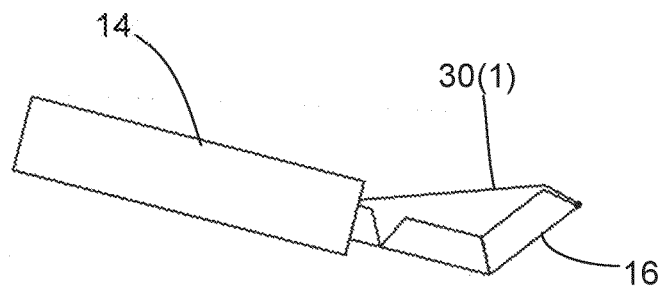
FIGS. 8A, 8B, 8C, 8D, 8E, and 8F each depict the deployment of the self-closing magnetic anastomosis device with a plurality of guide elements.
Figure 8B:
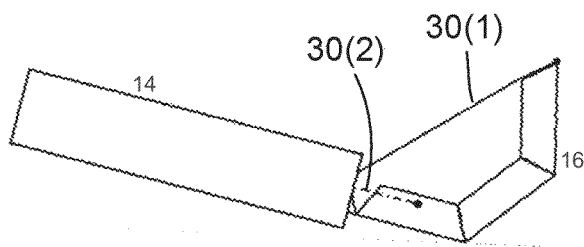
Figure 8C:
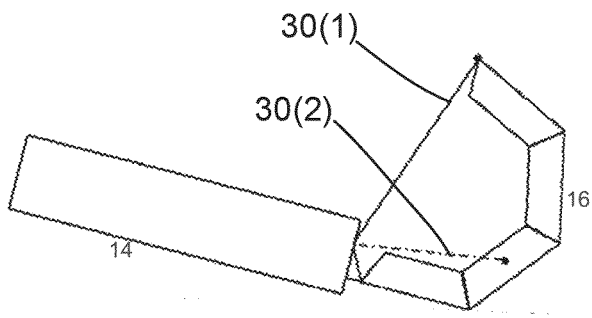
Figure 8D:
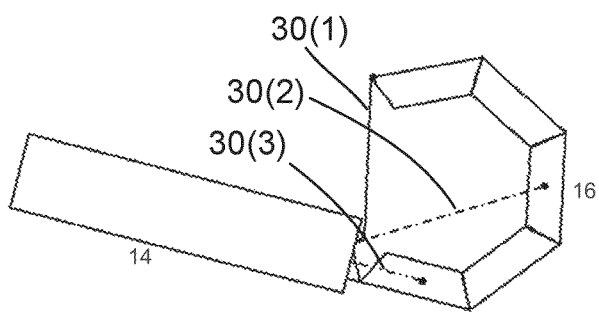
Figure 8E:
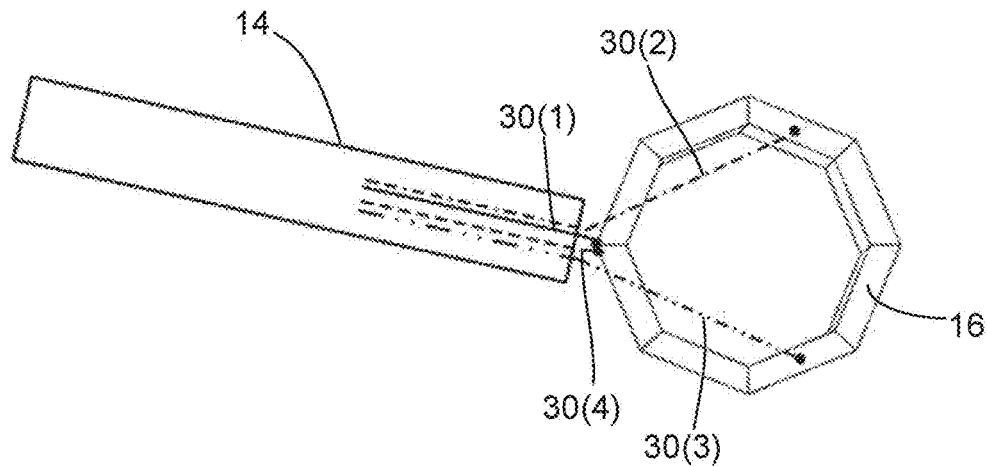
Figure 8F:
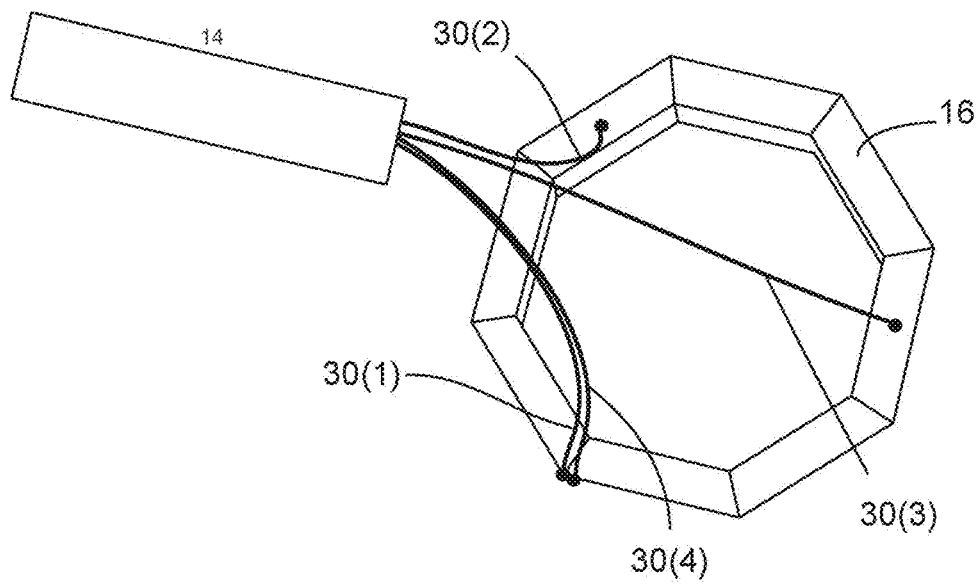

FIG. 7 illustrates a single guide element 30 for deploying and manipulating a magnetic anastomosis device 16. For example, once the self-assembling magnetic device 16 has been delivered to a tissue, it is beneficial to be able to manipulate the location of the device 16. While the device 16 can be manipulated with conventional tools such as forceps, it is often simpler to manipulate the location of the deployed device 16 with a guide element 30, such as a suture or wire. As shown in FIGS. 7 and 8A-8F, a variety of attachment points can be used to provide control over the location and deployment of a self-assembling magnetic anastomosis device 16. For example, as shown in FIG. 7, the guide element 30 may be coupled to a single distal segment such that, upon self-assembly, the single distal segment results in an attachment point that provides translational freedom of movement. It is also notable that the configuration shown in FIG. 7 also allows a closing force to be applied to the distal-most segment. That is, in the event that one or more segments should become entangled with tissue, or otherwise prevented from self-assembling, a proximal pulling force with the guide element 30 can help the device 16 to complete self-assembly. Once self-assembly is completed, the device 16 can be positioned with the guide element 30 to be mated with another device (not shown) to form an anastomosis, as described above. While it is not shown in FIG. 7, it is envisioned that additional structures, such as a solid pusher or a guide tube can be used to deploy the device 16 in the desired location.

The guide element 30 can be fabricated from a variety of materials to achieve the desired mechanical properties and bio-compatibility. The guide element 30 may be constructed from metal, e.g., wire, e.g., stainless steel wire, or nickel alloy wire. The guide element may be constructed from natural fibers, such as cotton or an animal product. The guide element 30 may be constructed from polymers, such as biodegradable polymers, such as polymers including repeating lactic acid, lactone, or glycolic acid units, such as polylactic acid (PLA). The guide element 30 may also be constructed from high-tensile strength polymers, such as Tyvek™ (high density polyethylene fibers) or Kevlar™ (para-aramid fibers). In an embodiment, guide element 30 is constructed from biodegradable suture, such as VICRYL™ (polyglactin 910) suture available from Ethicon Corp., Somerville, N.J.

In some embodiments, a magnetic anastomosis device 16 may include multiple guide elements 30. For example, as shown in FIGS. 8A, 8B, 8C, 8D, 8E, and 8F, a variety of attachment points can be used to provide control over the location and deployment of a self-assembling magnetic anastomosis device 16. As shown, four guide elements 30(1)-30(4) may be coupled to four separate segments of the device 16, respectively. Each guide element may include a distal end coupled to a respective portion of the anastomosis device, and a proximal end that can be manipulated (i.e., increased or decreased tension) to thereby manipulate the positioning and orientation of the anastomosis device 16 once it has self-assembled into the predetermined shape (i.e., a polygon). For example, as shown, guide element 30(1) is coupled to the most distal end segment, guide elements 30(2) and 30(3) are coupled to middle segments (segments between the most distal end segment and most proximal end segment), and guide element 30(4) is coupled to the most proximal end segment.

Figure 9:
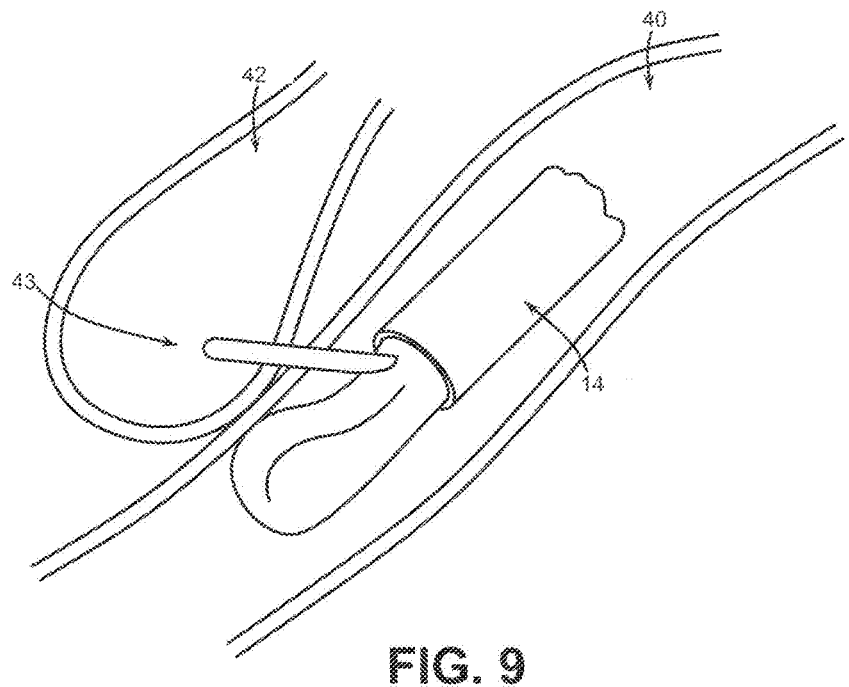
FIGS. 9, 10, 11, and 12 illustrate various methods of accessing the target site, specifically accessing a gallbladder via an endoscopic ultrasound guided procedure.

FIGS. 9-12 illustrates various methods of accessing the target site, specifically accessing a gallbladder 42 via an endoscopic ultrasound 14 guided procedure. FIG. 9 illustrates the use of monopolar energy on a hot probe or guide wire 43 for piercing and accessing the gallbladder 42.

Figure 10:
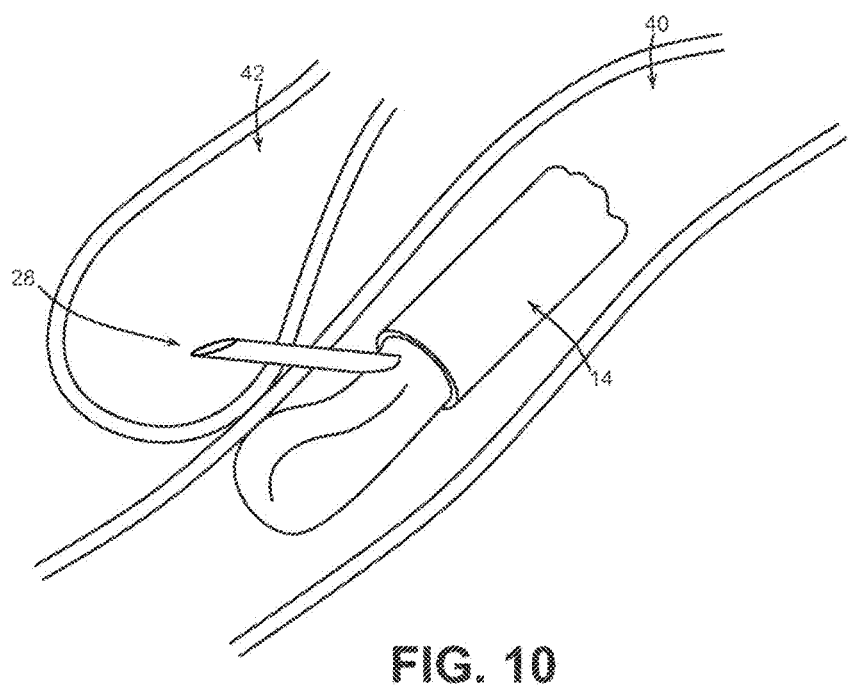

FIG. 10 illustrates the use of a fine aspiration needle (FNA) 28 for piercing and accessing the gallbladder 42.

Figure 11:
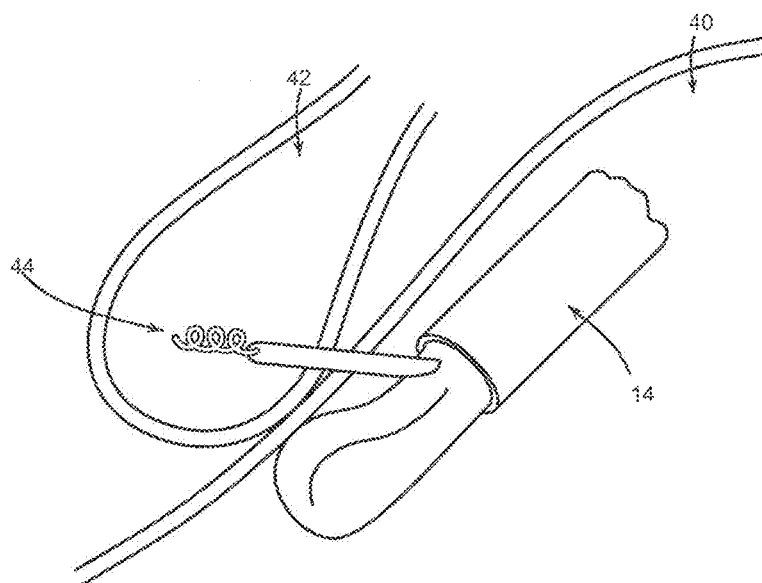

FIG. 11 illustrates the use of a corkscrew-type needle 44 for piercing and accessing the gallbladder 42.

Figure 12:
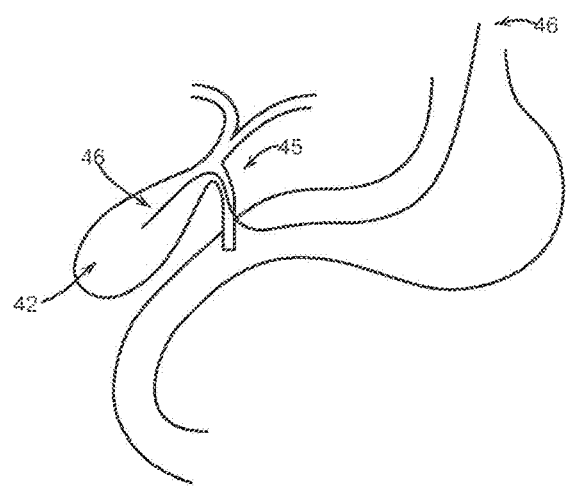

FIG. 12 illustrates the use of a guidewire 46 passed through the bile duct 45 and piercing into the gallbladder 42.

Figure 13:
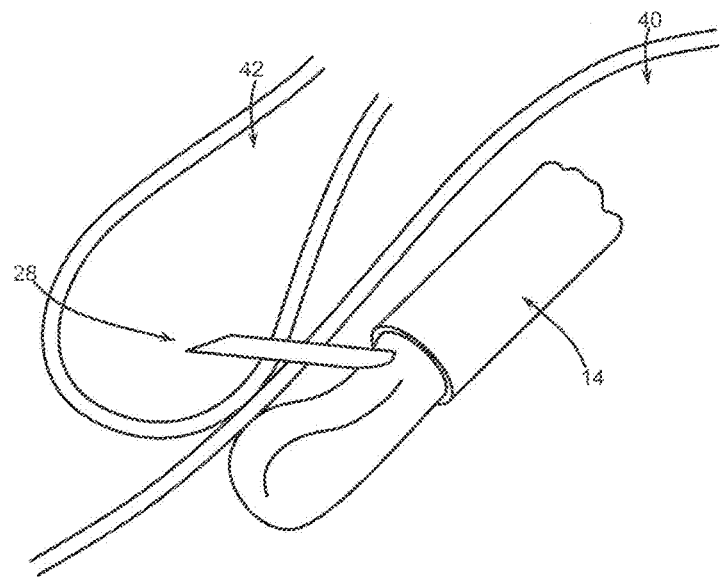
FIG. 13 shows endoscopic ultrasound guided needle piercing of the gallbladder to access the interior of the gallbladder for subsequent delivery of a magnet assembly therein.

FIG. 13 shows endoscopic ultrasound 14 guided needle 28 piercing of the gallbladder 42 to access the interior of the gallbladder 42 for subsequent delivery of a magnet assembly 16 therein.

Figure 14:
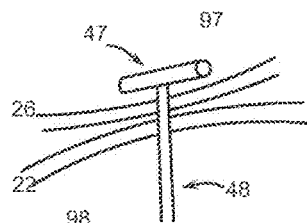
FIGS. 14, 15, 16 and 17 illustrate various devices for anchoring the access device and/or delivery device to the target site at the gallbladder.
Figure 15:
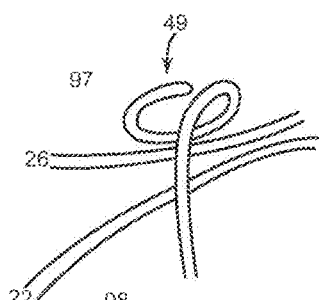
Figure 16:
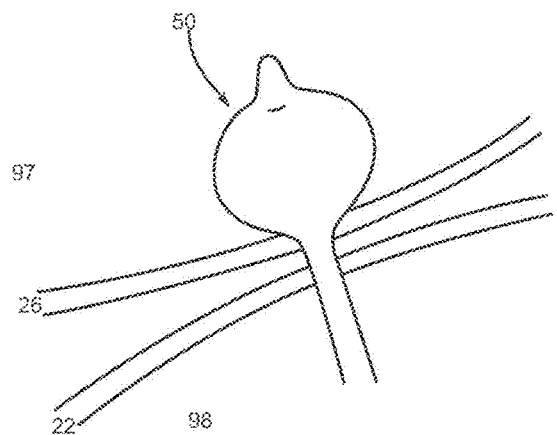
Figure 17:
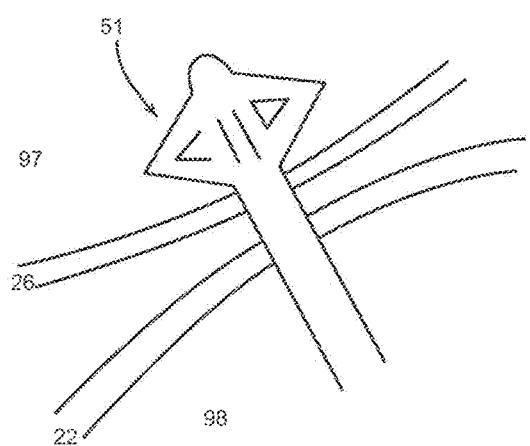

FIGS. 14, 15, 16 and 17 illustrate various devices for anchoring the access device and/or delivery device to the target site at the gallbladder 42. FIG. 14 illustrates a T-bar member 47 connected to a tether 48. FIG. 15 illustrates a nitinol coil (e.g., "pig tail") 49. FIG. 16 illustrates a balloon member 50 of a catheter. FIG. 17 illustrates a malecot catheter 51.

Figure 18A:
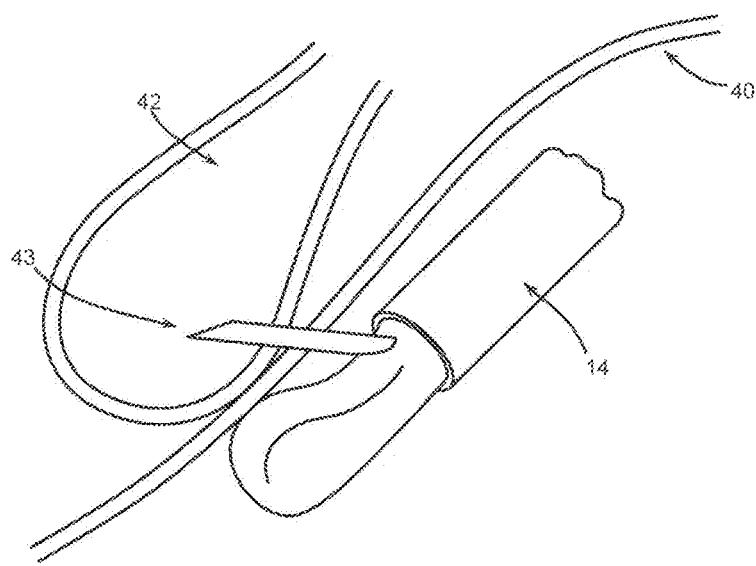
FIGS. 18A, 18B, 18C, 18D, 18E, and 18F illustrate a technique of accessing the gallbladder and delivering a pair of magnetic anastomosis devices for the formation of an anastomosis the gallbladder tissue and adjacent tissue.
Figure 18B:
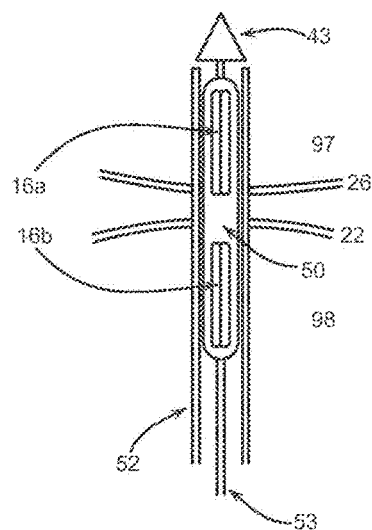
Figure 18C:
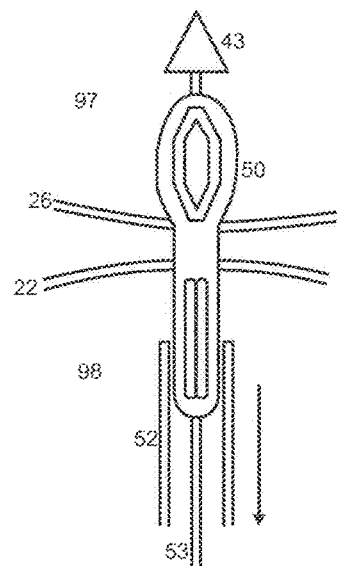
Figure 18D:
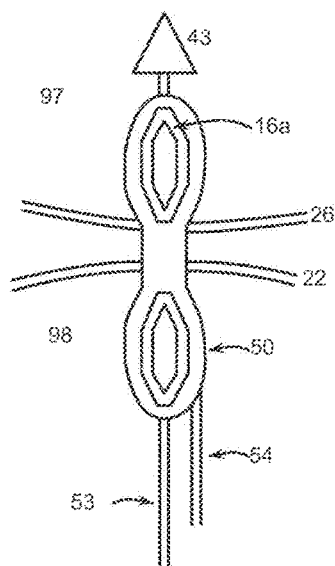
Figure 18E:
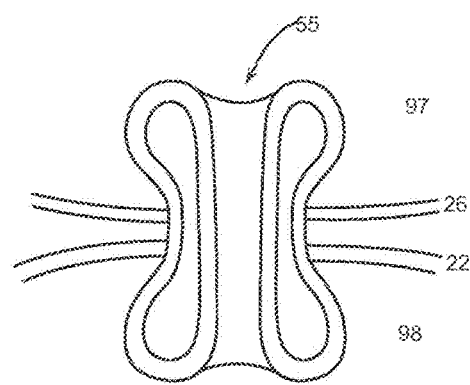
Figure 18F:
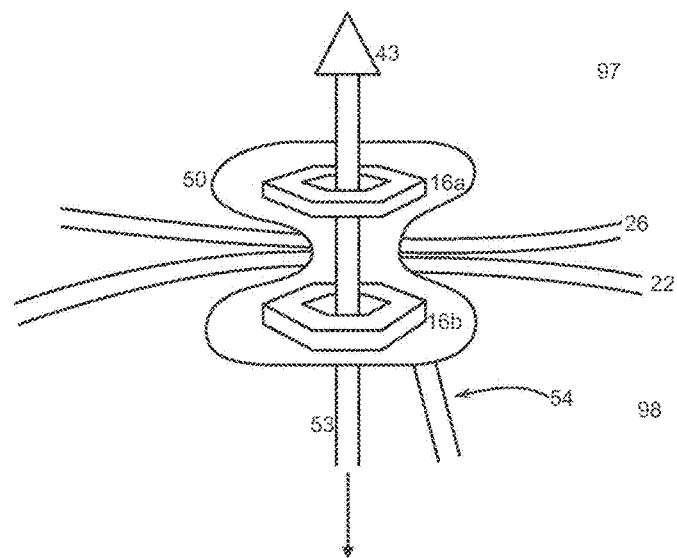

FIGS. 18A-18F illustrate a method of accessing the gallbladder, via endoscopic ultrasound guided access 14 and utilizing an access device emitting monopolar energy 43, anchoring a delivery device via the use of a balloon catheter 50, and subsequently delivering a pair of magnetic anastomosis devices 16a, 16b from the delivery device sheath 52 within the balloon 50 while the balloon 50 is anchored within the formed enterotomy between the gallbladder 42 tissue and adjacent tissue (i.e., stomach 40 or duodenum 41 tissue), thereby deploying the devices on either side of the respective tissues 22, 26 (i.e., first device within the gallbladder and second device within stomach or duodenum) for the formation of an anastomosis there between. The magnetic assemblies 16a, 16b are stored within the balloon 50 inside of a sheath 42 of the delivery device. By pulling back on the sheath 52 as shown in FIG. 18C, and advancing a conductor 53, the balloon 50 and magnetic assembly 16a is deployed into the gallbladder 42. An inflation line 54 inflates the balloon 50 allowing the magnetic devices 16a, 16b to self-assemble. The balloon 50 has an inner channel 55 as shown in cross section FIG. 18E. The monopolar energy tip 43 is then removed from the formed enterotomy as shown in FIG. 18F.

Figure 19:
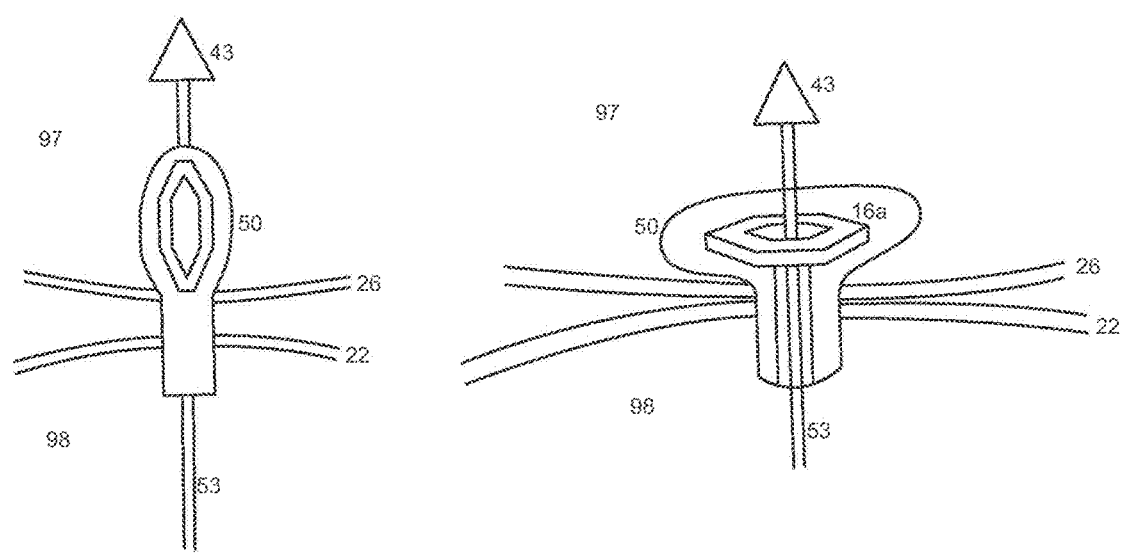
FIG. 19 illustrates a variation of design of FIGS. 18A-18F, specifically utilizing a balloon to deliver a single magnetic anastomosis device within the gallbladder, rather than delivering the pair.

FIG. 19 illustrates a variation of design of FIGS. 18A-18F, specifically utilizing a balloon 50 to deliver a single magnetic anastomosis device 16a within the gallbladder 42, rather than delivering the pair.

Figure 20A:
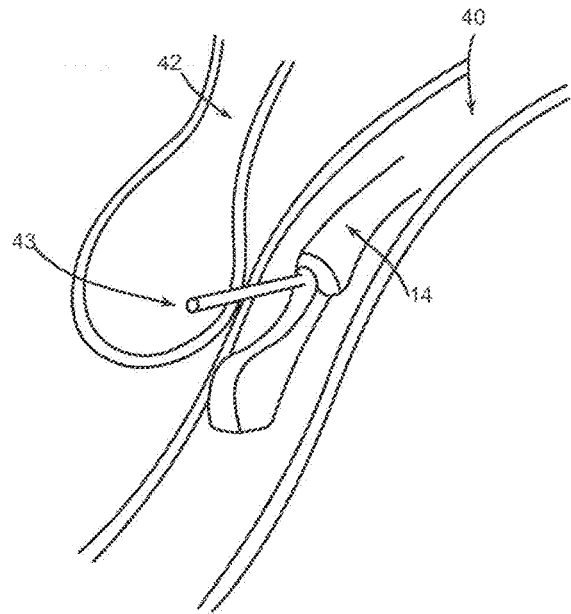
FIGS. 20A, 20B, and 20C illustrate a method of accessing the gallbladder, via endoscopic ultrasound guided access and utilizing a hot insertion tube emitting monopolar energy, and subsequently delivering a magnetic anastomosis device within the gallbladder via the hot tube.
Figure 20B:
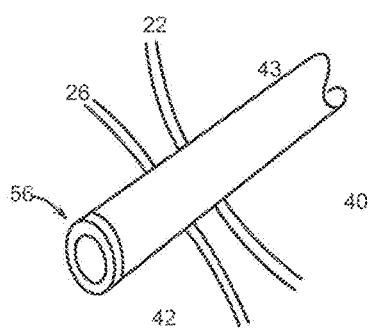
Figure 20C:
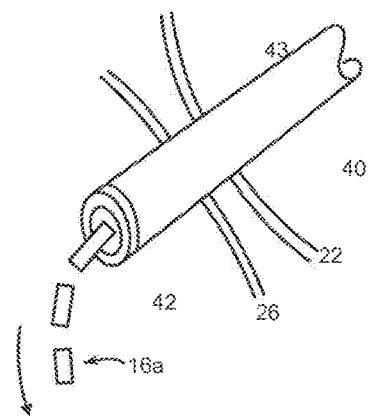

FIGS. 20A-20C illustrate a method of accessing the gallbladder 42, via endoscopic ultrasound guided access 14 and utilizing a hot insertion tube emitting monopolar energy 43, and subsequently delivering a magnetic anastomosis device 16 within the gallbladder 42 via the hot tube 43. An EUS scope 14 is advanced through the stomach 40. A monopolar energy tip or hot insertion tube 43, utilizing a monopolar ring 56 on the end of the tube 43, pierces the stomach and gallbladder tissues 26, 22 into the gallbladder 42 and subsequently deploys a magnetic anastomosis device 16 into the gallbladder 42 (FIG. 20C).

As shown in FIG. 20B, a user need only activate monopolar energy to advance the insertion tube 43 into the gallbladder 42.

Figure 21E:
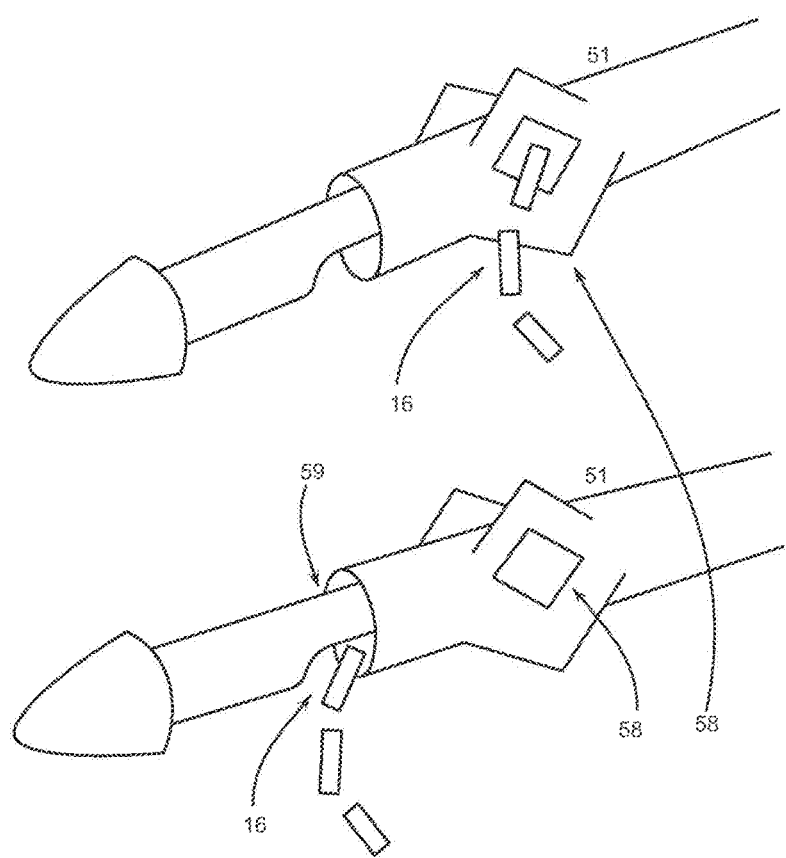

FIGS. 21A-21E illustrate a method of accessing the gallbladder 42, via endoscopic ultrasound 14 guided access and utilizing an access device having a conductor including a "hot" tip 43 emitting monopolar energy, anchoring the delivery device via the use of a malecot catheter 51, and subsequently utilizing the malecot catheter 51 as a conduit for delivering a magnetic anastomosis device 16 by way of a push rod 57 therethrough and into the gallbladder 42 while the malecot catheter 51 is anchored within the formed enterotomy between the gallbladder tissue 26 and adjacent tissue 22 (i.e., stomach or duodenum tissue). The hot tip 43 pierces the stomach and gallbladder tissues 22, 26, advancing the delivery device 14 into the gallbladder 42. A conductor 53 advances the hot tip 43 into the gallbladder 42, while a push rod 57 advances the magnet array 16. As shown in FIG. 21C, a malecot catheter 51 anchors the device in the gallbladder 42. The surgeon need only pull back on the push rod 57 to open the magnet array in the proximal lumen of the stomach 40. The hot tip in then advanced into the gallbladder 42 (FIG. 21D). FIG. 21E demonstrates the magnetic assembly 16 being deployed through a slot in the malecot catheter 51 as shown in the top figure, or through the end 59 as shown in the lower figure. The push rod 57 is advanced to deploy the magnets 16. The windows of the malecot catheter 51 in some embodiments may have radio opaque markers 58 in order to keep the window oriented properly.

Figure 22C:
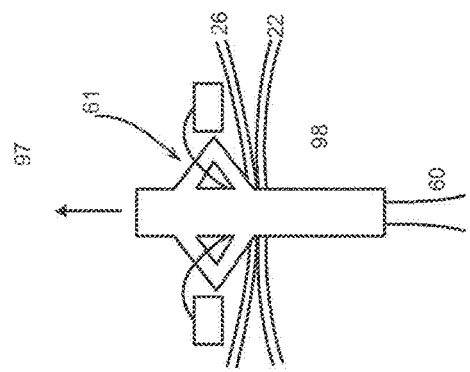
FIGS. 22A, 22B, and 22C illustrate a variation of the procedure and devices illustrated in FIGS. 21A-21E in that the magnetic anastomosis device is preloaded into a distal end of the malecot catheter of the delivery device resulting in delivery and deployment of the device upon transitioning of the malecot end into an anchored position.
Figure 22B:
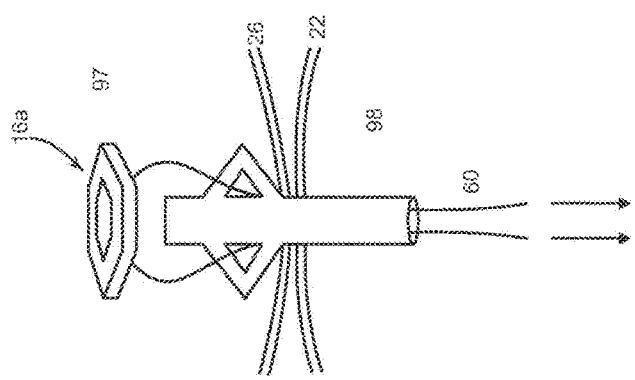
Figure 22A:
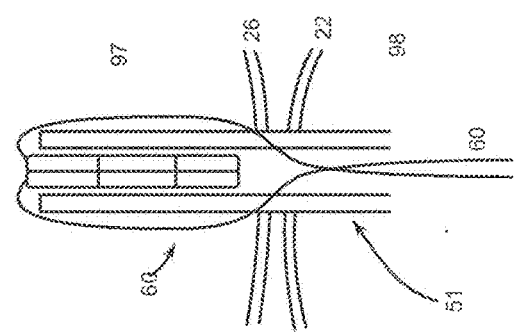

FIGS. 22A-22C illustrate a variation of the procedure and devices illustrated in FIGS. 21A-21E in that the magnetic anastomosis device 16 is preloaded into a distal end of the malecot catheter 51 of the delivery device 14 resulting in delivery and deployment of the device 16 upon transitioning of the malecot end 59 into an anchored position. Sutures 60 may be used to guide the magnetic anastomosis device 16 from the malecot catheter body 51 into the distal lumen 97. The magnet 16 is pushed out of the distal end of the malecot catheter 51 and is oriented by pulling back on the sutures 60. By pushing forward on the malecot catheter 51, the catheter windows 61 cut the sutures 60, releasing the magnetic assembly 16.

Figure 23:
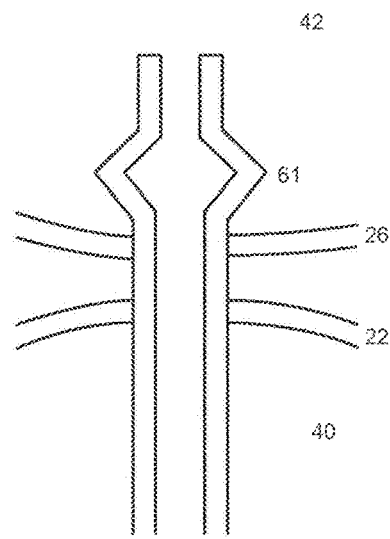
FIG. 23 illustrates a malecot catheter having a distal end that expands into the anchored position on one side of the gallbladder tissue wall.
Figure 24:
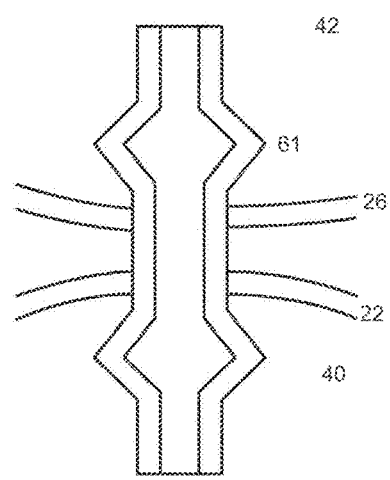
FIG. 24 illustrates a malecot catheter having a distal end that expands into the anchored position on both sides of the gallbladder tissue wall.

FIG. 23 illustrates a malecot catheter 51 having a distal end that expands into the anchored position on one side of the gallbladder 42 tissue wall 26. FIG. 24 illustrates a malecot catheter 51 having a distal end that expands into the anchored position on both sides of the gallbladder tissue wall 26. In both instances, a temporary malecot may be placed inside of the gallbladder 42 to create a temporary conduit, which allows for drainage to occur immediately and could further allow for insufflation of the gallbladder as well. It should be noted that, any of the embodiments that provide access from the GI tract into the gallbladder (malecot, hot tube, nitinol coil, balloon, etc.), specifically any of the devices that creates a channel through which the magnetic anastomosis device 16 will pass, can also serve as a drainage channel. More specifically, after the access channel has been created, any fluid or material within the gallbladder could be evacuated (either on its own or if suction is applied) before delivery of the magnetic anastomosis device 16 begins. The channel could also be used to push fluid into the gallbladder prior to draining out the gallbladder (potentially doing the fill/drain cycle a number of times) in order to 'clean' out the gallbladder in the event that the gallbladder has excess fluid and contents within (i.e., bile or other contents).

Figure 25E:
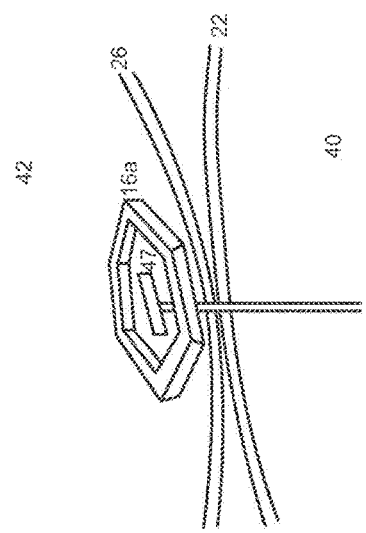
Figure 25D:
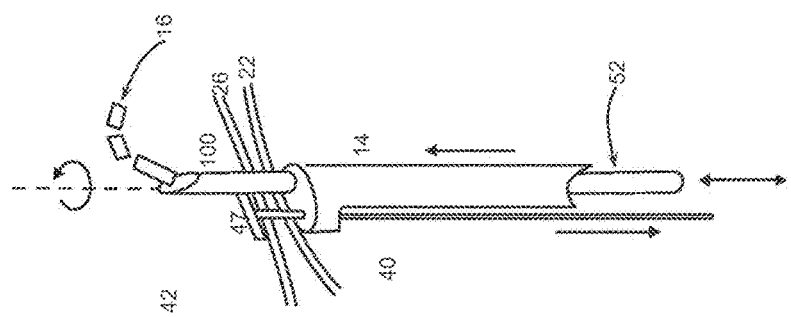

FIGS. 25A-25E illustrate a method of accessing the gallbladder 42, via endoscopic ultrasound guided access needle 14 (22 or 25 gauge for easy access), anchoring the delivery device via the use of a T-bar assembly 47 and stabilizer member 62, and subsequently delivering a magnetic anastomosis device 16 therethrough, via a deployment sheath 52, and into the gallbladder 42 while the T-bar 47 is anchored within the formed enterotomy between the gallbladder tissue 26 and adjacent tissue 22 (i.e., stomach or duodenum tissue). As shown in FIG. 25A, the T-bar 47 is tethered 48 to the gallbladder 42 wall. The stabilizer member 62 is then advanced to the wall of the duodenum 41 or stomach 40 for traction, as shown in FIG. 25B. The deployment sheath 52 is then advanced into the gallbladder 42, at which point the magnetic anastomosis device 16 can be delivered, as illustrated in FIG. 25C. FIG. 25D demonstrates the T-bar 47 anchoring the delivery device 14 into the gallbladder 42 wall by pulling back on the tether 48. The surgeon advances the deployment sheath 52 to deploy the magnetic device 16a into the gallbladder 42. The delivery device 14 may rotate in some embodiments in order to help align the magnetic device 16 within the gallbladder 42. FIG. 25E illustrates the fully formed magnetic device 16 encasing or surrounding the T-bar 47. In some embodiments, the T-bar 47 may be magnetic to engage with the anastomosis device 16.

Figure 26C:
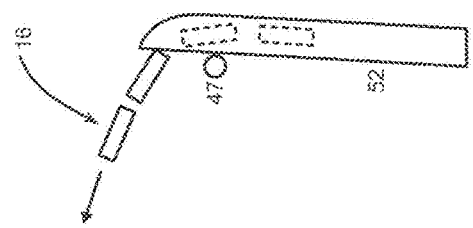
FIGS. 26A, 26B, 26C illustrate a variation of the procedure and devices illustrated in FIGS. 25A-25E in that the deployment sheath includes a notch on a distal end thereof configured to engage the T-bar upon advancement through the enterotomy, thereby pushing the T-bar to the side to allow for subsequent delivery and deployment of the magnetic anastomosis device.
Figure 26B:
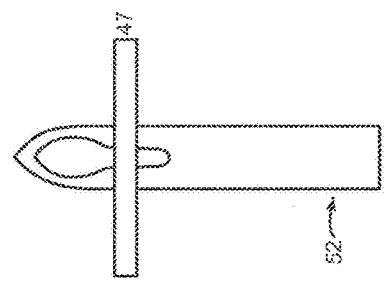
Figure 26A:
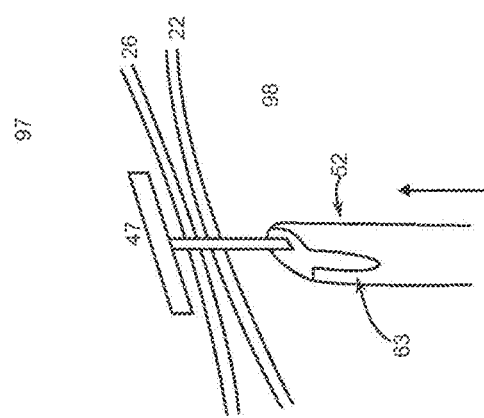

FIGS. 26A-26C illustrate a variation of the procedure and devices illustrated in FIGS. 25A-25E in that the deployment sheath 52 includes a notch 63 on a distal end thereof configured to engage the T-bar 47 upon advancement through the enterotomy, thereby pushing the T-bar 47 to the side to allow for subsequent delivery and deployment of the magnetic anastomosis device 16.

Figure 27C:
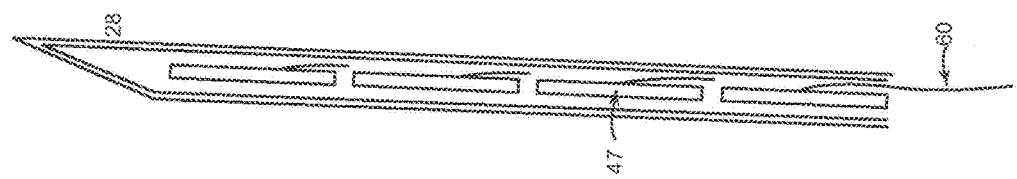
FIGS. 27A, 27B, and 27C illustrate another variation of the procedure and devices illustrated in FIGS. 25A-25E in that, rather than including a deployment sheath for delivering a self-assembling magnetic anastomosis device, as previously described herein, the assembly of FIGS. 27A-27C relies on the depositing of T-bars through an access needle, such that a grouping of T-bars are configured to self-assemble into an array and serve as the distal anastomosis device to correspondingly mate with a proximal magnetic anastomosis device positioned on the other side to subsequently compress tissue there between to form an anastomosis.
Figure 27B:
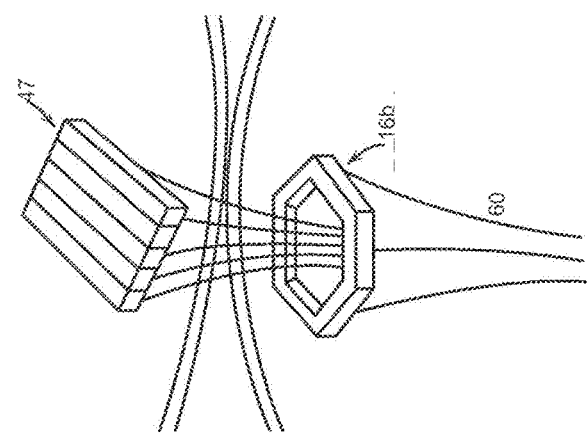
Figure 27A:
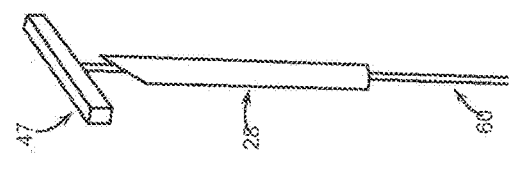

FIGS. 27A-27C illustrate another variation of the procedure and devices illustrated in FIGS. 25A-25E in that, rather than including a deployment sheath for delivering a self-assembling magnetic anastomosis device 16, as previously described herein, the assembly of FIGS. 27A-27C relies on the depositing of T-bars 47 through an access needle 28, such that a grouping of T-bars 47 are configured to self-assemble into an array and serve as the distal anastomosis device to correspondingly mate with a proximal magnetic anastomosis device 16b positioned on the other side to subsequently compress tissue there between to form an anastomosis. Each T-bar 47 is magnetic and tethered to the delivery device by sutures 60. FIG. 27C illustrates the multiple magnetic T-bars 47 stored linearly within an access needle 28 for deployment into a lumen, and tethered to the delivery device 14 by sutures 60.

Figure 28A:
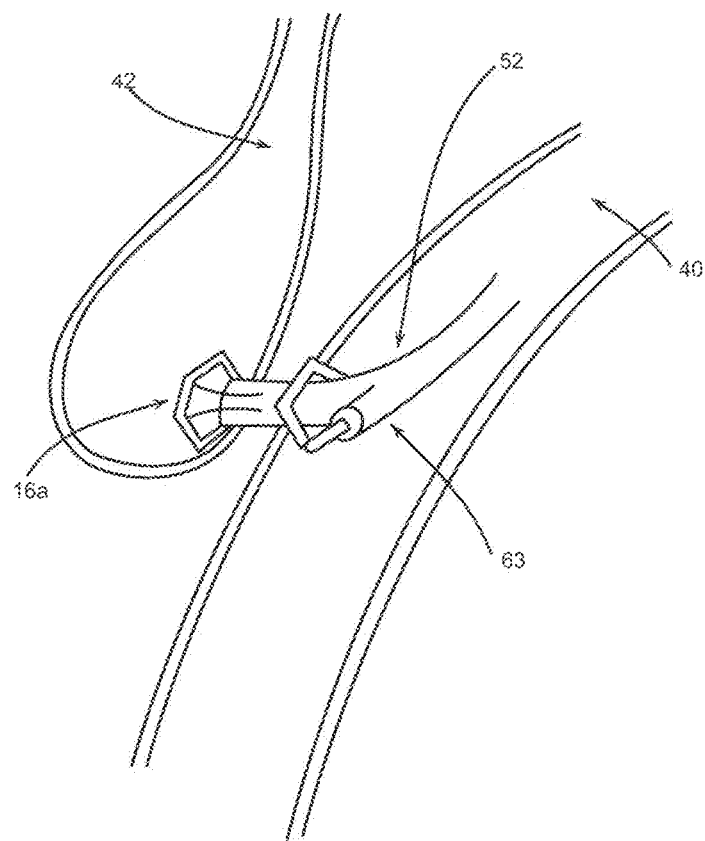
FIGS. 28A, 28B, and 28C illustrate a method of accessing the gallbladder, via endoscopic ultrasound guided access needle access, utilizing a side port deployment sheath for delivery and deployment of a pair of magnetic anastomosis devices.
Figure 28B:
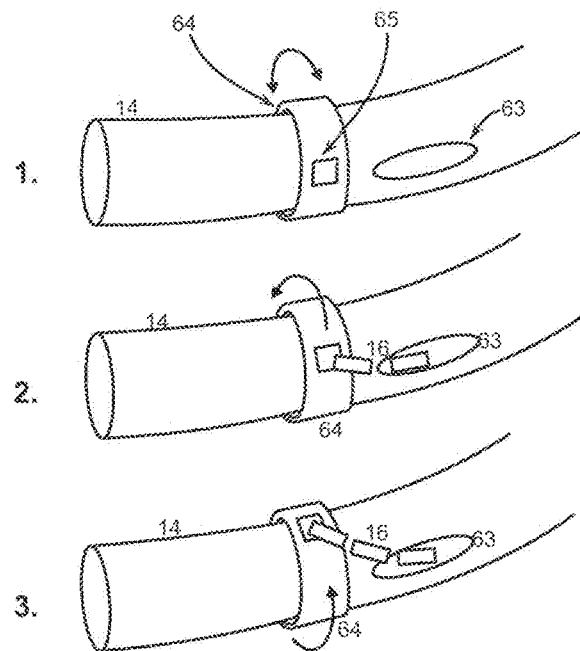
Figure 28C:
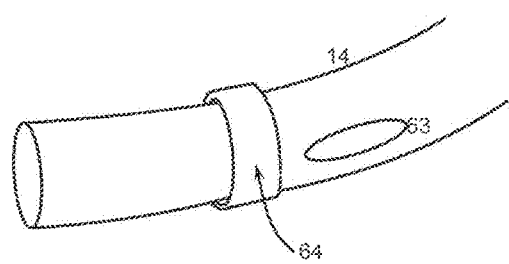

FIGS. 28A-28C illustrate a method of accessing the gallbladder 42, via endoscopic ultrasound guided access needle access 14, utilizing a side port deployment sheath 63 for delivery and deployment of a pair of magnetic anastomosis devices 16.

FIG. 28A illustrates an EUS scope 14 accessing the stomach 40 and piercing the stomach tissue into the gallbladder 42. A distal magnet 16a is deployed into the gallbladder 42 by advancing a deployment sheath 52 into the gallbladder 42. The surgeon pulls back on the delivery device 14 which brings a side port 63 in the delivery device fully within the stomach 40. The second anastomosis device 16b is then deployed from the side port 106 in the sheath 52.

FIG. 28B illustrates an embodiment of the device wherein there is a metal ring 64 to guide the magnet 16 out and around the delivery device 14. The magnet 16 is deployed from the side port 63 of the sheath 52. The magnet 16 is caught by the metal insert 65 of the rotating ring 64. The ring 64 rotates around the delivery device 14 in order to assist deployment and assembly of the magnet 16. In some embodiments, the ring 64 may be free spinning, or may rotate when the magnet 16 is pushed out. In some embodiments the ring 64 can be actively rotated to pull the magnet 16 out.

FIG. 28C illustrates a close-up view of the metal ring 64. The metal ring 64 completely surrounds the sheath 52 of the delivery device 14 and guides the magnet 16 around the delivery device 14 to assist deployment and assembly.

Figure 29A:
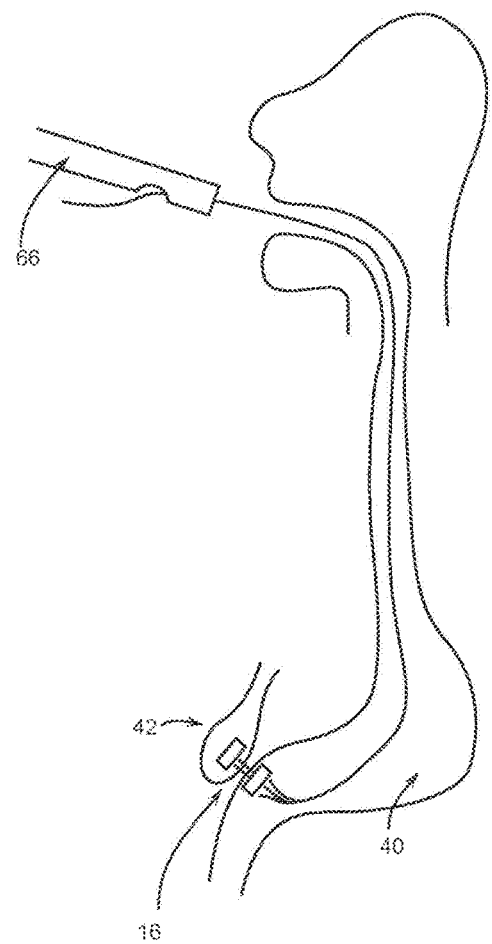
FIGS. 29A, 29B, and 29C illustrate a knotting member configured to secure already deployed and positioned magnetic anastomosis devices to the target site tissues and subsequently cut guide elements or sutures coupled thereto.
Figure 29B:
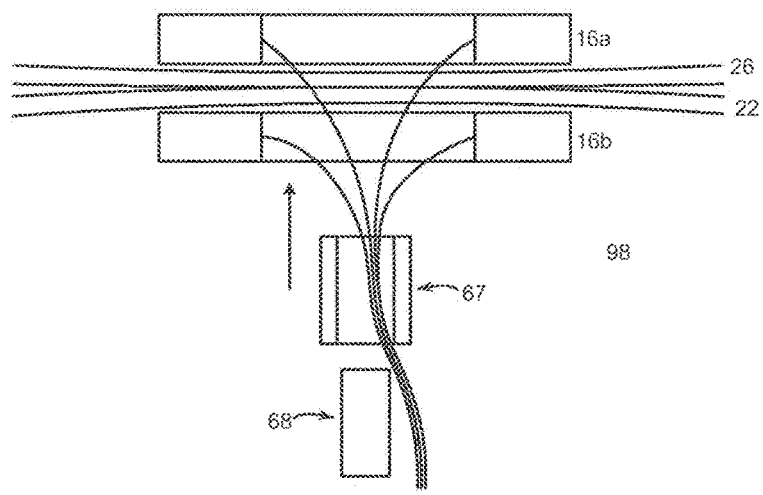
Figure 29C:
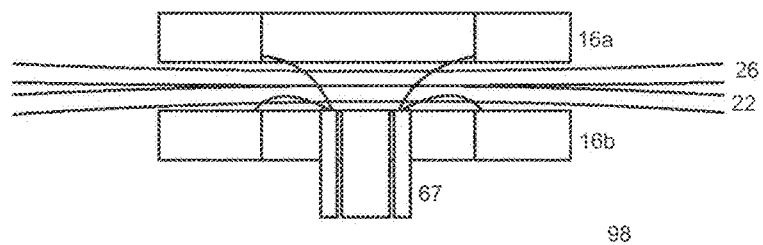

FIGS. 29A-29C illustrate a knotting member 66 configured to secure already deployed and positioned magnetic anastomosis devices 16 to the target site tissues and subsequently cut guide elements or sutures 60 coupled thereto. As shown in FIG. 29A, the knotting member 66 is advanced over guide elements or sutures 60 within a working channel of a scope 14. The knotting member 66 is advanced through the stomach 40 by way of the scope 14 in order to cut the sutures 60 of previously positioned anastomosis devices 16 within the stomach 40 and gallbladder 42.

As shown in FIG. 29B, the knotting member 66 advances towards the magnetic anastomosis devices 16, wherein the knotting member 66 generally consists of an outer tube member 67 and an inner rod member 68, such that, upon reaching the devices, the inner rod member 68 can be pressed towards a distal end of the outer tube member 67, thereby securing a portion of the guide elements 60 there between and further cutting the guide elements 60 in the process.

FIG. 29C illustrates the inner rod member 68 cinched against the outer tube member 67 of the knotting member 66 in order to cut the sutures or guide elements 60 from the magnetic anastomosis devices 16.

FIGS. 30A-30D illustrate a method of accessing the gallbladder 42, via endoscopic ultrasound guided access needle access 14, and delivering a magnetic coil 69 or ring configured to transition from a substantially linear shape to a substantially annular shape upon delivery into the gallbladder 42 and is configured to serve the distal anastomosis device to correspondingly mate with a proximal magnetic anastomosis device 16b positioned on the other side to subsequently compress tissue there between to form an anastomosis.

Figures 30A, 30B:
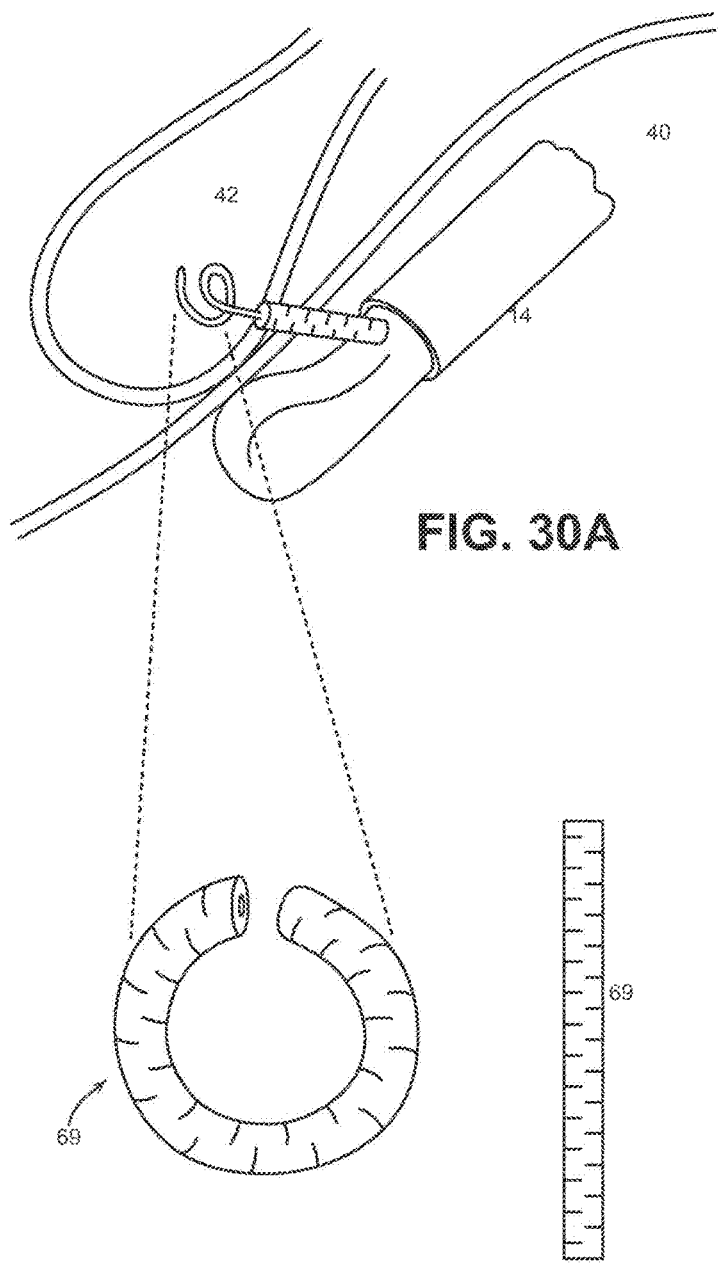
FIGS. 30A, 30B, 30C, and 30D illustrate a technique of accessing the gallbladder and delivering a pair of magnetic anastomosis devices for the formation of an anastomosis the gallbladder tissue and adjacent tissue.

FIG. 30A illustrates an EUS scope advancing into the stomach 40. An access needle 28 pierces the stomach 40 and gallbladder 42 tissue, thereby deploying a metallic coil 69 into the gallbladder 42. The metallic coil 69 is stored in the delivery device 14 in a linear shape as shown in FIG. 30B, and upon deployment forms a substantially annular shape. The metallic coil 69 in some embodiments is made of a laser cut hypotube to allow it to flex.

Figure 30C:
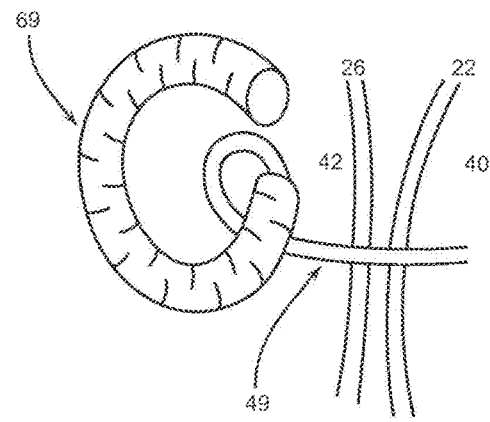

FIG. 30C illustrates the hypotube 69 advancing along a nitinol coil 49 as it is deployed from the delivery device 14 into the gallbladder 42. As the metal hypotube 69 is advanced along the nitinol coil 49, it changes form from a substantially linear shape from storage to a substantially annular shape as it is deployed.

Figure 30D:
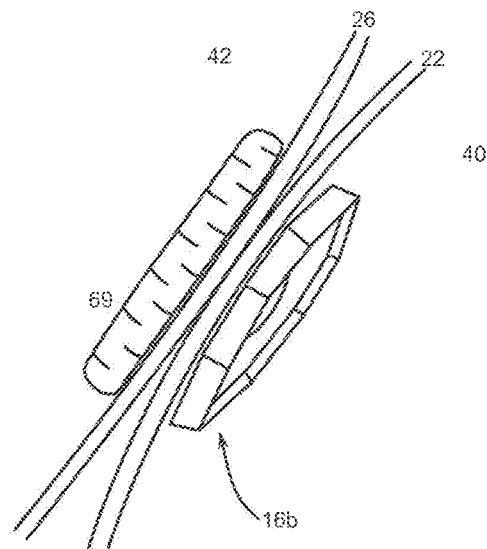

FIG. 30D illustrates the proximal magnet 16b engaging with a metal hypotube 69 in order to compress the tissues therebetween and form an anastomosis.

Figure 31A:
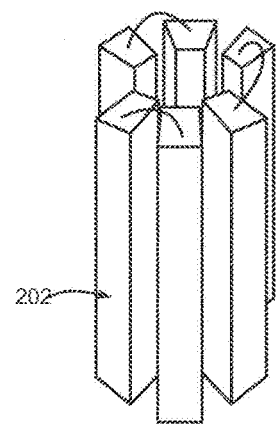
FIGS. 31A and 31B illustrate a set of magnetic segments prepackaged in an unstable polarity including a plurality of guide elements, tethers, or sutures coupling adjacent segments to one another to assist in self-assembly of the magnetic segments into a polygon deployed shape.
Figure 31B:
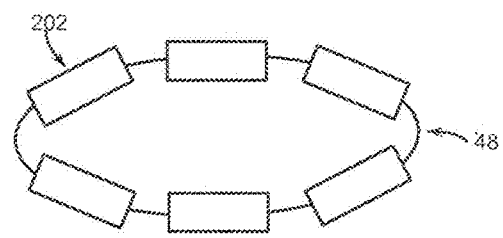

FIGS. 31A and 31B illustrate a set of magnetic segments 202 prepackaged in an unstable polarity including a plurality of guide elements 30, tethers 48, or sutures 60 coupling adjacent segments 202 to one another to assist in self-assembly of the magnetic segments into a polygon deployed shape. The magnetic segments 202 are pre-packaged in an unstable polarity so that upon deployment they self-assemble into the desired shape. End to end tethers 48 help snap the magnetic segments 202 into the desired shape.

Figure 32A:
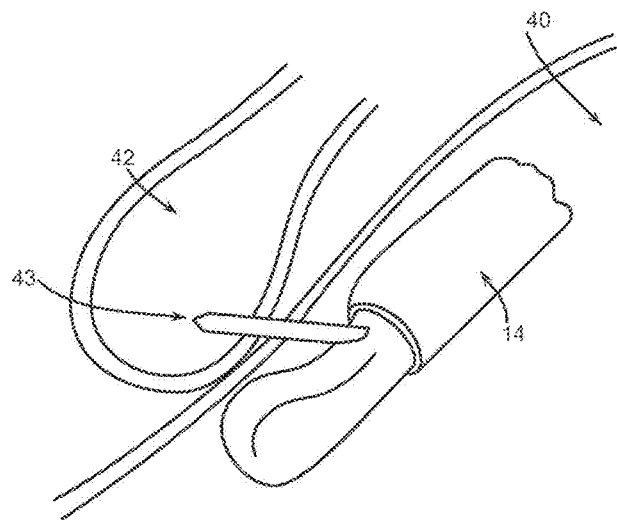
FIGS. 32A and 32B illustrate a method of accessing the gallbladder, via endoscopic ultrasound guided access and utilizing an access device having a conductor including a "hot" tip emitting monopolar energy, and subsequently delivering the prepackaged magnetic segments of FIGS. 31A and 31B into the gallbladder by way of a sheath.
Figure 32B:
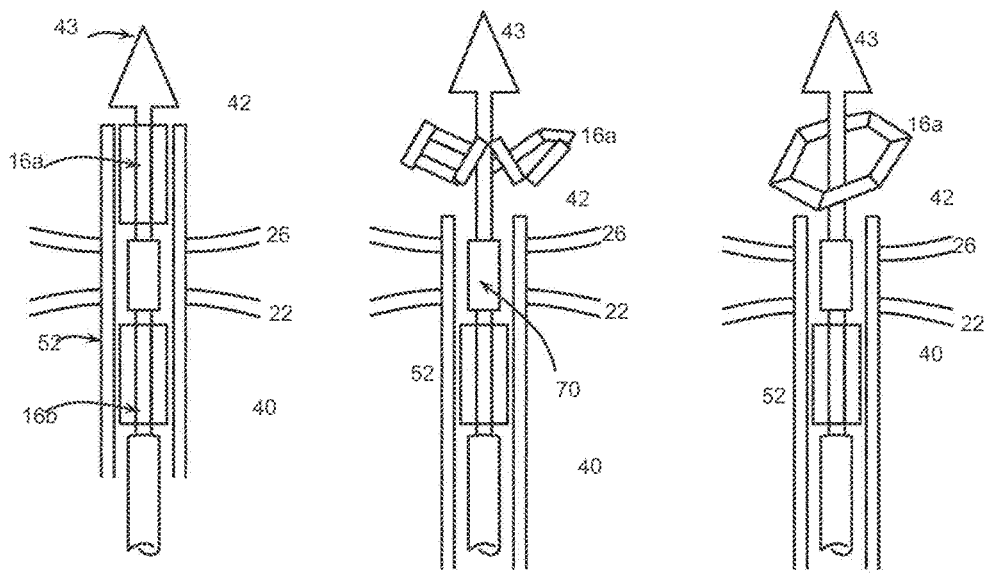

FIGS. 32A and 32B illustrate a method of accessing the gallbladder 42, via endoscopic ultrasound guided access 14 and utilizing an access device having a conductor including a "hot" tip emitting monopolar energy 43, and subsequently delivering the prepackaged magnetic segments 202 of FIGS. 31A-31B into the gallbladder 42 by way of a sheath 52.

FIG. 32A illustrates an EUS scope 14 accessing the stomach 40. A "hot" tip emitting monopolar energy 43 is used to pierce the stomach 40 and gallbladder 42 tissues in order to access the gallbladder 42. Upon accessing the gallbladder 42 a magnetic assembly 16 is deployed as illustrated in FIG. 32B.

FIG. 32B illustrates the deployment of a magnetic anastomosis device 16a into the gallbladder 42. A "hot" access tip 43 pierces the stomach 40 and gallbladder 42 tissues in order to access the gallbladder 42. A sheath 52 is advanced into the gallbladder 42, in which a distal magnetic assembly 16a, a spacer 70, and proximal magnetic assembly 16b are stored in a linear arrangement. By pulling back on the sheath 52, the distal magnetic assembly 16a is deployed into the gallbladder 42, wherein it self-assembles into a polygonal shape, in this illustration an octagon.

Figure 33A:
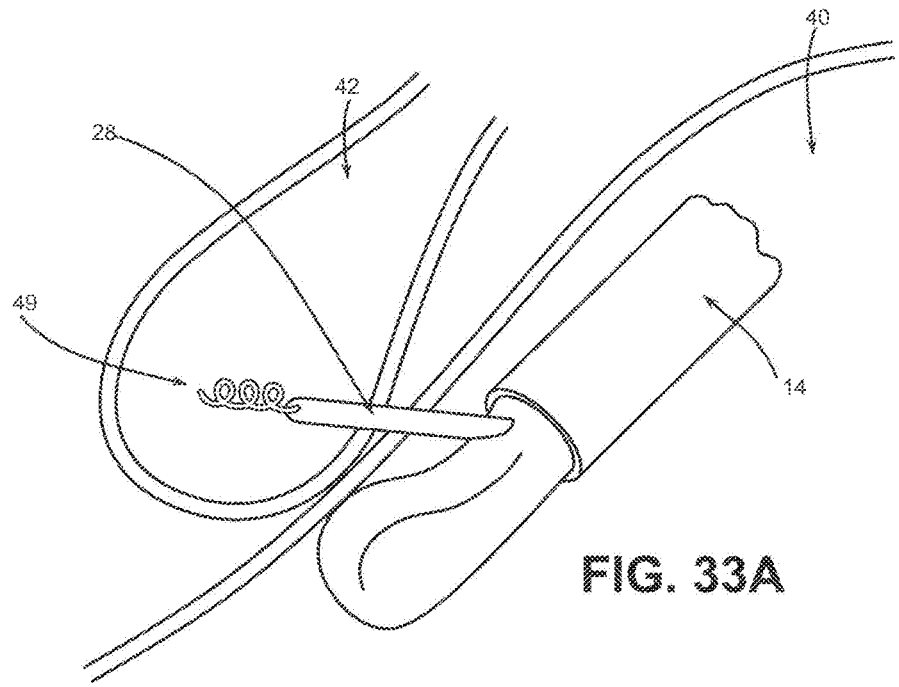
FIGS. 33A, 33B, and 33C illustrate a method of accessing the gallbladder, via endoscopic ultrasound guided access and utilizing a needle for access into the gallbladder, and subsequent delivery of a coiled stack of magnetic segments configured to serve the distal anastomosis device to correspondingly mate with a proximal magnetic anastomosis device positioned on the other side to subsequently compress tissue there between to form an anastomosis.
Figure 33B:
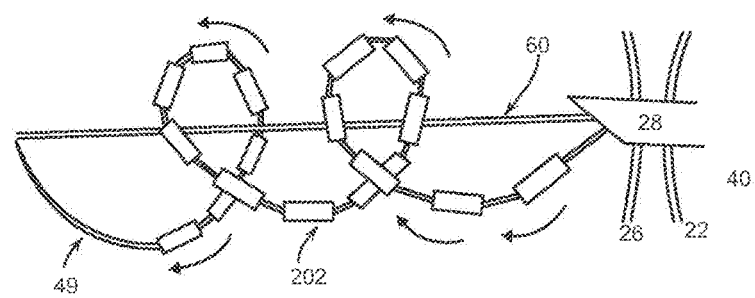
Figure 33C:
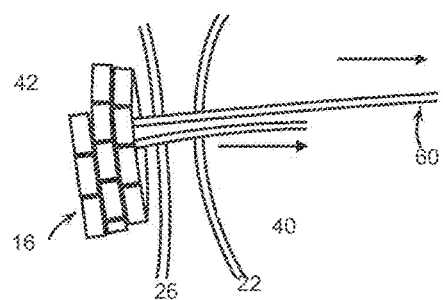

FIGS. 33A-33C illustrate a method of accessing the gallbladder 42, via endoscopic ultrasound guided access 14 and utilizing a needle 28 for access into the gallbladder 42, and subsequent delivery of a coiled stack of magnetic segments 202 configured to serve the distal anastomosis device 16a to correspondingly mate with a proximal magnetic anastomosis device 16b positioned on the other side to subsequently compress tissue there between to form an anastomosis.

As shown in FIG. 33A, the nitinol coil 49 is advanced into the gallbladder 42 by way of an access needle 28 within an EUS scope 14. The magnetic segments 202 are then advanced around the extended nitinol coil 49 held in place by a suture 60, as shown in FIG. 33B. Upon pulling a suture 60, as shown in FIG. 33C, the magnetic segments 202 collapse upon one another (due to magnetic attraction forces) and form a coiled stack of magnets 16 upon removal of the nitinol coil 49.

Figure 34A:
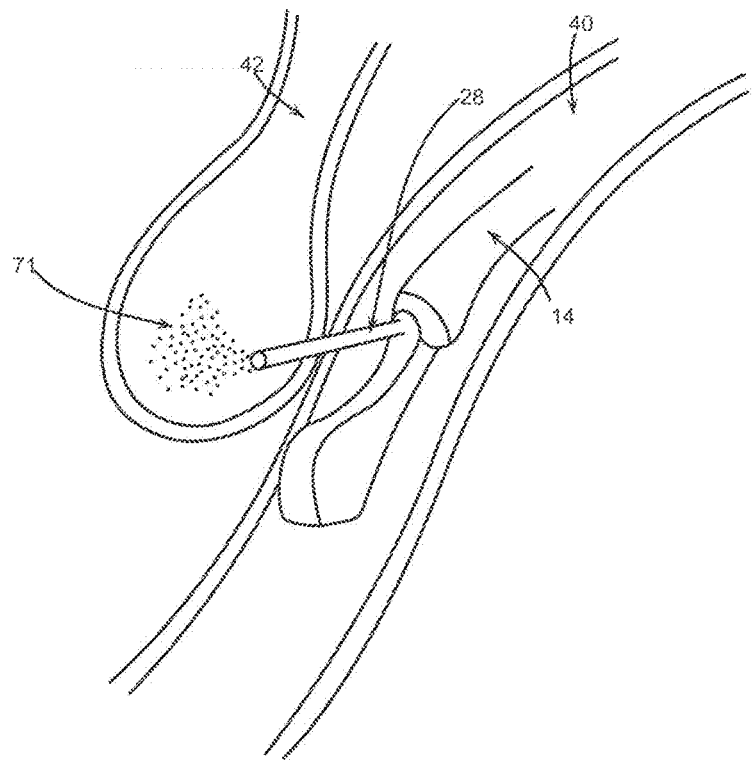
FIGS. 34A and 34B illustrate a technique of accessing the gallbladder and delivering a pair of magnetic anastomosis devices for the formation of an anastomosis between the gallbladder tissue and adjacent tissue.
Figure 34B:
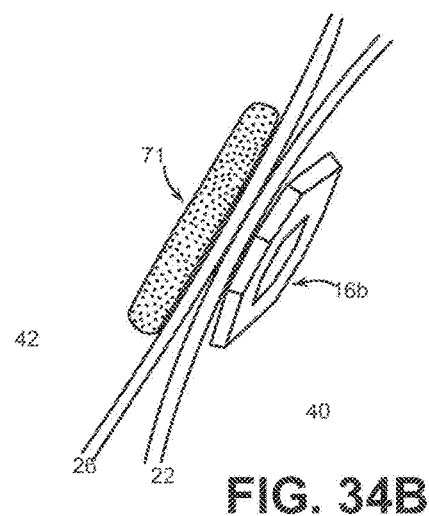

FIGS. 34A-34B illustrate a method of accessing the gallbladder 42, via endoscopic ultrasound guided access 14 and utilizing a needle 28 for access into the gallbladder 42, and subsequent delivery of a magnetic fluid or suspension of magnetic particles 71 into the gallbladder 42 configured to serve as the distal anastomosis device to correspondingly mate with a proximal magnetic anastomosis device 16b positioned on the other side to subsequently compress tissue 26, 22 there between to form an anastomosis.

FIG. 34A illustrates an EUS scope 14 accessing the stomach 40. An access needle 28 pierces the stomach 40 and gallbladder 42 tissues to access the gallbladder 42. The access needle 28 then deploys magnetic fluid or particles 71 into the gallbladder 42.

FIG. 34B illustrates the magnetic particles 71 being attracted to a deployed proximal magnetic anastomosis device 16b. The magnetic particles 71 form a polygonal annular shape consistent with that of the proximal anastomosis device 16b, thereby compressing the tissue 26, 22 between the devices and forming an anastomosis.

Figure 35:
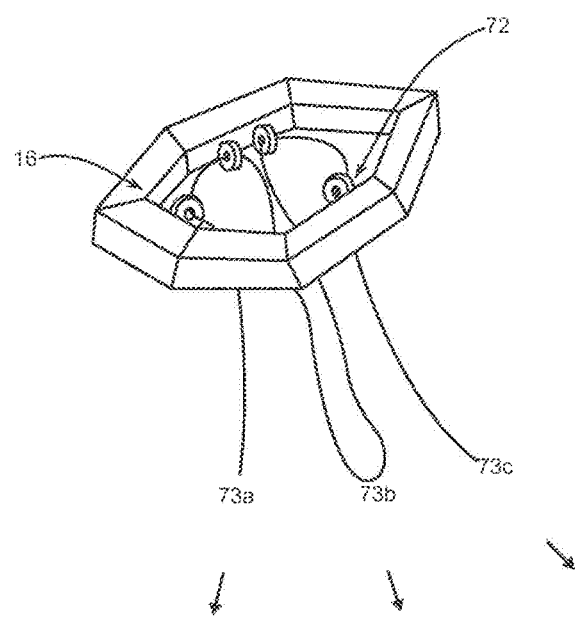
FIG. 35 illustrates a magnetic anastomosis device comprising a continuous guide element or suture that is coupled to a plurality of the magnetic segments of the device by way of eyelets positioned on each of the plurality of magnetic segments.

FIG. 35 illustrates a magnetic anastomosis device 16 comprising a continuous guide element or suture 60 that is coupled to a plurality of the magnetic segments 202 of the device by way of eyelets 72 positioned on each of the plurality of magnetic segments 202. Eyelets 72 are placed on the inside of the magnet 16 to prevent sutures 60 from getting trapped or pinched between magnets 16. A continuous suture 60 is run through the eyelets 72 in order to guide and position the magnet 16 for formation of an anastomosis. Suture legs 73a, 73b, 73c may be pulled individually or simultaneously in order to manipulate the magnet 16. To remove the suture 60, leg 73a or 73c may be pulled individually.

Figure 36:
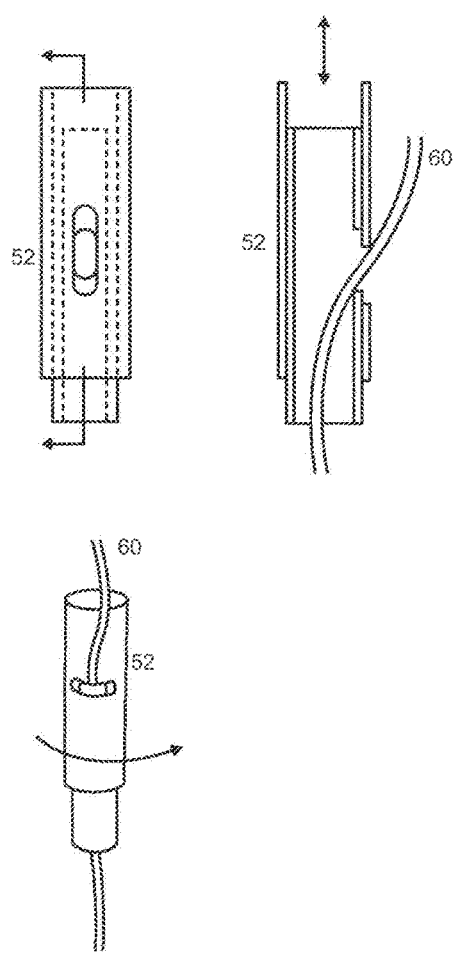
FIG. 36 illustrates one embodiment of a suture cutting arrangement within a deployment sheath of the delivery device, or a secondary device, for cutting the sutures coupled to the magnetic anastomosis devices.

FIG. 36 illustrates one embodiment of a suture cutting arrangement within a deployment sheath 52 of the delivery device, or a secondary device, for cutting the sutures 60 coupled to the magnetic anastomosis devices. A push/pull guillotine utilizing an anvil/sharp or sharp/sharp configuration is used to cut the sutures 60. By pushing and pulling on the cutting arrangement, a knife edge is exposed. Pushing/pulling on the cutting arrangement also introduces tension to the sutures. The tensed sutures are pulled over the sharp edge of the cutting arrangement to be cut and subsequently removed from the cutting arrangement. In some embodiments, the cutting arrangement may be twisted to expose a knife edge to cut the sutures.

Figure 37A:
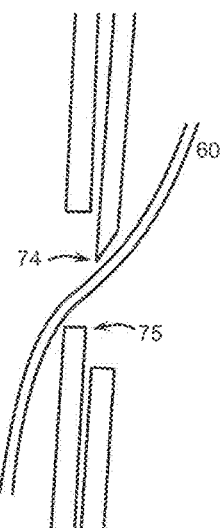
FIGS. 37A and 37B are enlarged side views illustrating an anvil/sharp arrangement and a sharp/sharp arrangement for cutting sutures.
Figure 37B:
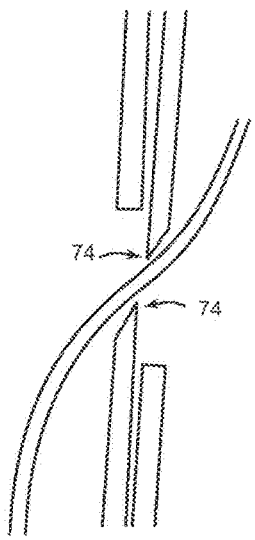
Figure 38:
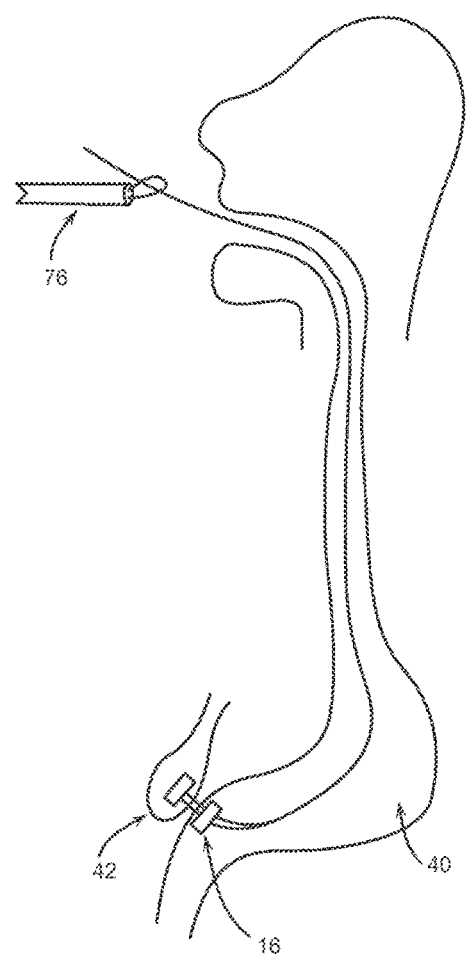
FIG. 38 illustrates a snare device (secondary device) configured to be inserted over the guide elements or sutures coupled to the magnetic anastomosis devices and configured to cut said sutures or guide elements once they have been deployed and positioned at a target site.

FIGS. 37A and 37B are enlarged side views illustrating an anvil/sharp arrangement and a sharp/sharp arrangement for cutting sutures. FIG. 38 illustrates a snare device (secondary device) configured to be inserted over the guide elements or sutures coupled to the magnetic anastomosis devices and configured to cut said sutures or guide elements once they have been deployed and positioned at a target site.

FIG. 37A illustrates a sharp 74/anvil 75 cutting arrangement. A tensed suture 60 is brought over the exposed sharp edge 74 to be cut by pushing and pulling on the cutting arrangement.

FIG. 37B illustrates a sharp/sharp cutting arrangement. By pushing and pulling on the cutting arrangement, two sharp edges 74 are exposed, cutting a tensed suture 60.

FIG. 38 illustrates a snare device 76 to cut sutures 60. A snare device 76 is advanced into the stomach 40 through an endoscope or similar delivery device 14. After the magnets 16 are positioned in the desired location to form an anastomosis, the snare device 76 is advanced over the sutures 60 through a working channel of the scope 14. The snare device 76 cuts the sutures 60, detaching them from the deployed magnetic anastomosis devices 16.

Figure 39A:
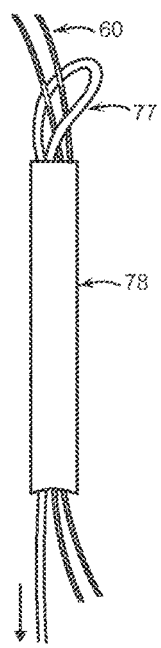
FIG. 39A illustrates a snare device comprising a resistive heating element for cutting guide elements.

FIG. 39A illustrates a snare device 76 comprising a resistive heating element 77 for cutting guide elements 60. The snare member 76 comprises a support tube 78 that guides the snare device 76 into position to cut the sutures 60. The resistive heating element 77 may be powered by low voltage from a battery or a generator. By pulling on the snare device 76, the resistive heating element 77 applies energy to and cuts the sutures 60, releasing them from the magnetic anastomosis device for subsequent removal.

Figure 39B:
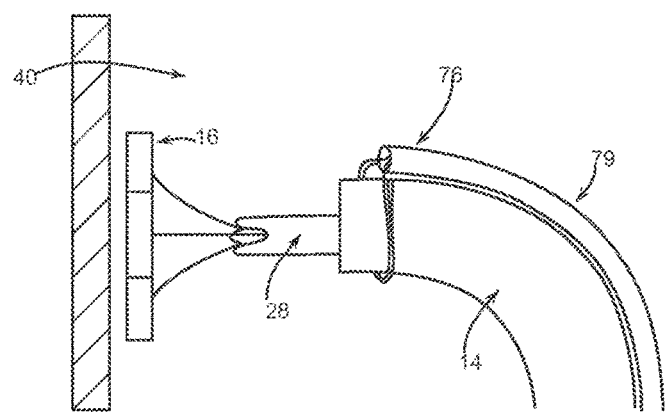
FIGS. 39B and 39C illustrate a snare device comprising a ring member having a cutting edge for cutting guide elements.

FIG. 39B illustrates a close-up view of the snare device 76. The snare device 76 may be positioned on the outside of a scope 14 or incorporated into a cap on the scope 14. The snare device 76 is contained within a snare sleeve 79. A deployment means or delivery needle 28 deploys the magnet 16 into the stomach 40. The snare device 76 is advanced in the snare sleeve 79 as shown in FIG. 39C.

Figure 39C:
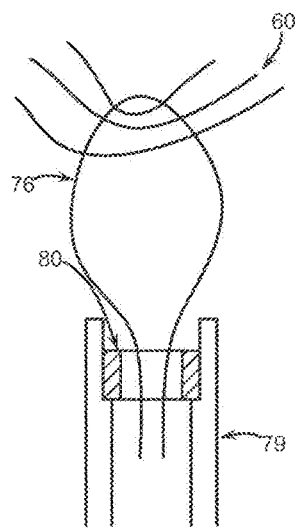

FIG. 39C illustrates a snare device 76 comprising a ring member 80 having a cutting edge for cutting guide elements 60. The snare device 76 captures the sutures 60 within the loop. By pulling back on the snare sleeve 79, the ring member 80 cuts the sutures 60, detaching them from the magnets 16 for subsequent removal.

Figure 39D:
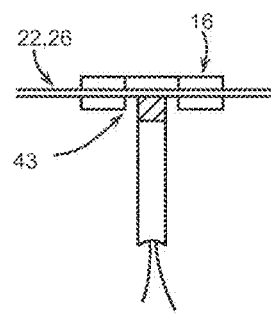
FIG. 39D illustrates a secondary device configured to provide suture or guide element cutting by way of monopolar/bipolar energy.

FIG. 39D illustrates a secondary device configured to provide suture 60 or guide element 30 cutting by way of monopolar/bipolar energy. Once the magnets 16 are in place on the tissues 22, 26, a monopolar/bipolar "hot" tip 43 is utilized to cut the sutures 60. The monopolar or bipolar tip 43 is activated upon pulling back on the delivery device 14.

Figure 40:
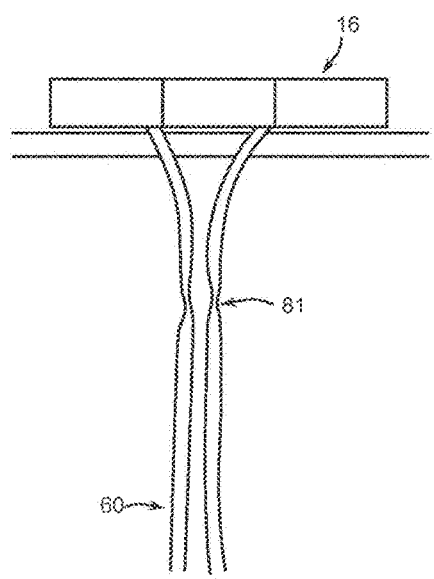
FIG. 40 illustrates breakaway guide elements or sutures.

FIG. 40 illustrates breakaway guide elements or sutures 60. The sutures 60 comprise a necked down or weakened portion 81. Upon pulling back on the sutures 60, the sutures 60 break away at the weakened point 81, detaching from the magnetic assembly 16 for subsequent removal of the sutures 60.

Figure 41:
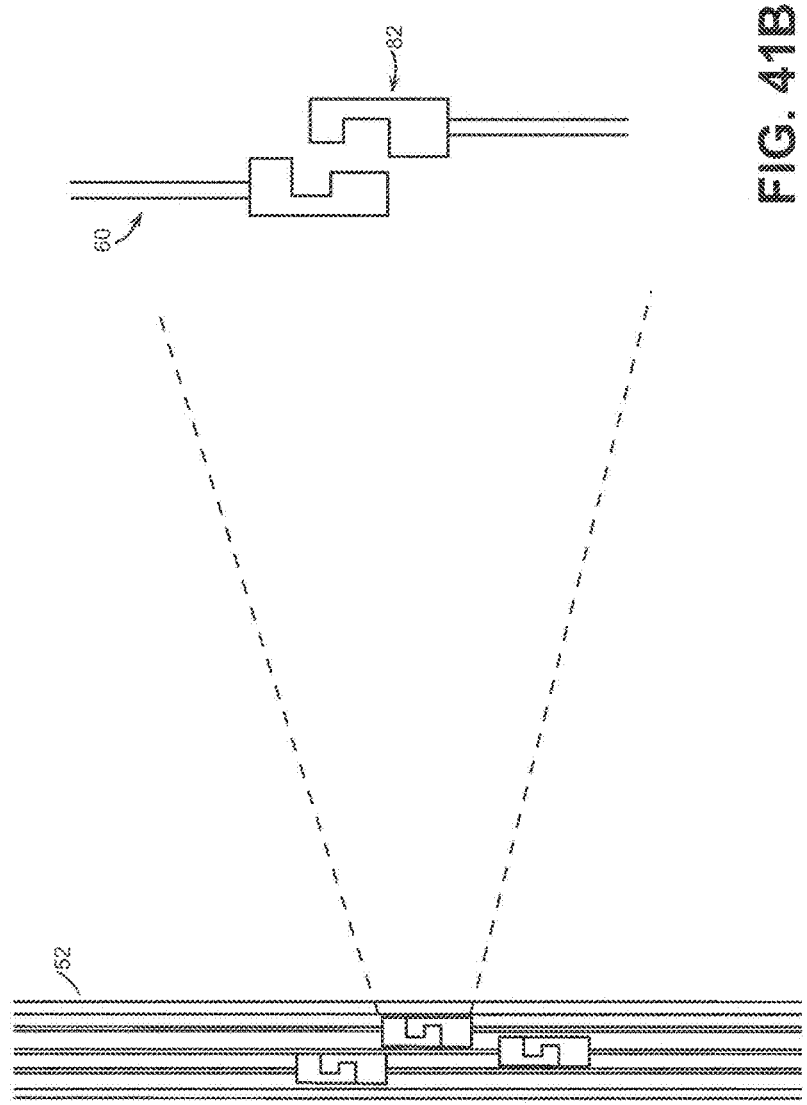
FIGS. 41A and 41B illustrate a detachable suture assembly.

FIGS. 41A and 41B illustrate a detachable suture 60 assembly. Within the sheath 52 of the delivery device 14, sutures comprising overmolded drivers 82 are stored in a staggered position as shown in FIG. 41A. In some embodiments, the sutures 60 comprising overmolded drivers 82 may be stored in individual lumens. The overmolded drivers 82 are stored in a constrained position within the sheath 52. Upon deployment by removing the sheath 52, the overmolded drivers are no longer constrained, and detach from one another, as shown in FIG. 41B. Upon the overmolded drivers 82 detaching, the sutures 60 may be removed from the patient.

Accordingly, exemplary embodiments provide improved devices and techniques for minimally invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer. More specifically, exemplary embodiments provide various systems, devices, and methods for the delivery, deployment, and positioning of magnetic compression devices at a desired site so as to improve the accuracy of anastomoses creation between tissues, organs, or the like.

Figure 42:
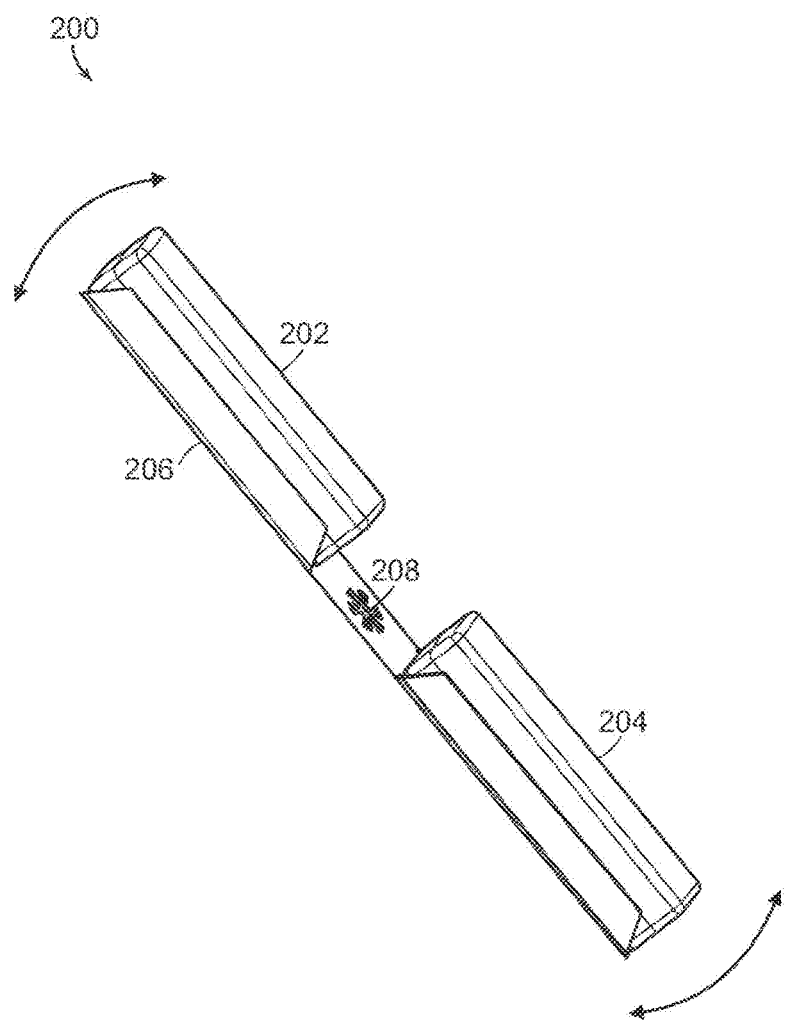
FIG. 42 illustrates a perspective view of another embodiment of a magnetic assembly consistent with the present disclosure.

FIG. 42 illustrates a perspective view of another embodiment of a magnetic assembly 200 consistent with the present disclosure. The magnetic assembly 200 comprises a pair of magnetic segments 202, 204 generally arranged in a linear alignment with one another (e.g., aligned in an end-to-end fashion) and coupled together via a flexible exoskeleton element 206. The segments 202, 204 are spaced apart via a central portion 108 of the exoskeleton 206. The central portion 208 may include a connection member for receiving a corresponding connection member of a placement device to assist in delivery of the magnetic assembly 200, as will be described in greater detail herein. The exoskeleton may be made from a resilient material that will retain its shape after deformation, such as a polymer or metal alloy. In some embodiments, the metal alloy will comprise nickel, such as nitinol. Exemplary exoskeleton embodiments are described in U.S. Pat. Nos. 8,870,898, 8,870,899, 9,763,664, the contents of each of which are incorporated by reference herein in their entirety.

The magnetic assembly 200 is configured to be delivered and deployed at a target site via a delivery device 100. As previously described, exemplary embodiments provide improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer. More specifically, exemplary embodiments provide a system including a delivery device 100 for introducing and delivering, via a minimally-invasive technique, a pair of magnetic assemblies 16a, 16b between adjacent organs to bridge walls of tissue 22, 26 of each organ together to thereby form a passage therebetween (i.e., an anastomosis). The delivery device 100 is particularly useful in delivering the pair of magnetic assemblies 16 to a target site within the gastrointestinal tract to thereby form anastomosis between gastric and gallbladder walls to provide adequate drainage from the gallbladder when blockage is occurring (due to disease or other health-related issues).

FIGS. 43A-43I illustrate various steps in deploying a pair of magnetic assemblies 200a, 200b to a target site for subsequent formation of anastomosis. In the embodiments described herein, the system generally includes a single scope, such as an endoscope 14, laparoscope, catheter, trocar, or other access device, through which a delivery device is advanced to a target site for delivering and positioning a pair of magnetic assemblies 200a, 200b for subsequent formation of anastomosis at the target site. In particular, the delivery device 100 comprises an elongate hollow body 102, such as a catheter, shaped and/or sized to fit within the scope. The delivery device includes a working channel in which a pair of magnetic assemblies 200a, 200b is loaded. The delivery device further includes a distal end 104 configured to pierce, or otherwise penetrate, through tissue.

Figure 43A:
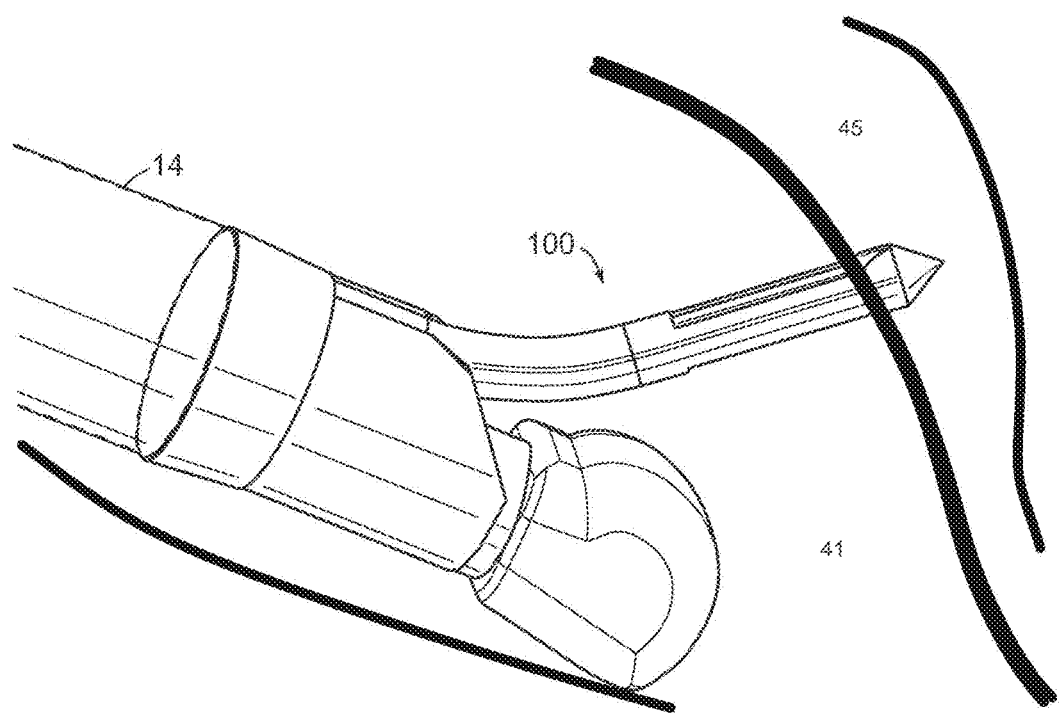
FIG. 43A illustrates advancement of a distal tip of a delivery device through respective tissue walls of adjacent organs at a target site for subsequent formation of an anastomosis therebetween.
Figure 43B:
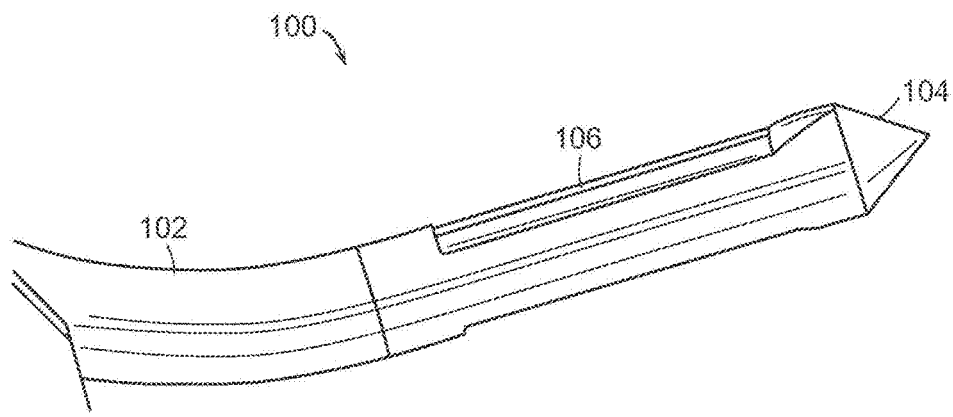
FIG. 43B is an enlarged view of a distal end of the delivery device illustrating the slot extending entirely through a side of the body of the delivery device.

For example, FIG. 43A illustrates advancement of a distal tip of a delivery device 100 through respective tissue walls of adjacent organs at a target site for subsequent formation of an anastomosis therebetween. For example, the distal end 104 may have a sharp tip for piercing tissue and/or may utilize energy to penetrate through tissue (i.e., a hot tip). The body 102 of the delivery device 100 further includes a slot or opening 106 adjacent to the distal end 104, as shown in FIG. 43B. As shown, the slot extends entirely through a side of the body 102 of the delivery device 100. The slot 106 is shaped and/or sized to receive the magnetic assemblies 200a, 200b therethrough, such that the magnetic assemblies 200a, 200b pass through the working channel and exit the delivery device 100 via the slot 106. The delivery device 100 further includes a placement member 108, generally in the form of a wire or the like, that is releasably coupled to one or both of the magnetic assemblies 200a, 200b and provides a means of deploying the magnetic assemblies 200a, 200b from the distal end of the delivery device 100 via the slot 106.

Figure 43C:
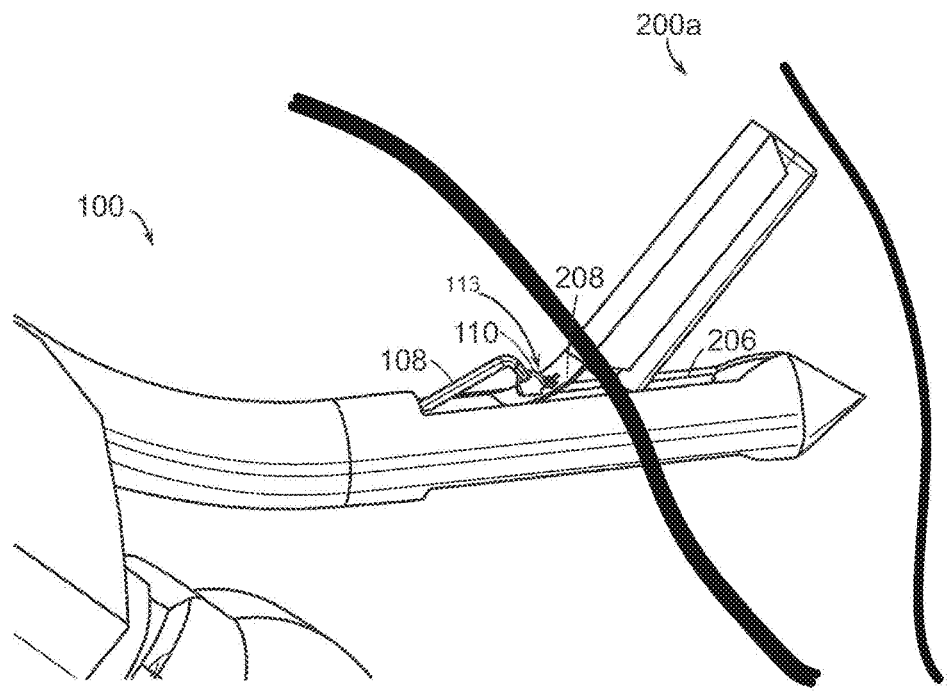
FIG. 43C illustrates delivery of a first magnetic assembly into a first organ.
Figure 43D:
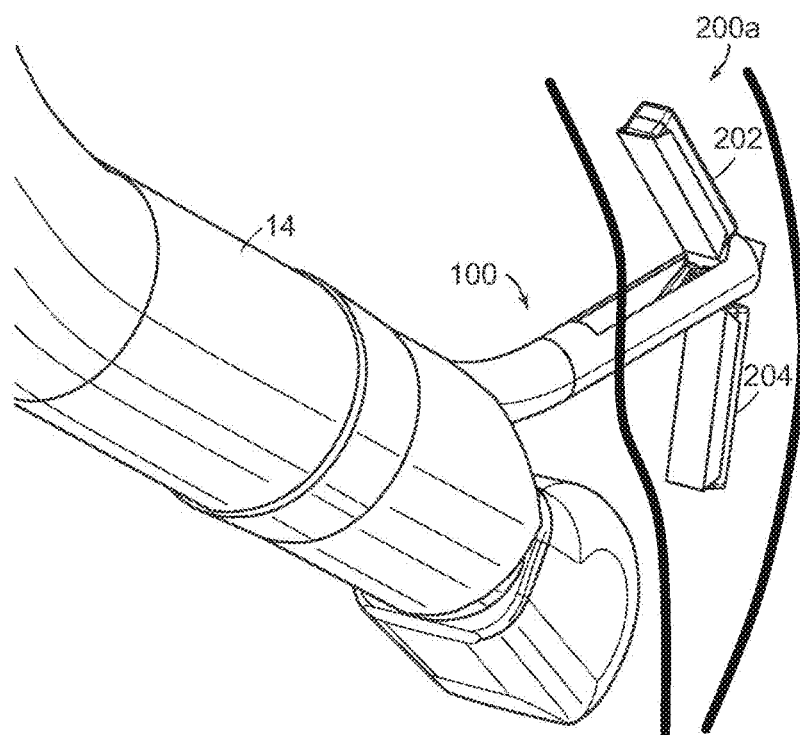
FIG. 43D illustrates deployment of the first magnetic assembly into the first organ while remaining retained within the slot of the delivery device.

During a procedure, a surgeon or other trained medical professional may advance a scope 14 (e.g., endoscope) within a hollow body of the patient and position the scope 14 at a desired anatomical location for formation of the anastomosis based on a visual depiction of the location of the target site as provided by an imaging modality 18 providing a medical imaging procedure (e.g., ultrasound (US), wavelength detection, X-ray-based imaging, illumination, computed tomography (CT), radiography, and fluoroscopy, or a combination thereof). The surgeon may advance the distal tip 104 of the delivery device 100 through adjacent walls of a pair of organs (i.e., through a wall of the duodenum 41 and a wall of the common bile duct 45), in any manner previously described herein. Upon advancing distal end 104, including the slot 106, into the first organ 45 (i.e., common bile duct), the surgeon may utilize the placement member 108 to manually deliver and deploy a first magnetic assembly 200a into the first organ 45 via the slot. For example, FIG. 43C illustrates delivery of a first magnetic assembly 200a into the common bile duct 45. As shown, the placement member 108 include a connection member 110, at attachment point 113, at a distal end of the placement member 108, which is configured to be releasably coupled to a corresponding connection member of the central portion 208 of the exoskeleton 206 (indicated by attachment point arrow). Upon advancing and extending the placement member 108 towards the distal end 104 of the delivery device 100, the first magnetic assembly passes from the working channel of the delivery device 100 and through the slot 106 to transition into a deployed state, as illustrated in FIG. 43D. As shown, deployment of the first magnetic assembly 200a results in the pair of magnetic segments 202, 204 to exit the slot 106 on opposite respective sides of the body 102 of the delivery device 100 while the central portion 208 of the exoskeleton 206 remains within the slot 106. In other words, the slot 106 extends entirely through the body 102 of the delivery device 100, from one side to the other. Accordingly, when in a deployed state, the first magnetic assembly 200a is positioned into the first organ while remaining retained within the slot 106 of the delivery device 100.

Figure 43E:
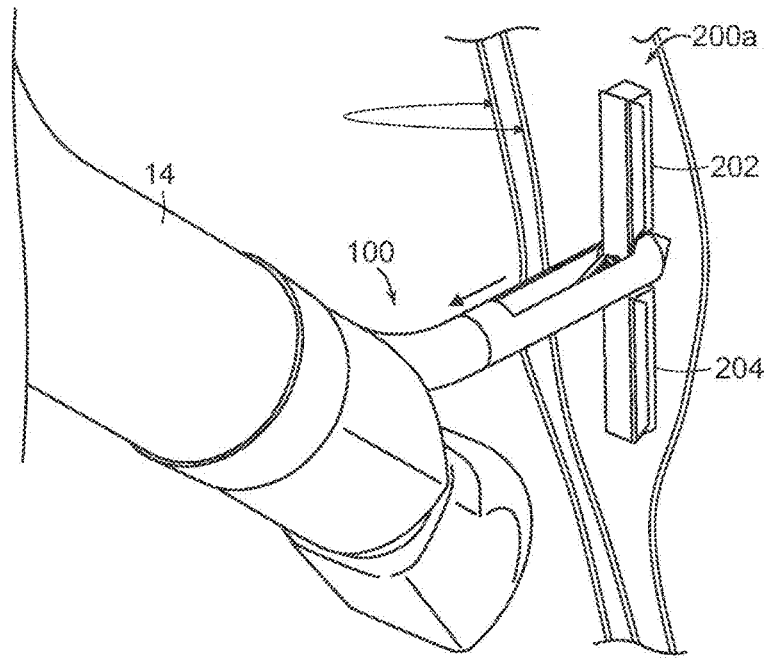
FIG. 43E illustrates a fully deployed first magnetic assembly within the first organ and pulling back of the delivery device to thereby draw the first magnetic assembly against a wall of the first organ in preparation for delivery and deployment of the second magnetic assembly in the second organ.

At this point, the surgeon need only pull back upon the delivery device 100 until the first magnetic assembly 200a engages the tissue of the first organ and the majority of the slot 106 is positioned within the second organ 41. The surgeon is able to then deliver and deploy the second magnetic assembly 200b into the second organ (i.e., the duodenum 41). FIG. 43E illustrates a fully deployed first magnetic assembly 200a within the first organ and pulling back of the delivery device 100 to thereby draw the first magnetic assembly 200a against a wall of the common bile duct in preparation for delivery and deployment of the second magnetic assembly 200b in the duodenum.

Figure 43F:
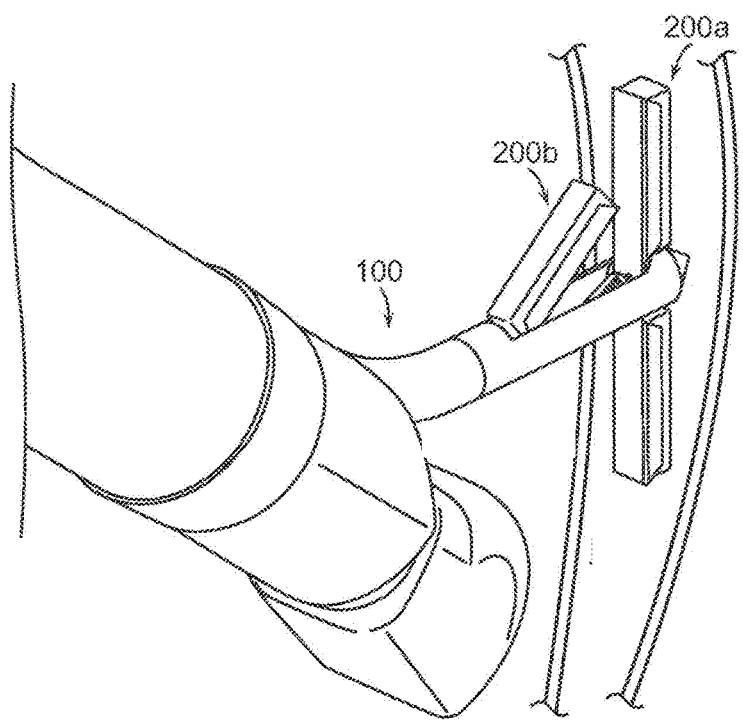
FIG. 43F illustrates delivery of the second magnetic assembly into the second organ.
Figure 43G:
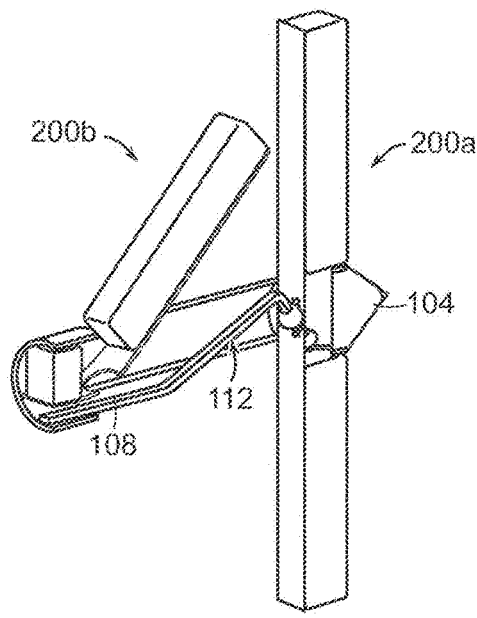
FIG. 43G is an enlarged view, partly in section, of the second magnetic assembly advancing to a deployed state.
Figure 43H:
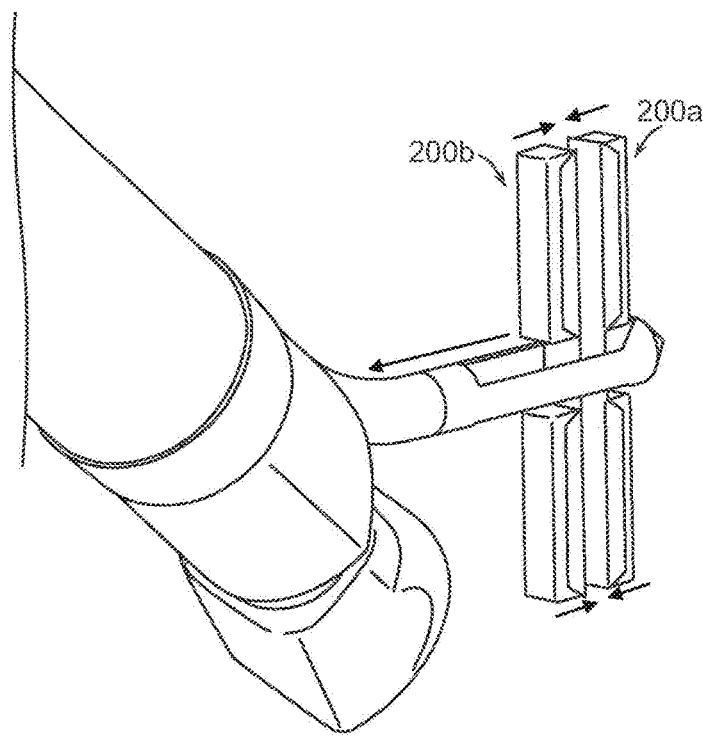
FIG. 43H illustrates the first and second magnetic assemblies in fully deployed states and coupled to one another as a result of attractive magnetic forces therebetween.

The second magnetic assembly 200b deploys in a similar fashion as the first magnetic assembly 200a, in that magnetic segments 202, 204 of the second magnetic assembly 200b exit the slot 106 on opposite respective sides of the body 102 of the delivery device 100 while a central portion 208 of an exoskeleton 206 remains retained within the slot 106. FIG. 43F illustrates delivery of the second magnetic assembly 200b into the duodenum. FIG. 43G is an enlarged view, partly in section, of the second magnetic assembly 200b advancing to a deployed state. As shown, as the second magnetic assembly 200b is advanced through the working channel and towards the slot 106, the assembly 200b is configured to engage a ramped section 112 of the placement member which assisted in directing at least one of the segments of the assembly 200b into place, as shown. FIG. 43H illustrates the first and second magnetic assemblies 200a, 200b in fully deployed states. The first and second magnetic assemblies 200a, 200b are substantially aligned with one another and, due to attractive magnetic forces, the first and second magnetic assemblies 200a, 200b will couple to one another.

Figure 43I:
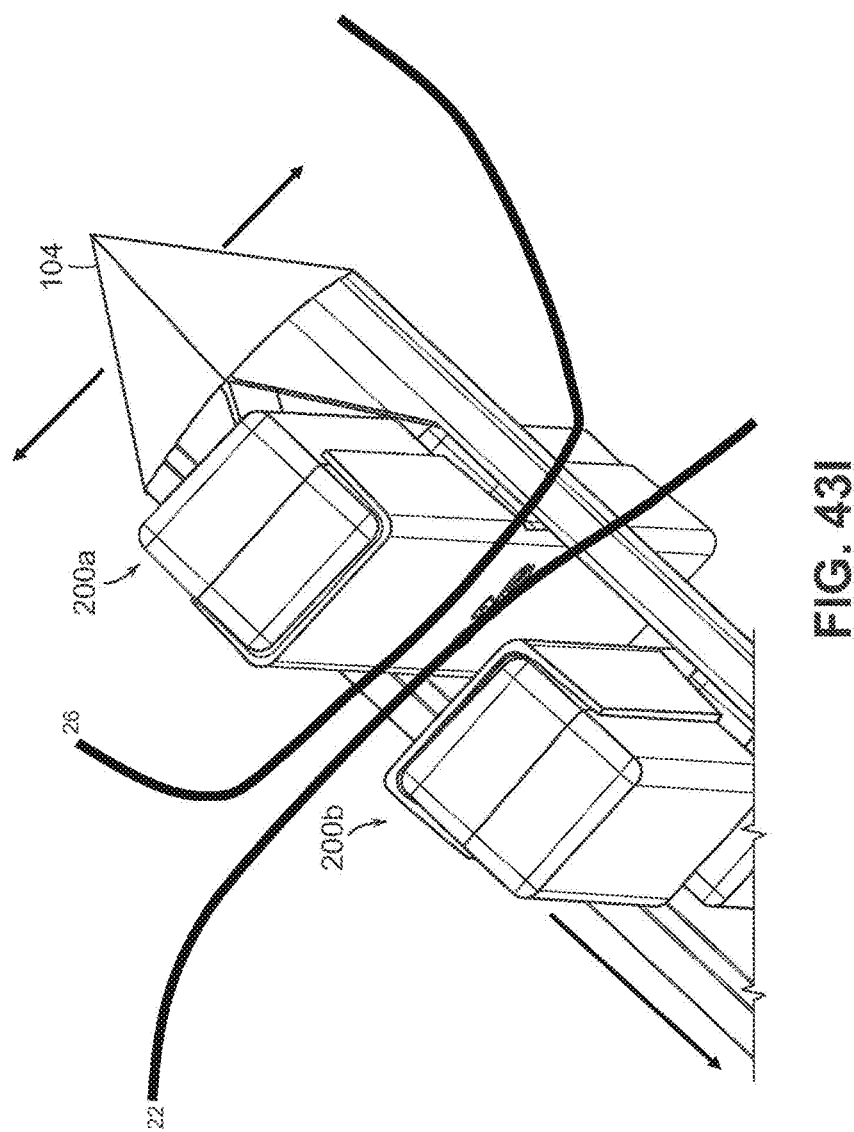
FIG. 43I illustrates the distal end of the delivery device constructed from two halves and configured to split apart to allow the delivery device to be removed from the target site while the pair of magnetic assemblies remain coupled to one another to form anastomosis at the target site.
Figure 44A:
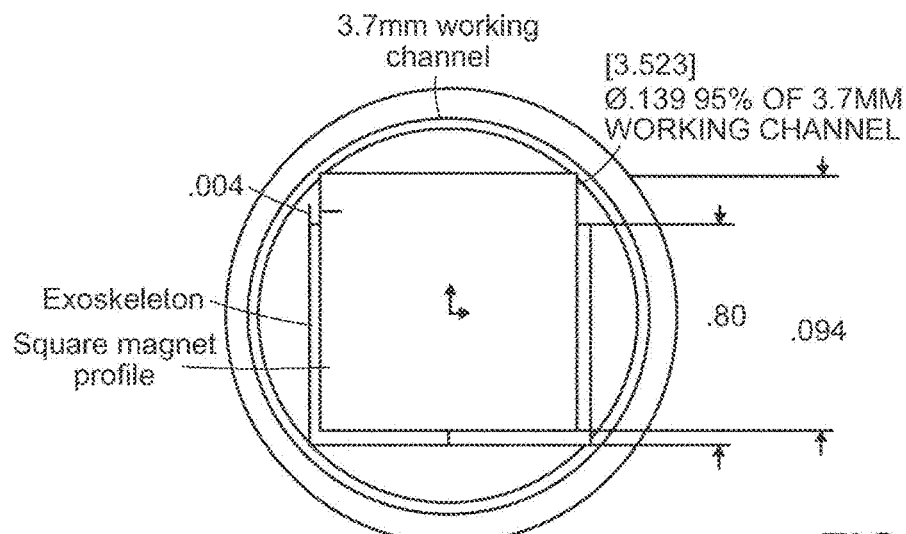
FIGS. 44A, 44B, 44C, and 44D are cross-sectional views of various profiles of magnet segments of magnetic assemblies within a working channel of a standard scope.
Figure 44B:
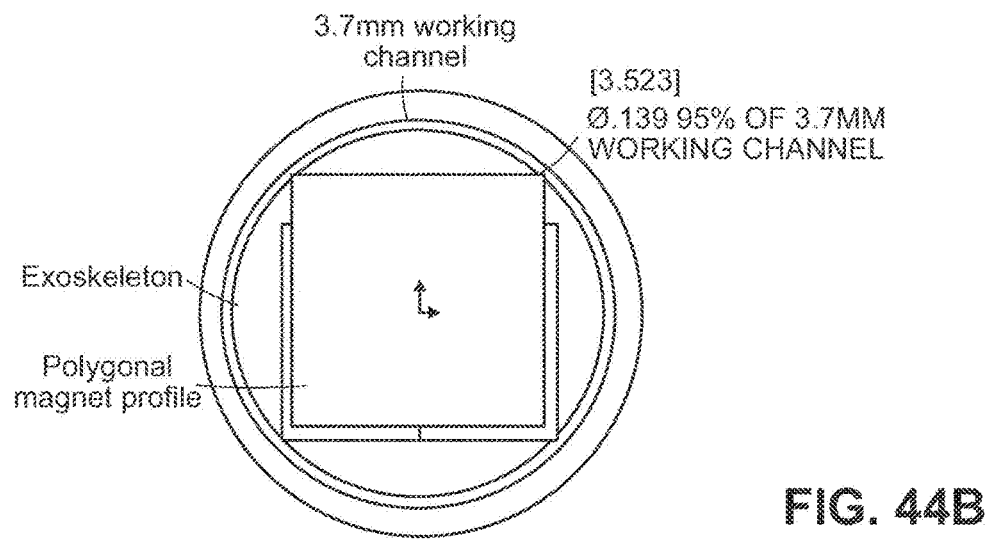
Figure 44C:
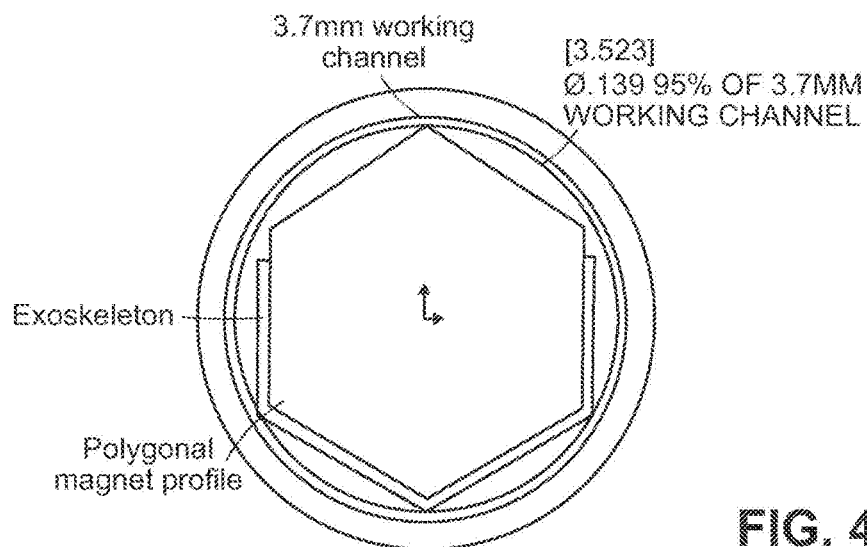
Figure 44D:
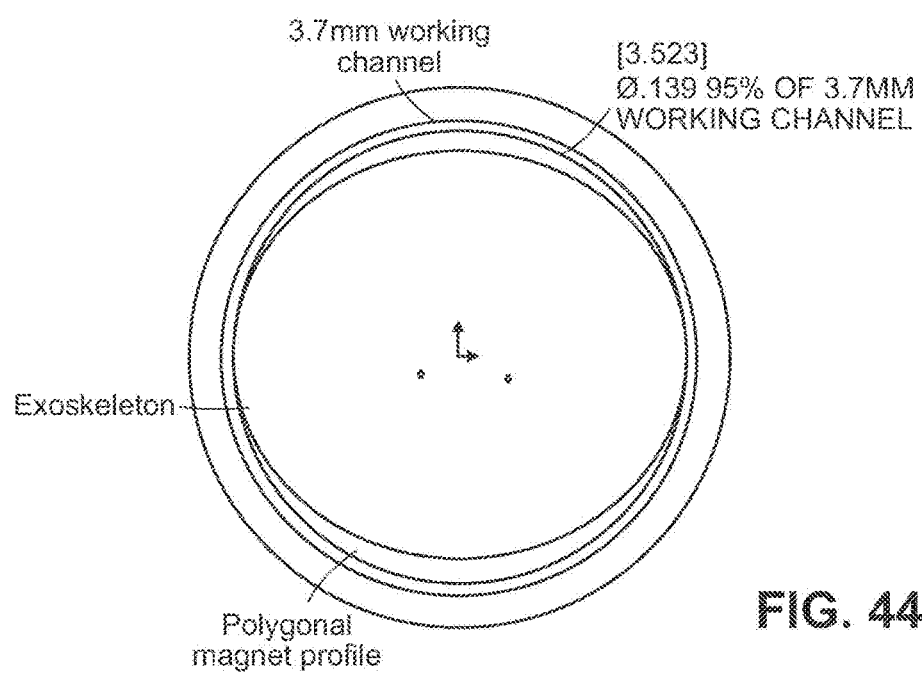

As shown in FIG. 43I, the distal end 104 of the delivery device 100 is comprised of two halves that, when in a default state, form a relatively uniform tip shape. However, the distal end comprises a deformable material (i.e., shape memory material), such that, upon application of sufficient force, the two halves will split apart. As such, once both the first and second magnetic assemblies 200a, 200b have been delivered and are effectively coupled to one another (but are still retained within the slot 106), the surgeon need only pull back on the delivery device 100 which then causes the magnetic assemblies 200a, 200b to make contact with the distal end 104 and force the two halves of the distal end 104 to split apart, allowing the distal end of the delivery device to be withdrawn from the target site while the pair of magnetic assemblies 200a, 200b remain in place. The pair of magnetic assemblies 200a, 200b compress the walls 22, 26 of each respective organ therebetween, subsequently forming an anastomosis between the organs (i.e., anastomosis between the duodenum and the common bile duct).

Upon deployment, each magnetic assembly has a width and a length generally corresponding to a width of a respective segment and a length that is approximately twice the length of each segment. As a result, the pair of magnetic assemblies, when coupled to one another, generally form a substantially linear package and the resulting anastomosis formed may generally be rectangular in shape, but may naturally form a round or oval shape. The resulting anastomosis may have a 1:1 aspect ratio relative to the dimensions of the magnetic assemblies. However, exemplary embodiments allow for larger aspect ratios (i.e., a larger anastomosis to form relative to the dimensions of the magnetic assemblies). In particular, prior art systems and methods that include the use of magnets for creating anastomosis are generally limited based on the dimensions of the working channel of the scope or catheter used for delivering such magnets, which, in turn, limits the resulting size of the anastomosis. The magnetic assembly design overcomes such limitations.

For example, the design of the magnetic assembly, notably the coupling of multiple magnetic segments 202 to one another via an exoskeleton 206, allow for any number of segments 202 to be included in a single assembly 16, and thus the resulting anastomosis has a greater size relative to the dimensions of the working channel of the scope 14. For example, in some embodiments, the resulting anastomosis may include an aspect ratio in the range of 2:1 to 10:1 or greater.

FIGS. 44A-44D are cross-sectional views of various profiles of magnet segments of magnetic assemblies within a working channel of a standard scope. The cross-sectional areas of magnets are illustrated, showing polygons as well as ellipses and circles taking between 10 and 95 percent of the annular space of the working channel. With the guide lines for the magnetic profile being in place, the next constraint for the device is the axial ratio of a minimum of 6:1 and a maximum of 50:1. This segmented length once assembled in the body can have either a regular or irregular shape.

FIG. 45 provides a listing of some exemplary working channel sizes considered usable/feasible to deploy a magnetic array with a cage to produce an anastomosis. These sizes do not limit future capabilities as scope channel sizes increase/decrease with market and device changes. The summary of sizing can be summarized into: 1.0 mm-6.0 mm (including a bleed scope called the "clot buster") with one particular sized device designed around the 3.7 mm.

Accordingly, the delivery device of the present disclosure produces a low-profile linear anastomosis that would allow certain complications, particularly those associated with blockage of the common bile duct, to be mitigated. In particular, patients experiencing a blockage of the common bile duct often undergo some sort of procedure to either remove the blockage or allow drainage to provide relief of jaundice/infection and hepatic portal complications. A common procedure is a sphincterotomy, or some sort of draining stent placement procedure. There are procedures which present decompression of the bile duct in a traditional way, but are not possible in a minimally noninvasive manner. Such procedures include, for example, a sphincterotomy, which is not possible due to inability to cannulate the common bile duct, inability to account for anatomical alterations, particularly when during heavily diseased states. Utilizing the magnetic closure force profile as described herein would allow minimal bleeding and create a semi-permanent slit profile. This slit profile would help to resist "sump syndrome" and help to create a drainage point which would remain effectively infection free.

Certain exemplary embodiments include a capture device (referred to below as a "cap") for the distal end of an endoscope or other delivery device 14 (e.g., laparoscope, catheter, etc.) that is configured for magnetically manipulating certain types of target devices within a hollow body (lumen) of a patient. Exemplary cap embodiments are described herein for use with compression anastomosis devices of the types described herein (e.g., self-assembling magnetic compression anastomosis devices 16), although it should be noted that caps additionally or alternatively can be configured or used for capturing other types of devices such as, for example and without limitation, annular devices, disk or spherical devices, linear or curvilinear devices, solid devices, hollow devices, signal devices, multiple devices, etc. Thus, references to a cap for use with compression anastomosis devices should be understood to include a cap for use with any such target devices.

Generally speaking, the target devices are magnetic (and sometimes referred to herein simply as a "magnet"), in which case the cap can include magnetic or magnetizable (e.g., metallic or electromagnetic) elements 85 that can magnetically capture the target device, either attached to or monolithically formed with the cap. Alternatively, the target devices may be non-magnetic but capable of being captured by a magnet, in which case the cap may include magnetic or electromagnetic elements 85 that can magnetically capture the target device.

In certain exemplary embodiments, the cap includes an articulating/folding capture element that allows the cap and any captured device to be presented at an angle, e.g., to enable easier insertion and/or translation through a lumen or body cavity and also allows a user to manipulate and align compression anastomosis devices 16 and change the presentation angle for transluminal mating, although it should be noted that many of the capture and release aspects described herein can be used with non-articulating caps. The cap may include a substantially clear material to permit viewing through the cap. The cap may be configured to utilize magnetic field sensing to capture, control, mate, and release compression anastomosis devices 16. In preferred embodiments, the device's sensing and holding forces are optimized to only release the compression anastomosis devices 16 when properly mated and to allow for improperly mated devices to be decoupled, realigned, and properly mated.

Figure 46:
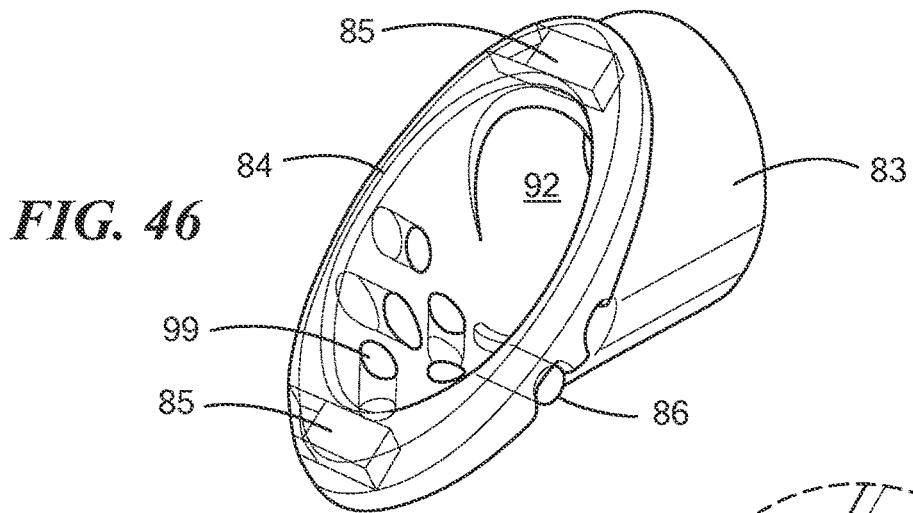
FIG. 46 is a schematic diagram showing a laparoscopic anastomosis capture device with ability to capture a compression anastomosis device and present it at an angle such as to allow for easier luminal translation, in accordance with one exemplary embodiment.

FIG. 46 is a schematic diagram showing an exemplary cap with the ability to capture a compression anastomosis device and present it at an angle such as to allow for easier luminal translation, in accordance with one exemplary embodiment. Here, the cap is depicted as a separate component that can be mounted to the distal end of an endoscope or other delivery device 14 (e.g., including a circumferential outer skirt for engaging a shaft or tube member such as an endoscope and preferably having a circumferential resilient material or other attachment mechanism for better clamping to the delivery device), although it should be noted that the cap alternatively can be integral to the distal end of an endoscope or other delivery device.

Figure 47:
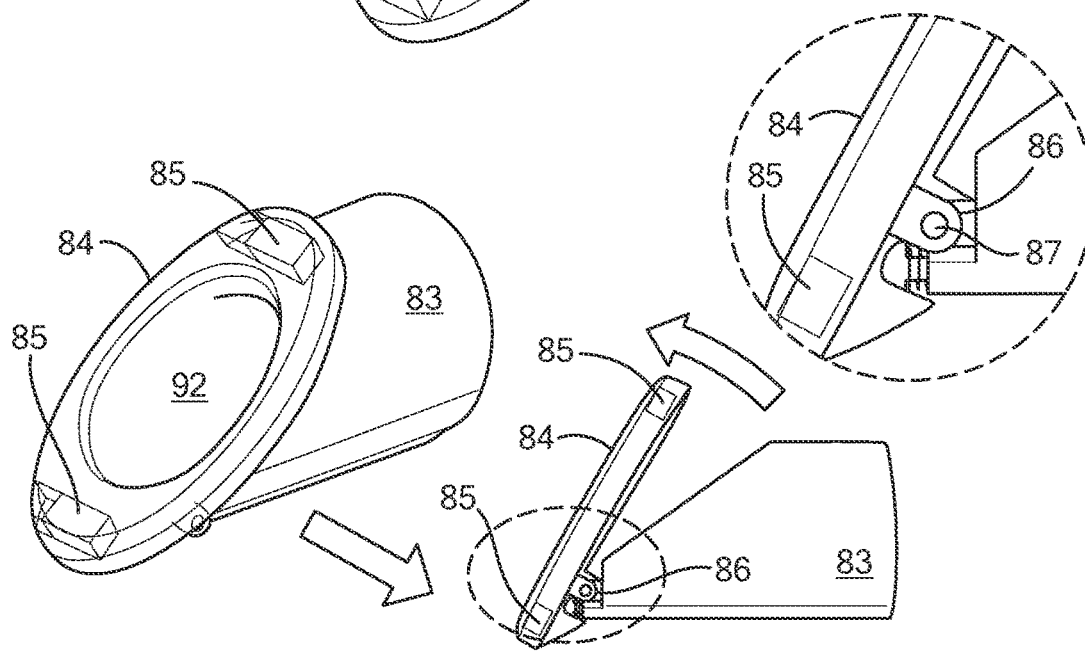
FIG. 47 is a schematic diagram showing a laparoscopic anastomosis capture device configured to pivot in response to pressure, in accordance with one exemplary embodiment.
Figure 48:
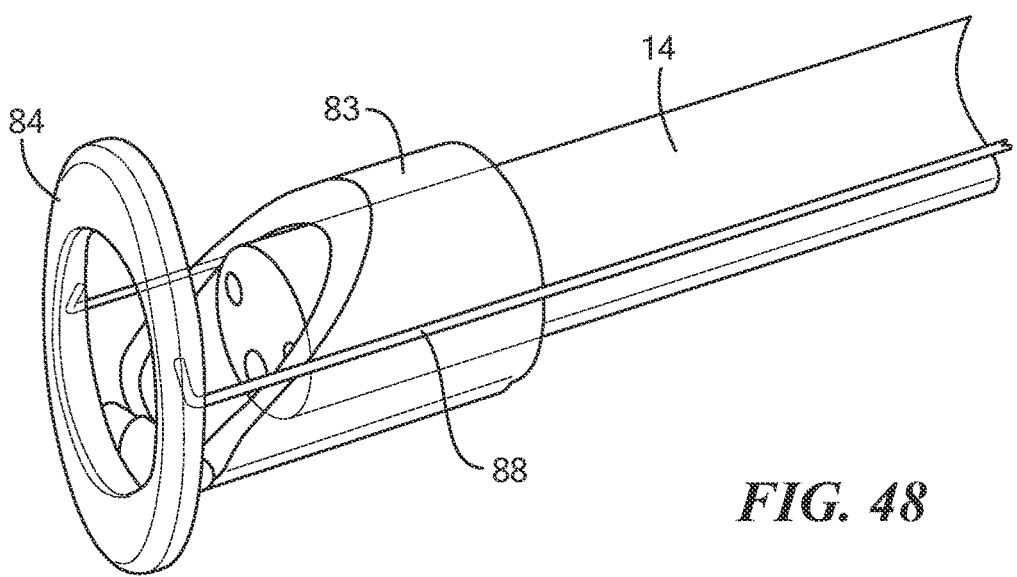
FIG. 48 is a schematic diagram showing a laparoscopic anastomosis capture device configured to pivot using guide lines, in accordance with one exemplary embodiment.

In this exemplary embodiment, the cap includes a cap body 83 having an angled distal end and an articulating cap element 84 (referred to herein as a "facia") coupled at the distal end of the cap body 83 and movable between at least a first or closed position in which the cap facia 84 is angled substantially with the distal end geometry (e.g., as depicted in FIG. 46) and a second or opened position in which the cap facia 84 is pivoted away from the cap body 83 (e.g., as depicted in FIGS. 47 and 48). The cap facia 84 may be coupled to the cap body 83 using an appropriate pivot mechanism 86 (e.g., one or more pins 87 as highlighted in FIG. 47, or a hinge, a ball-and-socket joint, etc.). The device may include a biasing mechanism such as to bias the cap facia toward the closed position (e.g., one or more springs as depicted in FIG. 47). In the examples of FIGS. 46-48, the cap facia 84 is configured to move between a closed position of approximately 45 degrees to an open position of approximately 90 degrees relative to the nominal plane of the endoscope or other delivery device 14, although alternative embodiments can be configured with other geometries (e.g., closing to less than 45 degrees and/or opening to greater than 90 degrees).

The cap facia 84 includes a mechanism for capturing a magnetic anastomosis device 16. In this example, the cap facia 84 includes one or more magnets 85 to capture a magnetic anastomosis device 16, although other mechanisms can be used in various alternative embodiments (e.g., mechanical or electromechanical devices that can grasp or otherwise retain the anastomosis device 16, an adhesive component that can secure the anastomosis device, etc.). It should be noted that magnets 85 can include electromagnets that can be configured to allow for providing fixed or variable magnetic field strengths such as, for example, to produce different magnetic field strengths for capturing, holding, and releasing compression anastomosis devices over a range of conditions (e.g., different device sizes, different device magnetic configurations, different tissue types/thicknesses, etc.).

In some embodiments, the cap body 83 may include channels 99 in order to pass fluid and/or air through the cap body 83. This may be done in order to maintain visibility through the cap body and/or maintain the suction of the endoscope 14.

In the example of FIG. 47, pressure applied at an extension at the bottom of the cap facia 84 causes the cap facia 84 to move from the closed position toward the open position relative to the cap body 83. This pressure can be caused, for example, from pushing the device against tissue or against another magnetic anastomosis device 16.

Additionally or alternatively, a force produced by interaction with an opposing magnetic anastomosis device 16 may cause the cap facia 84 to move from the closed position toward the open position relative to the cap body 83, such as, for example, when a first magnetic anastomosis device being delivered interacts with a previously delivered magnetic anastomosis device as the distance between the two magnetic anastomosis devices decreases.

Additionally or alternatively, the cap may include an actuation mechanism for controlling the position of the cap facia 84 relative to the cap body 83. FIG. 48 depicts one type of actuation mechanism including control guides 88 that can be operated to control the position of the cap facia 84, although other mechanisms can be used in various alternative embodiments (e.g., mechanical, electromechanical, etc.).

Figure 49:
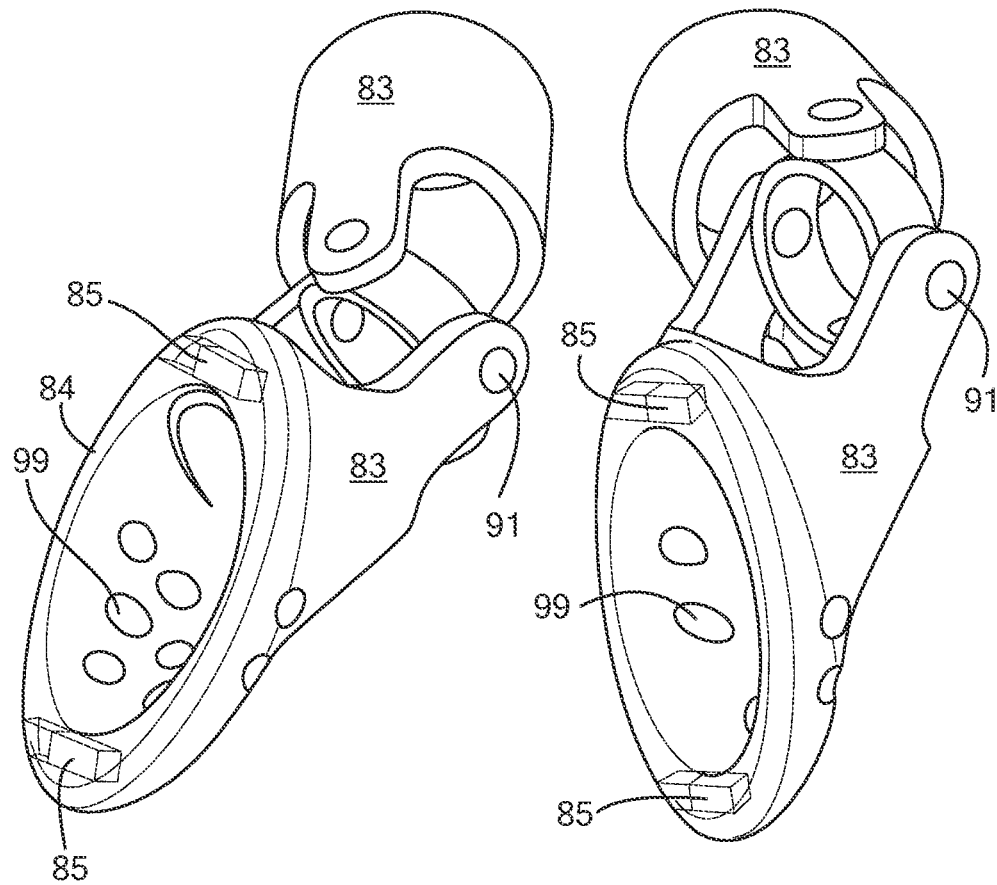
FIG. 49 is a schematic diagram showing a laparoscopic anastomosis capture device including a universal joint providing additional degrees of freedom, in accordance with one exemplary embodiment.

In certain exemplary embodiments, the cap additionally or alternatively may be configured to allow for greater degrees of movement. FIG. 49 depicts a universal joint 91 comprising articulating hinges to provide three degrees of freedom, although other mechanisms can be used in various alternative embodiments (e.g., a hinge, a ball-and-socket joint, etc.). It should be noted that any included actuation mechanism generally would allow for control of the cap position and movement through any desired range of motion.

As shown, for example, in FIG. 46, the cap 83 and facia 84 may provide an opening 92 to allow material or fluid to through the cap and also prevent visual or material obstruction when coupling the anastomosis device 16 or otherwise creating the anastomosis.

As discussed above, in preferred embodiments, the device's sensing and holding forces are optimized to only release or allow the release of the compression anastomosis device when properly mated and to allow for improperly mated devices to be decoupled, realigned, and properly mated. Thus, generally speaking, the cap is configured to have a predetermined holding force with regard to a particular compression anastomosis device 16, and this predetermined holding force can be configured or otherwise selected such that the compression anastomosis device 16 can be released only when the coupling force through coupling with another compression anastomosis device 16 is greater than the holding force. Once the coupling force is greater than the holding force, the compression anastomosis device 16 could release from the cap automatically or when the delivery device 100 is retracted. The holding force can be controlled in any of various ways, such as, for example and without limitation, the number of magnets or metallic elements 85 on the cap, the size of magnets or metallic elements 85 on the cap, the strength of magnets 85 on the cap, the cap/facia 84 material, the manner in which one or more magnets or metallic elements 85 are secured by the cap/facia (e.g., attached to the cap, embedded in the cap, etc.), to name but a few. The coupling force in turn can be affected by a number of factors including, without limitation, the configuration of the compression anastomosis devices 16, tissue type/thickness, blood flow or perfusion, etc. Exemplary embodiments can include different caps with different configurations and sizes (e.g., outer diameters) for use with different target devices, tissue type/thicknesses, etc. In these exemplary embodiments, the magnetic sensing can be considered passive, as it is based on the configurations and interactions of the cap and compression anastomosis devices 16.

Additionally or alternatively, the holding force can be accomplished using mechanical or electromechanical components (e.g., grasping elements), adhesive, or other components that hold the compression anastomosis device 16 unless and until the coupling force is greater than a predetermined level e.g., overcoming the holding force or otherwise releasing the holding mechanism. For example, the coupling force could be actively sensed (e.g., using a magnetic sensor, force sensor, etc.) and used to release the compression anastomosis device 16 (e.g., mechanically or electromechanically such as by opening grasping elements or physically separating the compression anastomosis device 16 from the cap). Thus, for example, the compression anastomosis device 16 could be release when the magnetic field is detected at greater than X gauss. In certain exemplary embodiments, the cap additionally or alternatively can include one or more sensors (e.g., thin film sensors) to measure and detect different parameters such as force, pressure, and/or magnetic induction, e.g., as it pertains to coupling between compression anastomosis devices. This can be used for providing feedback to the user in real time. The feedback may also include light, sound, screen, and/or other indicators.

Figure 50:
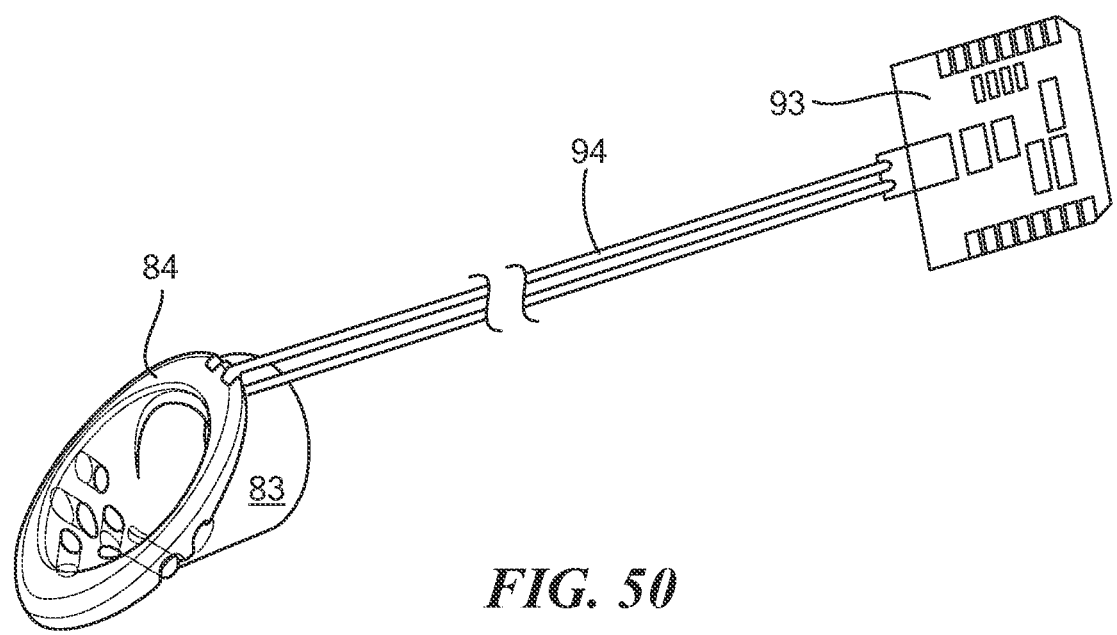
FIG. 50 is a schematic diagram showing a cap with one or more sensors that are in communication with an electronic interface through which feedback can be provided to the user, in accordance with one exemplary embodiment.

FIG. 50 is a schematic diagram showing a cap with one or more sensors that are in communication with an electronic interface 93 through which feedback can be provided to the user, in accordance with one exemplary embodiment. It should be noted that a similar mechanism can be used with electronic actuators on the cap to electronically control, for example, the position and movements of the cap and/or the amount of capture force (e.g., for capturing and releasing a magnetic anastomosis device). Thus, for example, certain embodiments can include one or more electronic sensors and/or one or more electronic actuators. It should be noted that such sensors and/or actuators can be used in certain exemplary embodiments in addition to, or in lieu of, an angled and/or movable cap. In one embodiment the cap may have a thin film sensor on the cap facia 84 to measure and/or detect one or more parameters such as force, pressure, and/or magnetic induction. This can be used for feedback for the user in real time. For example, a thin film strain gauge 94 may transfer data on one or more parameters to the electronic interface 93 as feedback to the user. The feedback may also include light, sound, screen, and/or other indicators.

Figure 51:
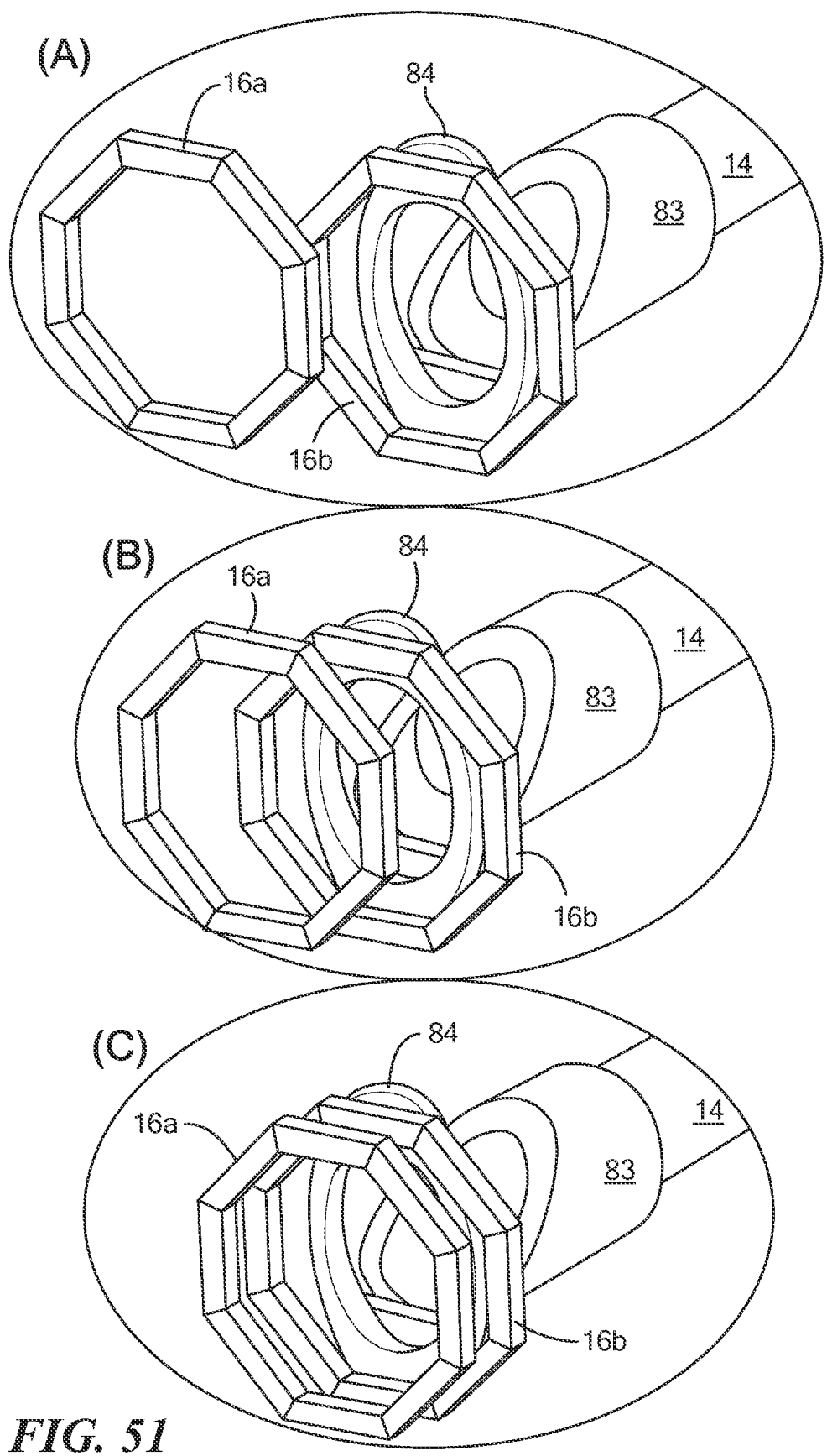
FIG. 51 is a schematic diagram showing conditions detected by a sensor system, in accordance with one exemplary embodiment.

Without limitation, sensor systems of the types described above can be used to monitor the position of the captured anastomosis device relative to a corresponding anastomosis device such as for notifying the user and/or preventing releasing of the captured anastomosis device 16*b* when the anastomosis device 16*b* is not adequately positioned for mating with a corresponding anastomosis device 16*a*. For example, in certain exemplary embodiments, the sensor system can be configured to detect conditions of the types depicted in FIG. 51, e.g., (A) Magnets 16*a*, 16*b* are in a "Venn Diagram" arrangement; (B) Magnets 16*a*, 16*b* are in a "Figure Eight" arrangement; or (C) Magnets 16*a*, 16*b* are separated by more than a predetermined distance (e.g., more than around 4 mm) such as, for example, due to tissue thickness or obstruction. Sensing can be accomplished, for example, by force, pressure, and/or magnetic induction measurements.

Figure 52:
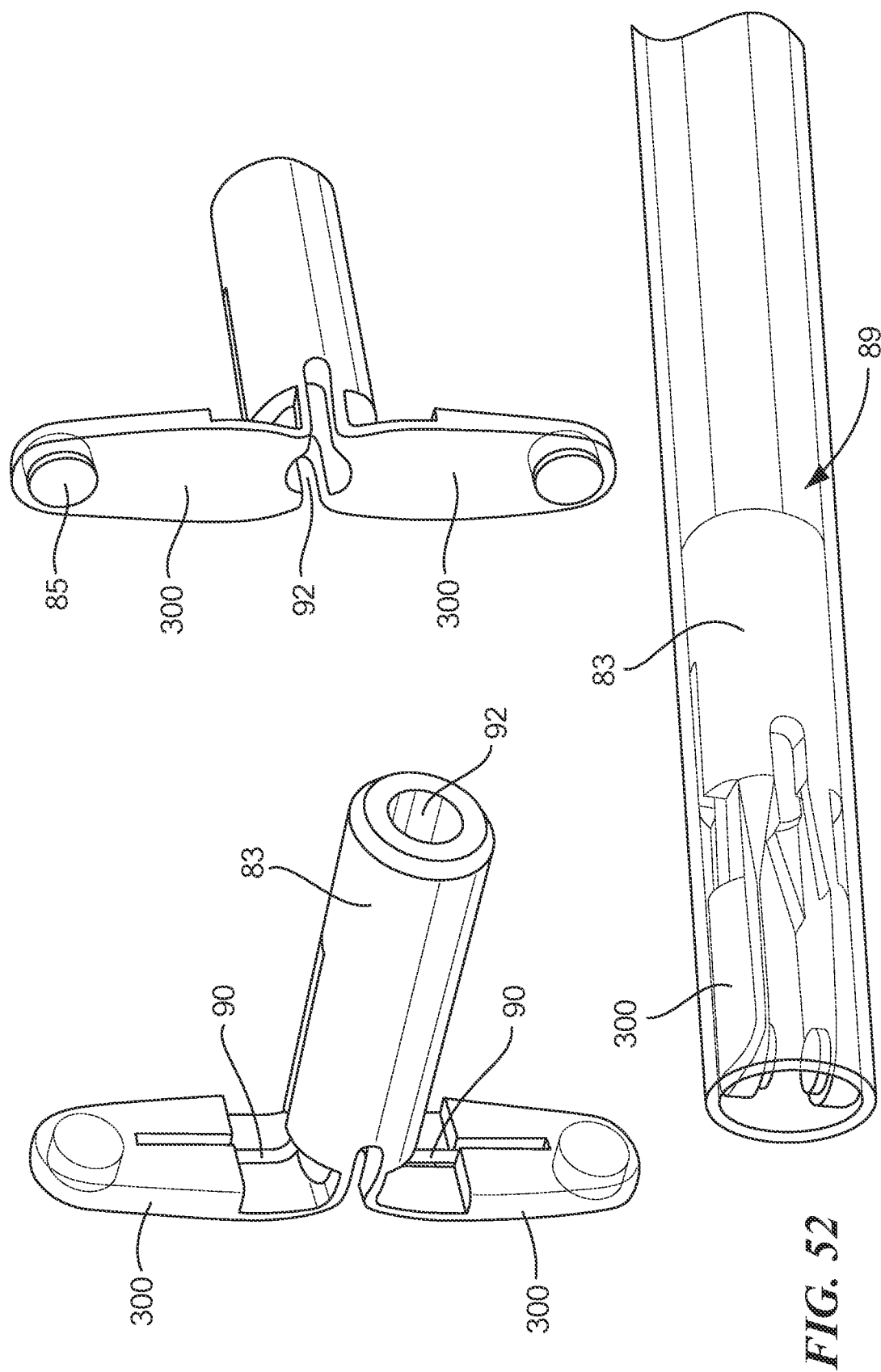
FIG. 52 is a schematic diagram showing an alternative cap configuration in which the cap is configured (e.g., spring-loaded) to open when extended from the shaft member opening, in accordance with one exemplary embodiment.

FIG. 52 shows an alternative cap configuration in which the cap is configured (e.g., spring-loaded 90) to open when extended from the shaft member 89 opening. This exemplary embodiment includes two opening or spring members 90, although it should be noted that alternative embodiments can include more than two opening members (e.g., three, four, etc.). The exemplary cap of FIG. 52 includes one or more arms 300 (while two arms are shown, one arm or more is possible) for capturing an anastomosis device. The cap has a working channel 92 throughout its length to allow magnetic device 16 and other material to flow through the cap. In one embodiment, the cap is stored at a 180 degree angle relative to the scope 14. Upon exiting the shaft member 83, the cap opens perpendicular to the scope 14 in order to capture an anastomosis device 16. The arms can be opened by spring loaded members 90 or other actuating members that allow the cap to open to an angle of 90 degrees. The cap shown in FIG. 52 can include any of the elements described above, e.g., magnets 85 or other mechanism for capturing an anastomosis device, selective sensing and release of the anastomosis device based on the coupling force, a pivoting mechanism to allow the captured anastomosis device to be presented at an angle after capture, a universal joint or other mechanism providing additional degrees of freedom, actuators for controlling the position and movement of the cap, and/or electronic sensors and/or actuators.

FIGS. 54A-54J show an exemplary flexible and manipulable delivery device having an angled cap at the distal end for selectively delivering, capturing, and releasing a magnetic compression anastomosis device, in accordance with one exemplary embodiment.

FIG. 54A shows the device prior to deployment of the compression anastomosis device. In this example, the cap facia 84 includes two magnets 85 for capturing a deployed compression anastomosis device or other device. In this example, the cap facia 84 is stored at a 45 degree angle to the delivery device such as an endoscope 14.

Figure 54B:
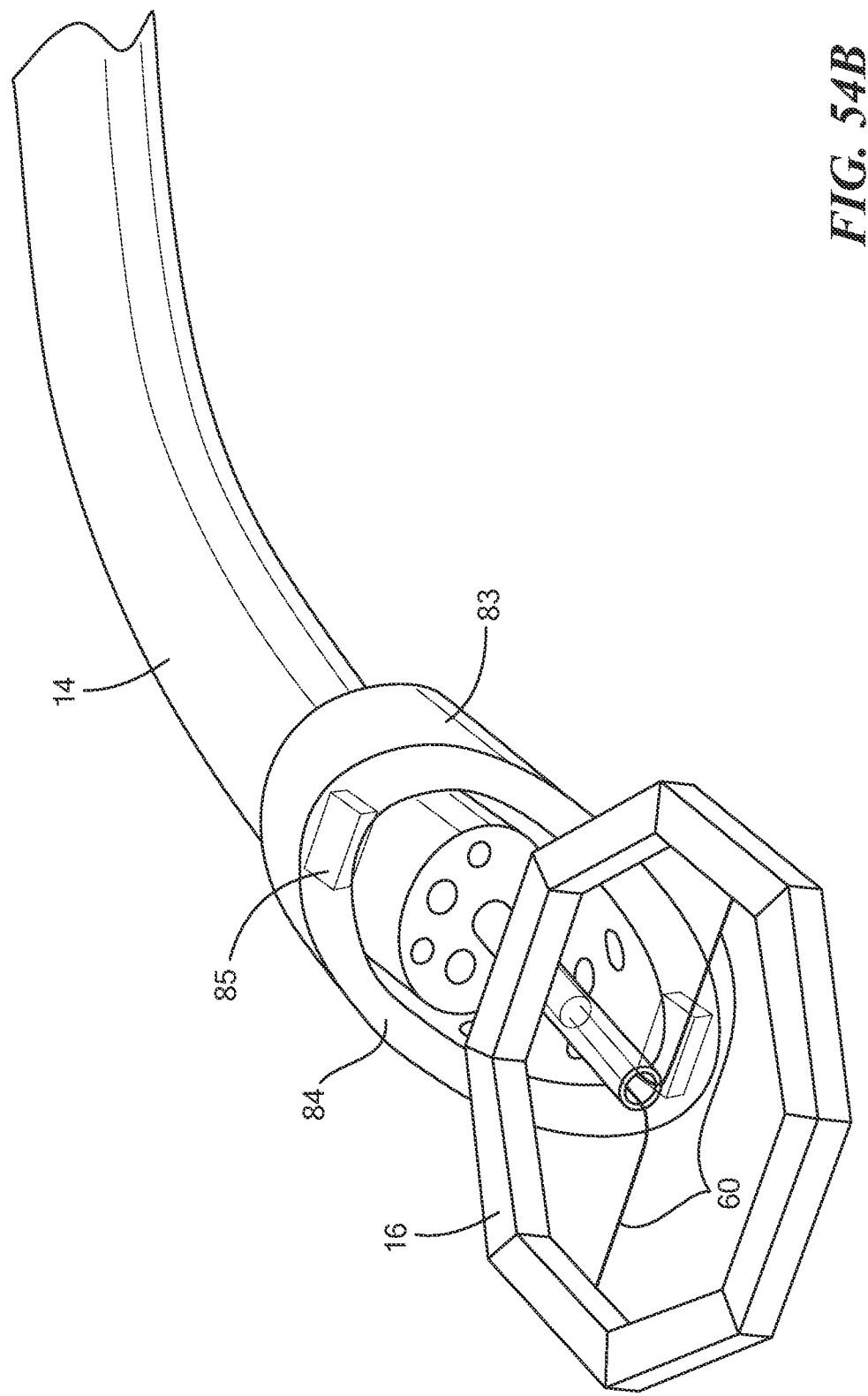

FIG. 54B shows the device after deployment and self-assembly of the compression anastomosis device 16. The magnetic anastomosis device 16 is deployed from the delivery device 14 through the hole in the cap facia 84. The magnet self-assembles into a polygonal shape, in this example an octagon, and is attached to the scope by sutures 60 or another control wire. At this point, the magnet 16 is not yet aligned or engaged with the cap facia 84.

Figure 54C:
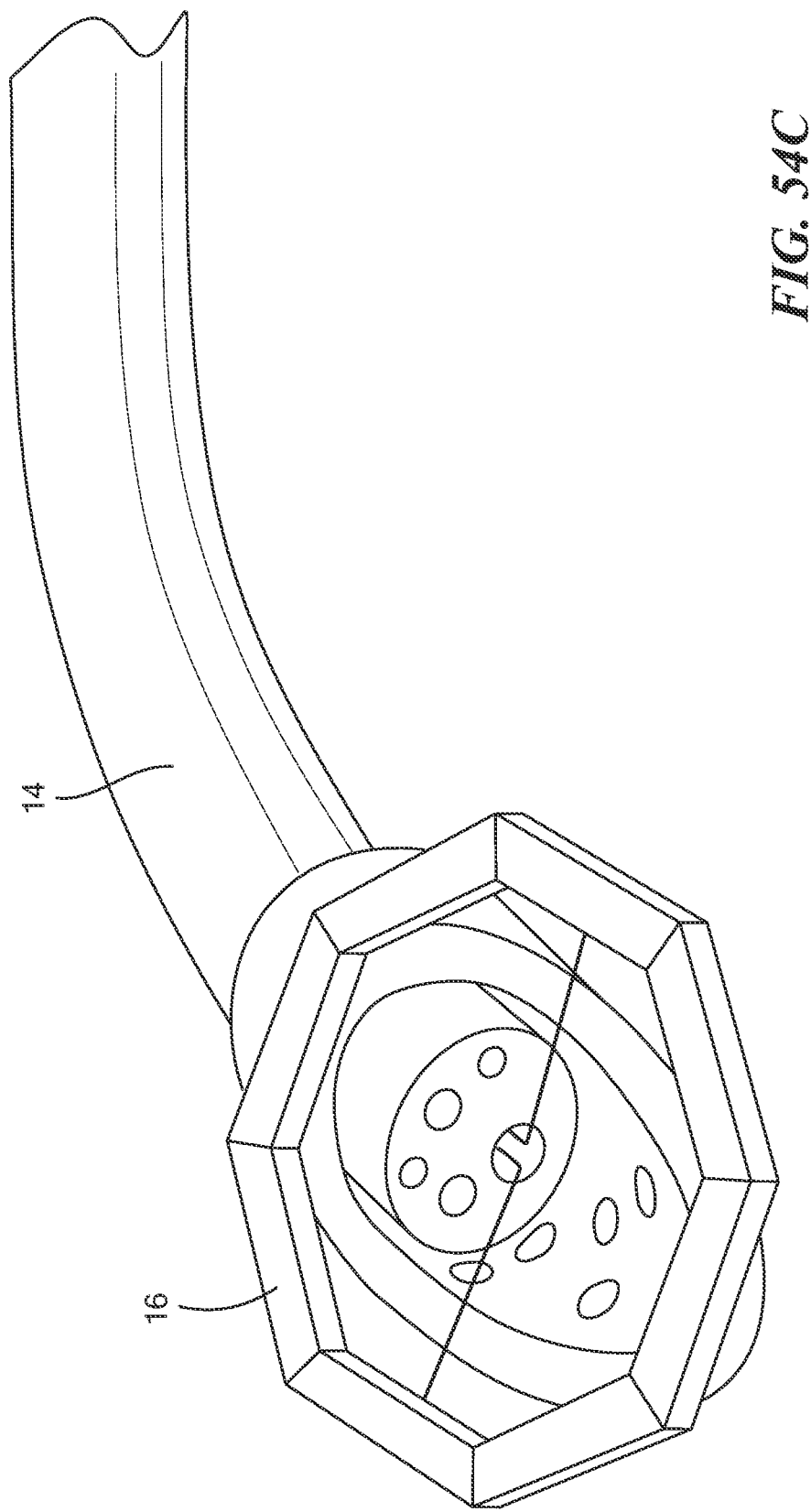

FIG. 54C shows the compression anastomosis device 16 captured by the magnets on the angled cap. The magnetic anastomosis device 16 is attracted to the cap facia 84 by attractive magnetic forces from the magnetic devices 85 on the cap facia 84. The magnets 85 on the cap facia 84 attract the magnetic anastomosis device 16 and mate it to the cap facia 84 for manipulation and placement. The anastomosis device 16 may also be brought to the cap facia 84 by pulling back on the sutures 60 attaching the magnetic device 16 to the scope 14.

FIGS. 54D-54H show a sequence of movements of the flexible delivery device as induced by an operator at the proximal end of the delivery device demonstrating both vertical, horizontal, and rotational displacements of the distal end with captured compression anastomosis device.

Figure 54D:
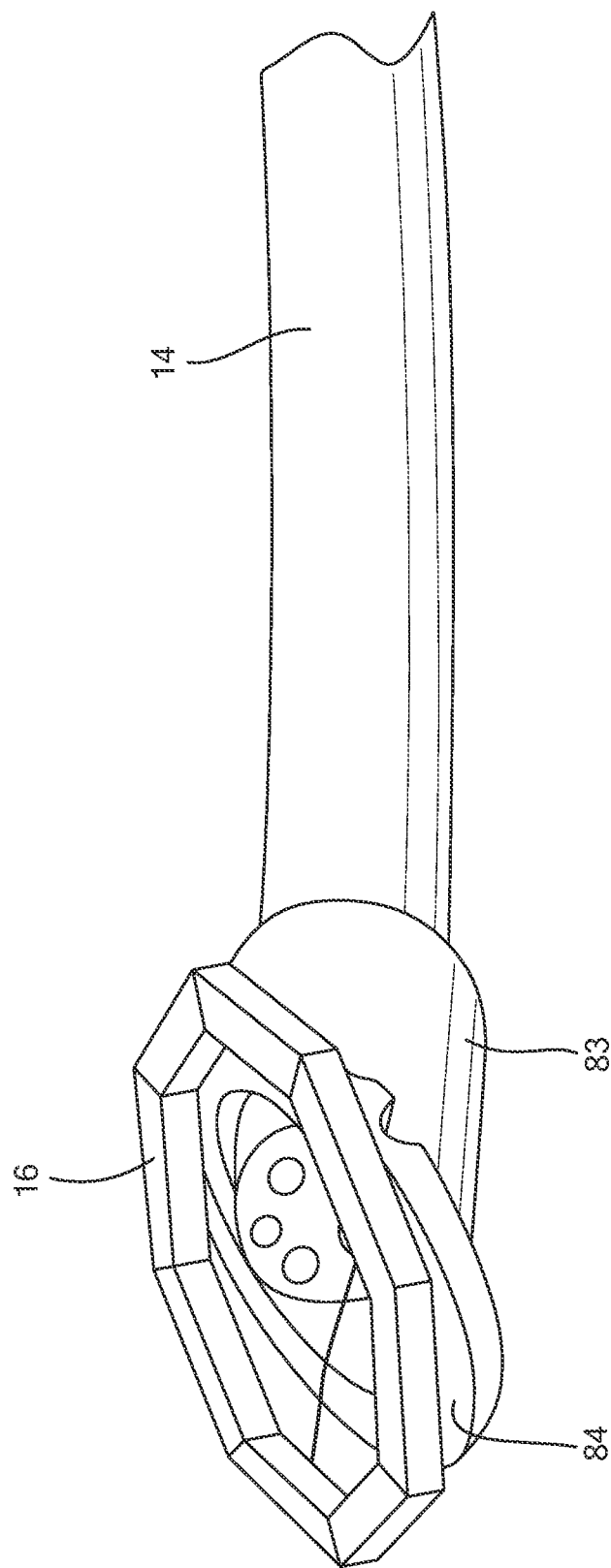

FIG. 54D shows the magnetic anastomosis device 16 coupled to the cap facia 84 with the cap facia 84 in the stored position of 45 degrees to the endoscope 14.

Figure 54E:
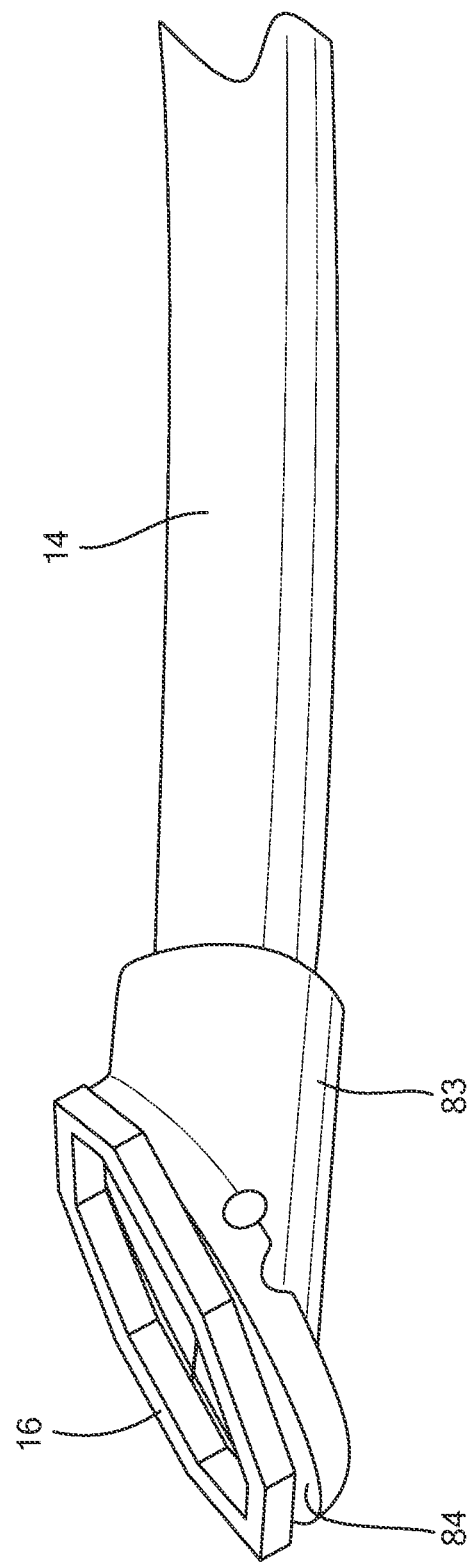

FIG. 54E shows a side-view of the magnetic anastomosis device 16 coupled to the cap facia 84 in the stored position of 45 degrees to the endoscope 14. In some embodiments, the cap facia 84 may be stored at angles other than 45 degrees such as perpendicular to the endoscope 14 or to an angle less than 45 degrees.

Figure 54F:
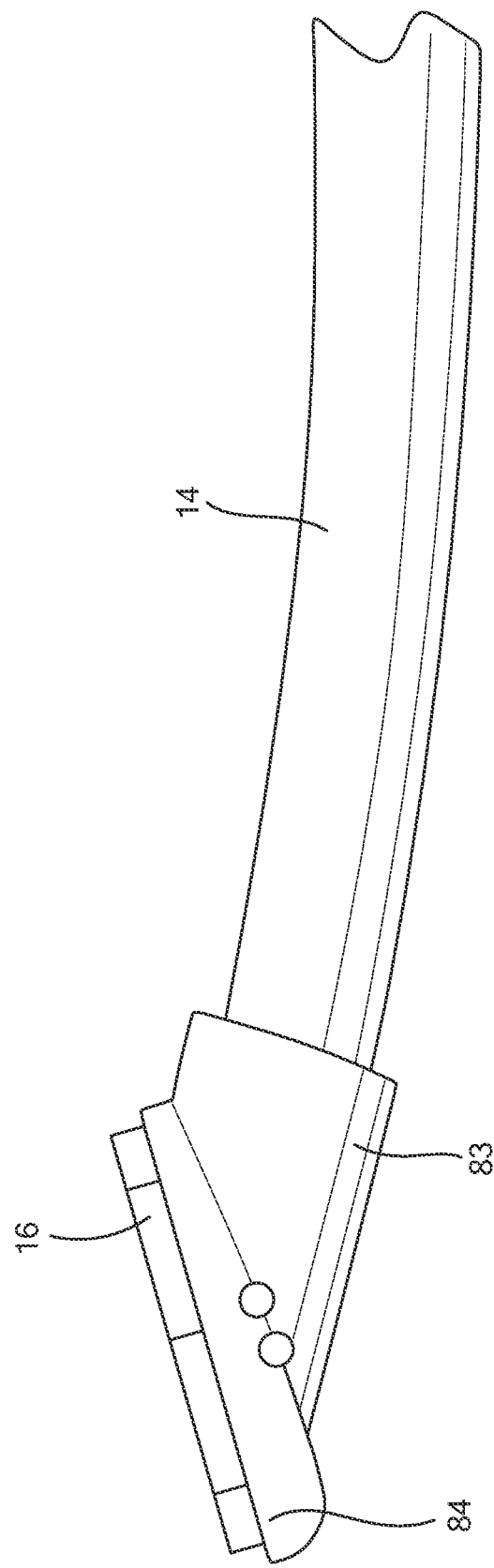

FIG. 54F shows another side-view of the anastomosis device 16 coupled to the cap facia 84 in the stored position 45 degrees to the end of the endoscope 14.

Figure 54G:
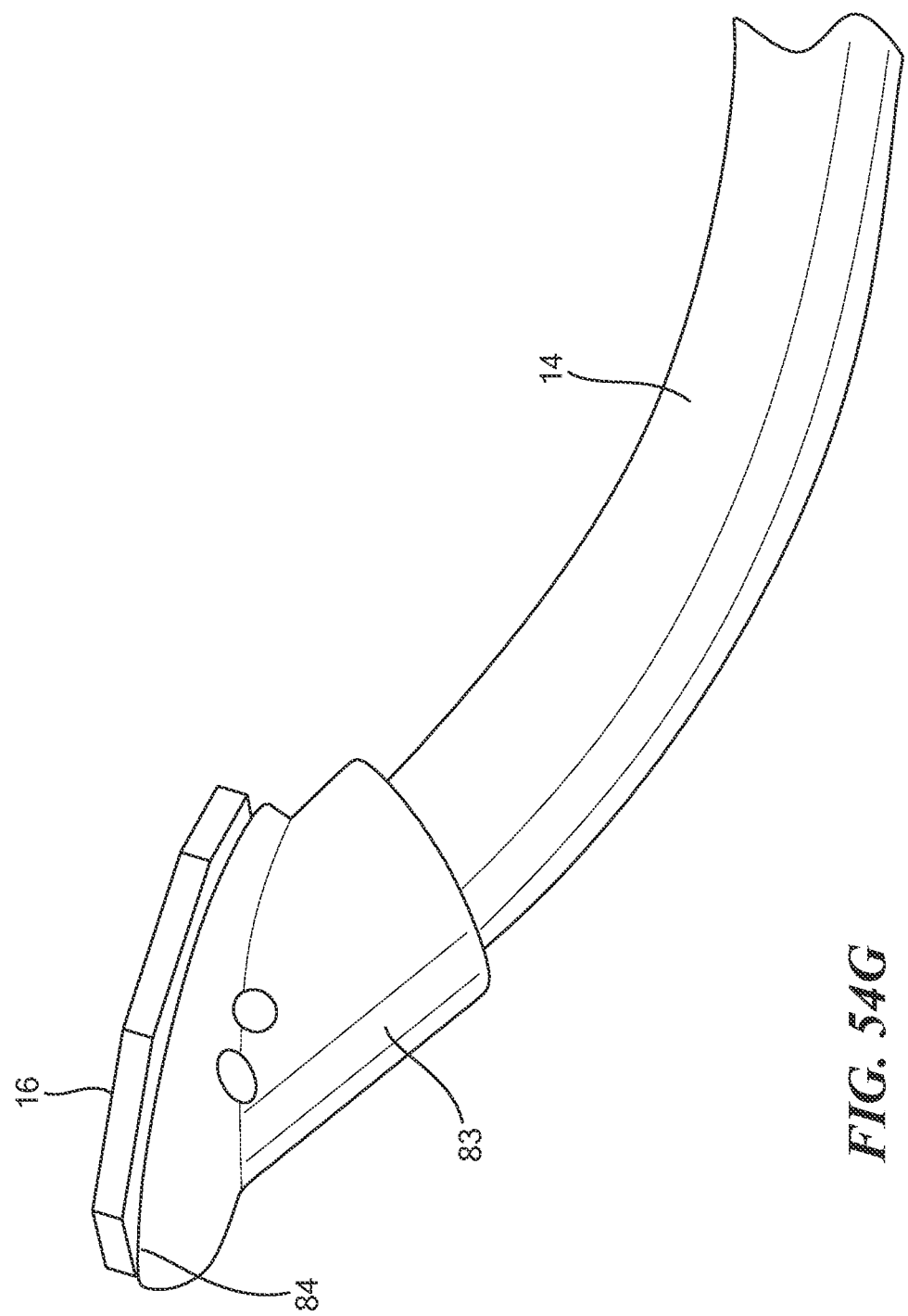

FIG. 54G shows a flexible scope 14, such as an endoscope, manipulating the cap 83 coupled to an anastomosis device 16. By bending the scope 14, the anastomosis device 16 may be manipulated for placement and alignment at a target anastomosis site.

Figure 54H:
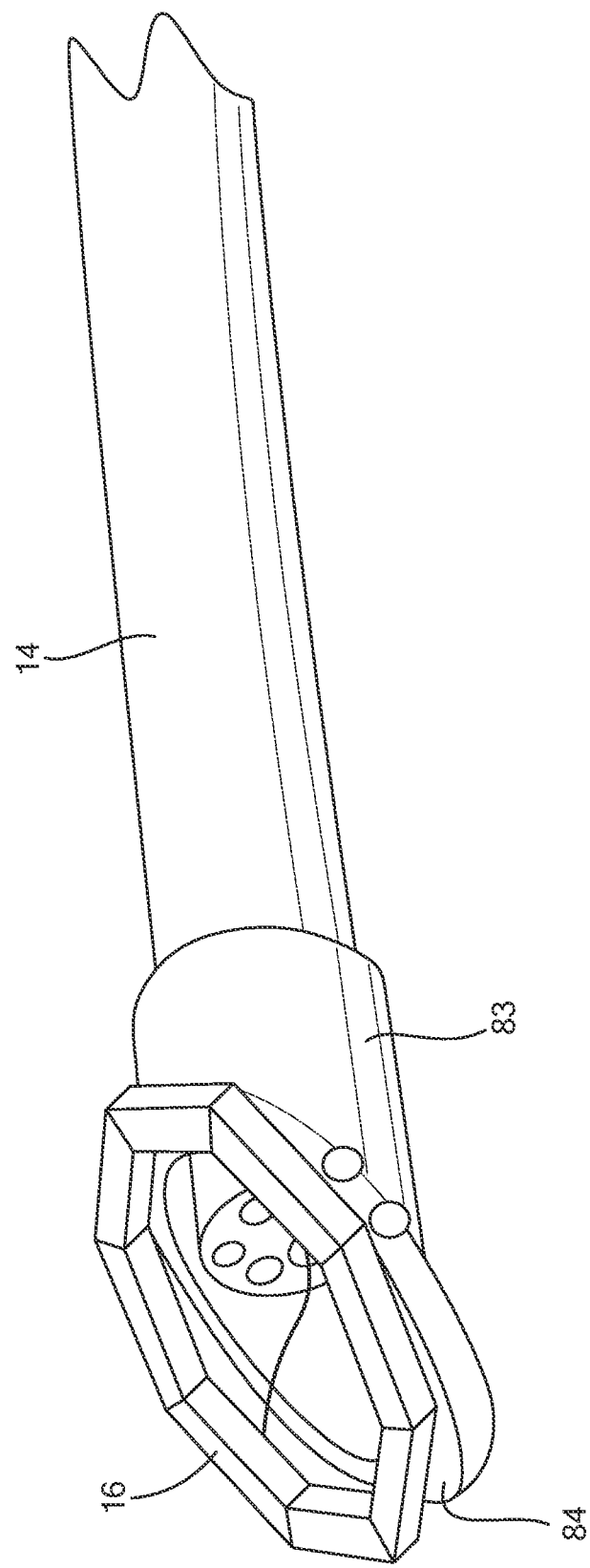

FIG. 54H shows a side-view of a flexible scope 14 with a capture device 83 comprising a cap facia 84 mated to a magnetic anastomosis device 16. The cap facia 84 is in the stored position 45 degrees relative to the endoscope 14.

Figure 54I:
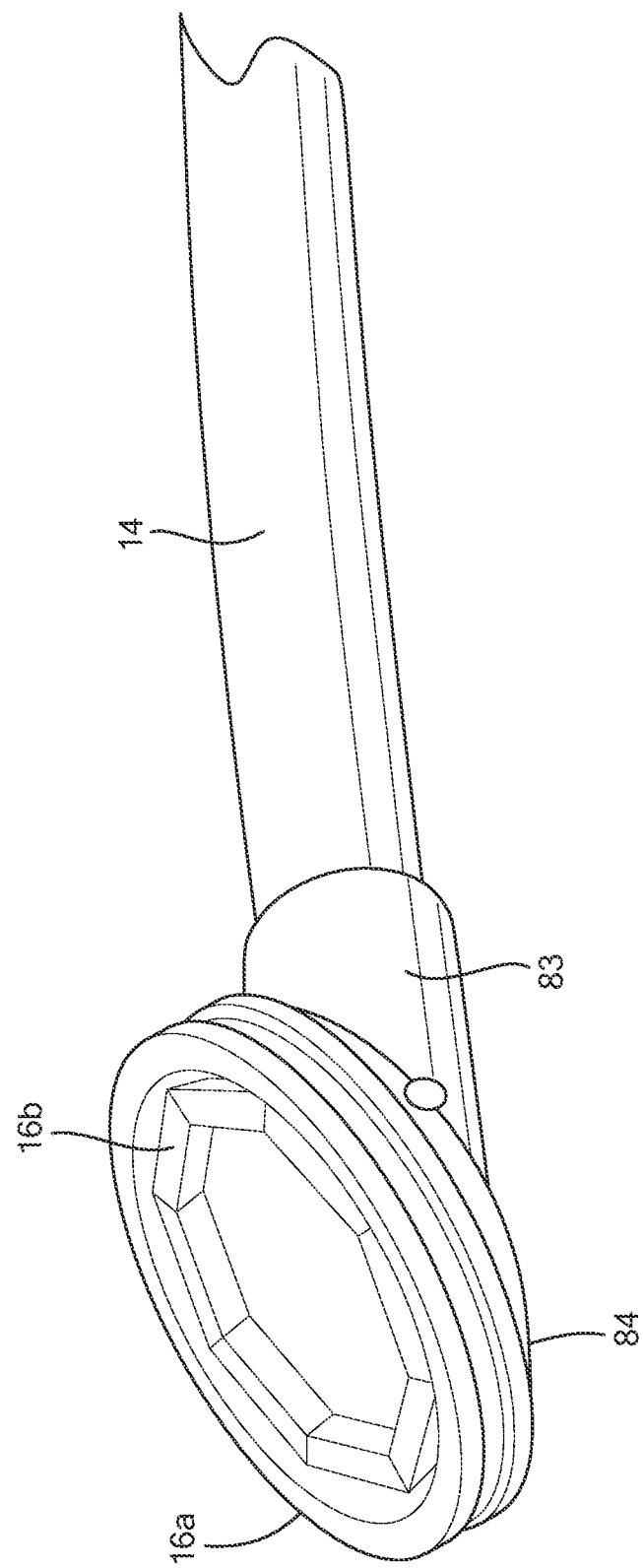

FIG. 54I shows a simulation of mating of the captured compression anastomosis device 16b with a corresponding compression anastomosis device 16a.

FIG. 54J shows a simulation of the captured compression anastomosis device 16 releasing from the delivery device 14 due to proper alignment of the two compression anastomosis devices producing a coupling force that overcomes the holding force produced by the cap 83 on the captured compression anastomosis device 16. The surgeon may pull back on the delivery device 14 to decouple the cap facia 84 with the captured anastomosis device 16 in order to remove the delivery device 14 and cap 83 from the patient, leaving behind the compression anastomosis devices.

Figure 53:
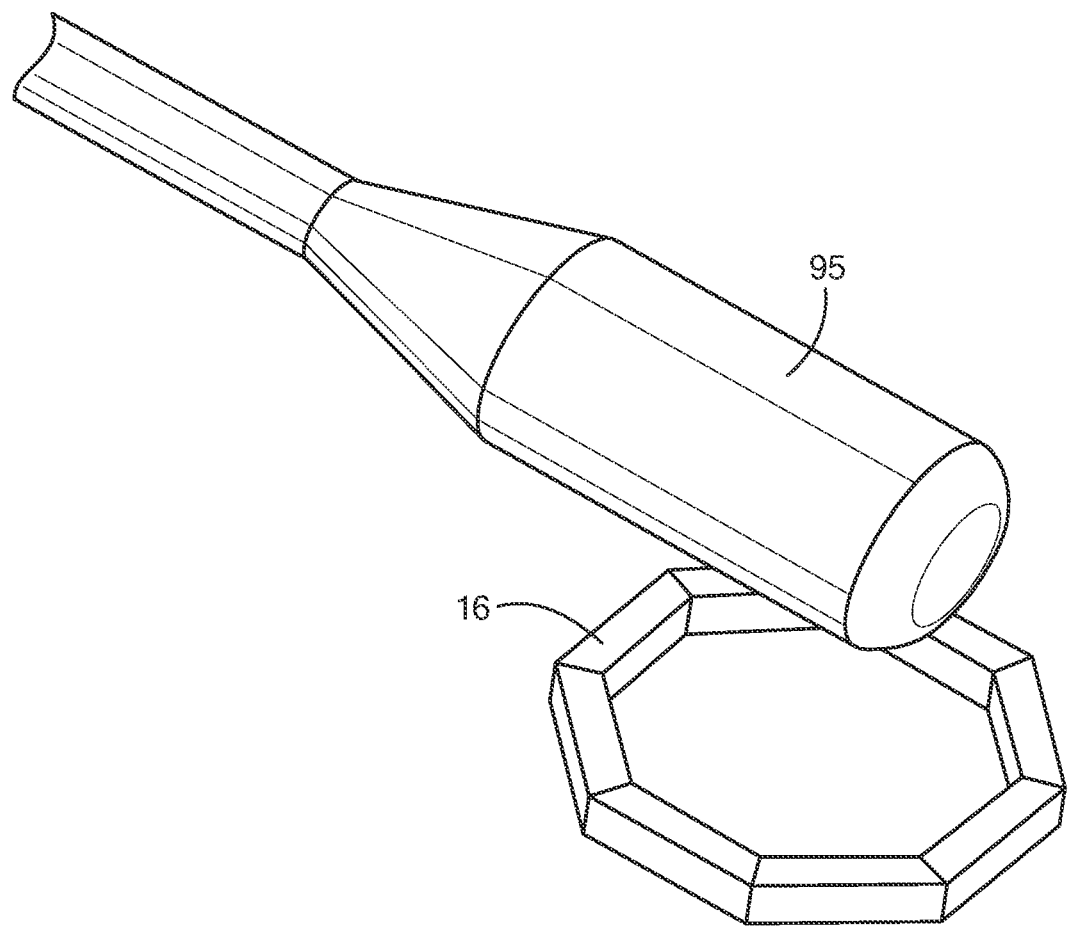
FIG. 53 is a schematic diagram showing a laparoscopic magnet navigation device for controlling movement of a magnetic device within the GI tract or other cavity, in accordance with certain exemplary embodiments.

FIG. 53 shows a laparoscopic magnet navigation device 95 for controlling movement of a magnetic device 16 within the GI tract or other cavity, in accordance with certain exemplary embodiments. The following are some exemplary configurations for such a laparoscopic magnet navigation device:

(a) Ferrous laparoscopic tool—Utilizing a tool with ferromagnetic mass balanced to allow movement of the magnets through the GI tract starting in the stomach and pulling through bowel without creating trauma. This will be achieved by using a gap controlling tip at the end of the laparoscopic wand. Maintaining the gap will allow the forces displaced on the magnet to be great enough to drag and manipulate through anatomical tortuosity without allowing the magnet and tool to "pinch" tissue.

(b) Static field laparoscopic tool—Like the ferrous tool, this would also have to be a balanced mass approach to have enough attractive force to allow manipulation without pinching tissue. The advantage of using another magnet would be reduced footprint and mass of the laparoscopic wand.

(c) Electromagnetic field laparoscopic tool—Utilizing a variable field laparoscopic manipulation tool would offer great benefits. Tracking through challenging anatomical features such as the pylorus or any other narrowing/sphinctered areas in the GI tract could prove difficult. Being able to vibrate and jostle the magnet as it approached these anatomical structures would allow much greater dexterity in manipulating the magnet as well as providing a very strong field without the worry of pinching tissue. Pulsing the electromagnetic wand with different wave forms and patterns would allow the user to have the magnet at a distance away from the tip and float through the anatomy.

The distal end of the laparoscopic navigation device 95 may comprise a magnet or ferromagnetic metal, such that when capturing a magnetic anastomosis device 16b, the attractive force between two anastomosis devices 16a, 16b is stronger than the magnetic attraction between the laparoscopic navigation device 95 and the captured magnet 16b. Thus, because the attractive forces between the laparoscopic device 95 and the captured magnet 16b is less than the attractive forces between the pair of magnets 16a, 16b, the laparoscopic device may be easily removed from the patient without disturbing the placement of the pair of magnetic anastomosis devices 16a, 16b.

It should be noted that magnetic navigation devices of the type shown in FIG. 53 essentially have a single point of contact or focus of interaction with the compression anastomosis device 16 or other target device cap and can include any of the elements described above, e.g., magnets or other mechanism for capturing an anastomosis device, selective sensing and release of the anastomosis device based on the coupling force, a pivoting mechanism to allow the captured anastomosis device to be presented at an angle after capture, a universal joint or other mechanism providing additional degrees of freedom, actuators for controlling the position and movement of the device, and/or electronic sensors and/or actuators.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

Potential Claims

Various embodiments of the present invention may be characterized by the potential claims listed in the paragraphs following this paragraph (and before the actual claims provided at the end of the application). These potential claims form a part of the written description of the application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public. Nor are these potential claims intended to limit various pursued claims.

Without limitation, potential subject matter that may be claimed (prefaced with the letter "P" so as to avoid confusion with the actual claims presented below) includes:

P1. A cap having a circumferential outer skirt for engaging a shaft or tube member such as endoscope and having a circumferential resilient material for better clamping.

P2. A cap having a substantially clear material to permit viewing through the CAP.

P3. An apparatus with the ability to capture and control a compression anastomosis device in a proximal lumen, allowing for presentation at different angles relative to the delivery device to allow for less invasive intraluminal translation and/or improved mating position.

P4. An apparatus having sensing force optimized to automatically release properly mated compression anastomosis devices and to maintain sufficient holding force for improperly mated devices to be decoupled, realigned, and properly mated.

P5. A cap having a feedback capability for the user in real time.

P6. A cap having ability to understand tissue type and/or thickness and/or blood flow or perfusion.

P7. Apparatus, device, and method to control and manipulate magnets that will use the magnetic field sensing to provide user with confidence that the magnet has been deployed for a property anastomosis to be made.

P8. A laparoscopic magnetic navigation device.

P9. The device of claim P8, wherein the device is a ferrous laparoscopic device.

P10. The device of claim P8, wherein the device is a static field laparoscopic device.

P11. The device of claim P8, wherein the device is an electromagnetic field laparoscopic device in which the magnetic field can be varied electromagnetically.

P12. A cap for a delivery device such as an endoscope, laparoscope, catheter, etc., the cap including any feature or combination of features as described.

P13. A delivery device such as an endoscope, laparoscope, catheter, etc., having a cap including any feature or combination of features as described.

P14. A device such as an endoscope, laparoscope, catheter, etc., having a distal end including an articulating element for selectively capturing, manipulating, and releasing a target device in accordance with any feature or combination of features described.

P15. A device such as an endoscope, laparoscope, catheter, etc., having a distal end including an element for selectively capturing, manipulating, and releasing a target device in accordance with any feature or combination of features described, wherein the element is configured to release the target device only when a separation force on the target device is greater than a holding force of the element.

P16. A device such as an endoscope, laparoscope, catheter, etc., having a distal end including an element for selectively capturing, manipulating, and releasing a target device in accordance with any feature or combination of features described, wherein the element is configured to release the target device only when a separation force on the target device is greater than a predetermined separation force.

P17. A device such as an endoscope, laparoscope, catheter, etc., having a distal end including an element for selectively capturing, manipulating, and releasing a target device in accordance with any feature or combination of features described, wherein the element is configured to release the target device only when a magnetic field interacting with the target device is greater than a predetermined level.

P18. A device configured to capture and control a rigid magnet such as for steering the magnet into position for an anastomosis procedure.

P19. A medical device having a distal end, the medical device comprising:
a cap configured for attaching to the distal end of the medical device, the cap including a magnetizable portion;
a first magnet for attaching to the magnetizable portion of the cap;
the cap and the first magnet having a first force therebetween;
a second magnet for attaching to the first magnet and having a second force therebetween; and
the second force being greater than the first force for separating the first magnet from the cap.

P20. The apparatus of claim P19 further comprising:
sensing capabilities to detect magnetic force to capture and/or release a magnetic anastomosis device.

P21. The apparatus of claim P19 further comprising:
the cap having a substantially clear material to allow viewing through the cap.

P22. The apparatus of claim P19 further comprising:
the cap having an inner working channel throughout the length of the cap to allow material to pass through the cap.

P23. The apparatus of claim P19 further comprising:
a sensing force optimized to automatically release properly mated compression anastomosis devices and to maintain sufficient holding force for improperly mated devices to be decoupled, realigned, and properly mated.

P24. The apparatus of claim P19 further comprising:
a feedback capability for a user in real time.

P25. The apparatus of claim P19 further comprising:
the ability to understand tissue type and/or thickness and/or blood flow or perfusion.

P26. The apparatus of claim P19 further comprising:
control guides attached to the cap facia capable of articulating the cap facia relative to the cap body.

P27. The apparatus of claim P19 further comprising:
a spring-loaded shaft member in the cap body capable of releasing the cap facia from a stored position to a deployed position.

P28. The apparatus of claim P19 further comprising:
one or more channels within the cap body having a capability of passing fluid and/or air through the cap body.

P29. The apparatus of claim P19 further wherein the cap facia comprises one or more arms capable of capturing and manipulating a magnetic device.

What is claimed is:

1. An apparatus for capturing and manipulating a magnetic compression anastomosis device, the apparatus comprising:
a cap configured to attach to a delivery device, the cap comprising:
a cap body having a distal end and a proximal end through which the cap body is coupled to the delivery device; and
an articulating cap facia coupled at the distal end of the cap body and movable between at least a closed position and a fully-opened position, the articulating cap facia including at least one capture device configured to capture a magnetic anastomosis device, wherein the cap facia has a diameter greater than a diameter of the cap body.

2. The apparatus of claim 1, wherein:
in the closed position, the cap facia is angled substantially with an angled distal end geometry, and
in the fully-opened position, the cap facia is pivoted away from the angled distal end geometry.

3. The apparatus of claim 1, wherein the at least one capture device includes one or more magnets.

4. The apparatus of claim 1, wherein the at least one capture device includes at least one electromagnet configured to provide a fixed magnetic field strength.

5. The apparatus of claim 1, wherein the at least one capture device includes at least one electromagnet configured to provide different magnetic field strengths for capturing, holding, and releasing compression anastomosis devices over a range of conditions.

6. The apparatus of claim 1, wherein the at least one capture device includes at least one device capable of grasping or retaining the magnetic anastomosis device.

7. The apparatus of claim 1, wherein the cap facia is coupled to the cap body using at least one pivot.

8. The apparatus of claim 7, wherein the at least one pivot includes one or more pins.

9. The apparatus of claim 7, wherein the at least one pivot includes at least one hinge.

10. The apparatus of claim 7, wherein the at least one pivot includes at least one ball-and-socket joint.

11. The apparatus of claim 1, wherein the closed position is less than or equal to approximately 45 degrees relative to a nominal plane of the delivery device.

12. The apparatus of claim 1, wherein the fully-opened position is greater than or equal to approximately 90 degrees relative to a nominal plane of the delivery device.

13. The apparatus of claim 1, wherein the cap facia includes an extension that causes the cap facia to move from the closed position toward the fully-opened position when pressure is applied to the extension.

14. The apparatus of claim 1, wherein the cap facia is configured to move from the closed position toward the fully-opened position when a sufficient magnetic interaction force exists between a magnetic anastomosis device captured by the cap facia and an opposing magnetic anastomosis device.

15. The apparatus of claim 1, wherein the cap further comprises:
an actuator configured to remotely control position of the cap facia relative to the cap body.

16. The apparatus of claim 15, wherein the actuator comprises a spring-loaded mechanism capable of releasing the cap facia from the closed position to the fully-opened position.

17. The apparatus of claim 1, wherein the distal end of the cap body is movable relative to the proximal end of the cap body.

18. The apparatus of claim 17, wherein the cap body includes a universal joint, hinge, or ball-and-socket joint between the distal end and the proximal end to allow movement of the distal end relative to the proximal end.

19. The apparatus of claim 17, wherein the cap further comprises:
at least one sensor to sense position of the distal end relative to the proximal end and provide position feedback to a user.

20. The apparatus of claim 17, wherein the cap further comprises:
an actuator configured to remotely control position of the distal end relative to the proximal end.

21. The apparatus of claim 1, wherein the cap body is formed of a substantially clear material to permit viewing through the cap.

22. The apparatus of claim 1, wherein the cap body includes at least one channel extending through the cap body.

23. The apparatus of claim 22, wherein at least one of:
the at least one channel is adapted for passing of fluid and/or air through the cap body;
the at least one channel is adapted for passing an instrument through the cap body;
the at least one channel is adapted for allowing visibility through the cap body; or
the at least one channel is adapted for delivering suction through the cap body.

24. The apparatus of claim 1, wherein the at least one capture device is configured to automatically release the captured magnetic anastomosis device when the captured magnetic anastomosis device is properly mated with an opposing magnetic anastomosis device and to retain the captured magnetic anastomosis device when the captured magnetic anastomosis device is insufficiently mated with an opposing magnetic anastomosis device.

25. The apparatus of claim 1, further comprising the delivery device attached to the cap.

26. The apparatus of claim 25, wherein the delivery device is one of:
an endoscope;
a laparoscope, or
a catheter.

27. An apparatus for capturing and manipulating a magnetic compression anastomosis device, the apparatus comprising:
- a cap configured to attach to a delivery device, the cap comprising:
  - a cap body having a distal end and a proximal end through which the cap body is coupled to the delivery device; and
  - an articulating cap facia coupled at the distal end of the cap body and movable between at least a closed position and a fully-opened position, the articulating cap facia including at least one capture device configured to capture a magnetic anastomosis device, wherein the at least one capture device includes at least one adhesive device.

28. An apparatus for capturing and manipulating a magnetic compression anastomosis device, the apparatus comprising:
- a cap configured to attach to a delivery device, the cap comprising:
  - a cap body having a distal end and a proximal end through which the cap body is coupled to the delivery device; and
  - an articulating cap facia coupled at the distal end of the cap body and movable between at least a closed position and a fully-opened position, the articulating cap facia including at least one capture device configured to capture a magnetic anastomosis device, further comprising:
- a biasing device configured to bias the cap facia toward the closed position.

29. The apparatus of claim 28, wherein the biasing device includes one or more springs.

30. An apparatus for capturing and manipulating a magnetic compression anastomosis device, the apparatus comprising:
- a cap configured to attach to a delivery device, the cap comprising:
  - a cap body having a distal end and a proximal end through which the cap body is coupled to the delivery device; and
  - an articulating cap facia coupled at the distal end of the cap body and movable between at least a closed position and a fully-opened position, the articulating cap facia including at least one capture device configured to capture a magnetic anastomosis device, wherein the cap body is movable relative to the delivery device, the cap body includes a universal joint, hinge, or ball-and-socket joint to be movable relative to the delivery device, and the cap further comprises:
    - an actuator configured to remotely control position of the distal end relative to the proximal end.

* * * * *